United States Patent
Gong et al.

(10) Patent No.: US 10,988,762 B2
(45) Date of Patent: Apr. 27, 2021

(54) REVERSE TRANSCRIPTASES AND USES THEREOF

(71) Applicant: Bio-Rad Laboratories, Inc., Hercules, CA (US)

(72) Inventors: Xiao-Song Gong, Hercules, CA (US); Yan Wang, Hercules, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 15/895,504

(22) Filed: Feb. 13, 2018

(65) Prior Publication Data

US 2018/0230462 A1 Aug. 16, 2018

Related U.S. Application Data

(60) Provisional application No. 62/459,974, filed on Feb. 16, 2017.

(51) Int. Cl.
| | | |
|---|---|---|
| *C12N 9/10* | (2006.01) | |
| *C12N 9/22* | (2006.01) | |
| *C12N 15/10* | (2006.01) | |
| *C12Q 1/686* | (2018.01) | |
| *C12Q 1/6844* | (2018.01) | |

(52) U.S. Cl.
CPC .......... *C12N 15/1096* (2013.01); *C12N 9/22* (2013.01); *C12Q 1/686* (2013.01); *C12N 2770/00022* (2013.01); *C12Q 1/6844* (2013.01)

(58) Field of Classification Search
CPC ......... C12N 9/10; C12N 9/22; C12N 15/1096
See application file for complete search history.

(56) References Cited

U.S. PATENT DOCUMENTS

| | | |
|---|---|---|
| 5,244,797 A | 9/1993 | Kotewicz et al. |
| 5,405,776 A | 4/1995 | Kotewicz et al. |
| 5,668,005 A | 9/1997 | Kotewicz et al. |
| 6,721,004 B1 | 4/2004 | Kato |
| 7,595,179 B2 | 9/2009 | Chen et al. |
| 8,361,754 B2 | 1/2013 | Chen et al. |
| 8,753,845 B2 | 6/2014 | Dhariwal et al. |
| 8,956,841 B2 | 2/2015 | Chen et al. |
| 2014/0286907 A1 | 9/2014 | Sarkis et al. |
| 2014/0363854 A1 | 12/2014 | Smith et al. |
| 2016/0194678 A1 | 7/2016 | Martin et al. |
| 2017/0159032 A1 | 6/2017 | Gong |

FOREIGN PATENT DOCUMENTS

EP 0377842 A1 7/1990

OTHER PUBLICATIONS

Operario et al., Virology, vol. 335, pp. 106-121, 2005.*
Misra et al., Journal of Biological Chemistry vol. 273, No. 17, pp. 9785-9789, 1998.*
Tanese et al., Proc. Natl. Acad. Sci. USA, vol. 85, pp. 1777-1781, Mar. 1988.*
Das and Georgiadis, Structure, vol. 12, pp. 819-829, May 2004.*

(Continued)

*Primary Examiner* — Richard G Hutson
(74) *Attorney, Agent, or Firm* — Kilpatrick Townsend and Stockton LLP

(57) ABSTRACT

Hybrid reverse transcriptases formed from portions of FLVRT and MLVRT are provided.

11 Claims, 1 Drawing Sheet
Specification includes a Sequence Listing.

RT mutant expression analysis
soluble fraction on SDS-PAGE gel

1. Wt MLV RT
2. Truncated FLV RT
3. Wt FLV RT
4. FM1 (1/3F 2/3M)
5. FM2 (2/3F 1/3M)
6. MF (1/3M 2/3F)
7. MFP (1/3M 2/3F)

*: indicates the expressed recombinant RT band.

(56) References Cited

OTHER PUBLICATIONS

International Search Report and Written Opinion from PCT/US2018/017977 dated May 23, 2018; 9 pages.
Stewart, H. et al.; "Complete genome sequences of two feline leukemia virus subgroup B isolates with novel recombination sites"; *Genome Announcements;* vol. 1, No. 1; Jan. 15, 2013; 2 pages.
Extended European Search Report in EP Appln. 18754654.4 dated Oct. 19, 2020; 9 pages.
Sharma, S.K. et al.; "Engineering of the human-immunodeficiency-virus-type-1 (HIV-1) reverse transcriptase gene to prevent dimerization of the expressed chimaeric protein: Purification and characterization of a monomeric reverse-transcriptase"; *Biotechnology and Applied Biochemistry;* vol. 19, No. 1; Jan. 1, 1994; pp. 155-167.
Yasukawa, K. et al.; "Characterization of Moloney Murine Leukaemia Virus/Avian Myeloblastosis Virus Chimeric Reverse Transcriptases"; *Journal of Biochemistry;* vol. 145, No. 3; Jan. 4, 2009; pp. 315-324.
Arezi, B. et al.; "Novel mutations in Moloney Murine Leukemia Virus reverse transcriptase increase thermostability through tighter binding to template-primer"; *Nucleic Acids Research;* vol. 37, No. 2; 2009; pp. 473-481.
Baranauskas, A. et al.; "Generation and characterization of new highly thermostable and processive M-MuLV reverse transcriptase variants"; *Protein Engineering, Design & Selection;* vol. 25, No. 10; Jun. 12, 2012; pp. 657-668.
Blain, S.W. et al.; "Differential Effects of Moloney Murine Leukemia Virus Reverse Transcriptase Mutations on RNase H Activity in $Mg^{2+}$ and $Mn^{2+}$;"; *The Journal of Biological Chemistry;* vol. 271, No. 3; Jan. 19, 1996; pp. 1448-1454.
Skirgaila, R. et al.; "Compartmentalization of destabilized enzyme-mRNA-ribosome complexes generated by ribosome display: a novel tool for the directed evolution of enzymes"; *Protein Engineering, Design & Selection;* vol. 26, No. 78; May 10, 2013; pp. 453-461.

* cited by examiner

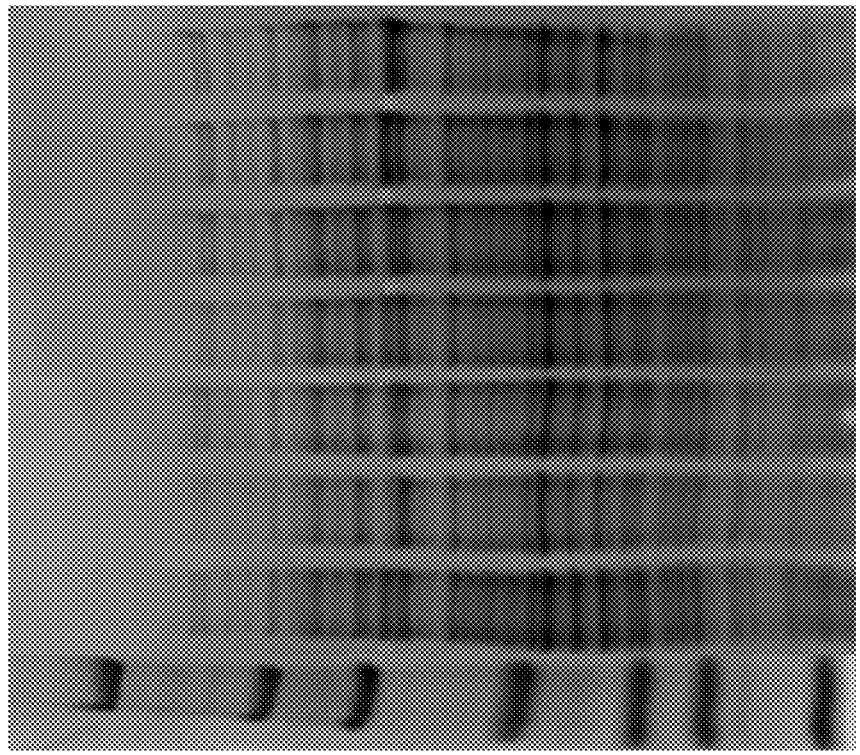

SEQUENCE LISTING

<160> NUMBER OF SEQ ID NOS: 42

<210> SEQ ID NO 1
<211> LENGTH: 222
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (140)..(140)
<223> OTHER INFORMATION: Xaa = Leu or Pro
<220> FEATURE:
<221> NAME/KEY: MISC_FEATURE
<222> LOCATION: (201)..(201)
<223> OTHER INFORMATION: Xaa = Asp or Asn

<400> SEQUENCE: 1

Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Xaa Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Xaa Glu Ala Leu His Arg Asp Leu
        195                 200                 205

Ala Asp Phe Arg Ile Gln His Pro Asp Leu Ile Leu Leu Gln
    210                 215                 220

<210> SEQ ID NO 2
<211> LENGTH: 278
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (140)..(140)
<223> OTHER INFORMATION: Xaa = Leu or Pro
<220> FEATURE:
<221> NAME/KEY: MISC_FEATURE
<222> LOCATION: (201)..(201)
<223> OTHER INFORMATION: Xaa = Asp or Asn

<400> SEQUENCE: 2

```
Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Xaa Pro Pro Ser His
130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Xaa Glu Ala Leu His Arg Asp Leu
        195                 200                 205

Ala Asp Phe Arg Ile Gln His Pro Asp Leu Ile Leu Leu Gln Tyr Val
210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln
        275
```

<210> SEQ ID NO 3
<211> LENGTH: 222
<212> TYPE: PRT
<213> ORGANISM: Artificial Sequence
<220> FEATURE:
<223> OTHER INFORMATION: Synthetic construct

<400> SEQUENCE: 3

```
Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
50                  55                  60

Tyr Pro Met Ser Gln Glu Ala Arg Leu Gly Ile Lys Pro His Ile Gln
```

```
                65                  70                  75                  80
Arg Leu Leu Asp Gln Gly Ile Leu Val Pro Cys Gln Ser Pro Trp Asn
                    85                  90                  95

Thr Pro Leu Leu Pro Val Lys Lys Pro Gly Thr Asn Asp Tyr Arg Pro
                100                 105                 110

Val Gln Asp Leu Arg Glu Val Asn Lys Arg Val Glu Asp Ile His Pro
            115                 120                 125

Thr Val Pro Asn Pro Tyr Asn Leu Leu Ser Gly Pro Pro Ser His
        130                 135                 140

Gln Trp Tyr Thr Val Leu Asp Leu Lys Asp Ala Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
                180                 185                 190

Phe Lys Asn Ser Pro Thr Leu Phe Asn Glu Ala Leu His Arg Asp Leu
                195                 200                 205

Ala Asp Phe Arg Ile Gln His Pro Asp Leu Ile Leu Leu Gln
        210                 215                 220

<210> SEQ ID NO 4
<211> LENGTH: 278
<212> TYPE: PRT
<213> ORGANISM: Artificial Sequence
<220> FEATURE:
<223> OTHER INFORMATION: Synthetic construct

<400> SEQUENCE: 4

Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
                20                  25                  30

Ala Trp Ala Glu Thr Gly Gly Met Gly Leu Ala Val Arg Gln Ala Pro
            35                  40                  45

Leu Ile Ile Pro Leu Lys Ala Thr Ser Thr Pro Val Ser Ile Lys Gln
        50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
                100                 105                 110

Val Gln Asp Leu Arg Glu Val Asn Lys Arg Val Glu Asp Ile His Pro
            115                 120                 125

Thr Val Pro Asn Pro Tyr Asn Leu Leu Ser Gly Pro Pro Ser His
        130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
                180                 185                 190

Phe Lys Asn Ser Pro Thr Leu Phe Asn Glu Ala Leu His Arg Asp Leu
                195                 200                 205

Ala Asp Phe Arg Ile Gln His Pro Asp Leu Ile Leu Leu Gln Tyr Val
```

-continued

```
                210                 215                 220
Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
                260                 265                 270

Leu Leu Lys Glu Gly Gln
                275

<210> SEQ ID NO 5
<211> LENGTH: 391
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (245)..(245)
<223> OTHER INFORMATION: Xaa = Asp, Gly, Asn, or Ala
<220> FEATURE:
<221> NAME/KEY: MISC_FEATURE
<222> LOCATION: (249)..(249)
<223> OTHER INFORMATION: Xaa = Phe or Ile
<220> FEATURE:
<221> NAME/KEY: MISC_FEATURE
<222> LOCATION: (315)..(315)
<223> OTHER INFORMATION: Xaa = His or Lys
<220> FEATURE:
<221> NAME/KEY: MISC_FEATURE
<222> LOCATION: (324)..(324)
<223> OTHER INFORMATION: Xaa = Leu or Trp
<220> FEATURE:
<221> NAME/KEY: MISC_FEATURE
<222> LOCATION: (328)..(328)
<223> OTHER INFORMATION: Xaa = Glu or Lys
<220> FEATURE:
<221> NAME/KEY: MISC_FEATURE
<222> LOCATION: (355)..(355)
<223> OTHER INFORMATION: Xaa = His or Tyr

<400> SEQUENCE: 5

Arg Trp Leu Thr Lys Ala Arg Lys Glu Ala Ile Leu Ser Ile Pro Val
1               5                   10                  15

Pro Lys Asn Pro Arg Gln Val Arg Glu Phe Leu Gly Thr Ala Gly Tyr
                20                  25                  30

Cys Arg Leu Trp Ile Pro Gly Phe Ala Glu Leu Ala Ala Pro Leu Tyr
                35                  40                  45

Pro Leu Thr Arg Pro Gly Thr Leu Phe Gln Trp Gly Thr Glu Gln Gln
            50                  55                  60

Leu Ala Phe Glu Asn Ile Arg Lys Ala Leu Leu Ser Ser Pro Ala Leu
65              70                  75                  80

Gly Leu Pro Asp Ile Thr Lys Pro Phe Glu Leu Phe Ile Asp Glu Asn
                85                  90                  95

Ser Gly Phe Ala Lys Gly Val Leu Val Gln Lys Leu Gly Pro Trp Lys
                100                 105                 110

Arg Pro Val Ala Tyr Leu Ser Lys Lys Leu Asp Thr Val Ala Ser Gly
            115                 120                 125

Trp Pro Pro Cys Leu Arg Met Val Ala Ala Ile Ala Ile Leu Val Lys
            130                 135                 140

Asp Ala Gly Lys Leu Thr Leu Gly Gln Pro Leu Thr Ile Leu Thr Ser
145                 150                 155                 160

His Pro Val Glu Ala Leu Val Arg Gln Pro Pro Asn Lys Trp Leu Ser
```

```
                    165                 170                 175
Asn Ala Arg Met Thr His Tyr Gln Ala Met Leu Leu Asp Ala Glu Arg
            180                 185                 190

Val His Phe Gly Pro Thr Val Ser Leu Asn Pro Ala Thr Leu Leu Pro
        195                 200                 205

Leu Pro Ser Gly Lys Pro Pro Arg Leu Ser Pro Asp Leu Ala Glu Thr
    210                 215                 220

Met Ala Gln Thr Asp Leu Thr Asp Gln Pro Leu Pro Asp Ala Asp Leu
225                 230                 235                 240

Thr Trp Tyr Thr Xaa Gly Ser Ser Xaa Ile Arg Asn Gly Glu Arg Lys
                245                 250                 255

Ala Gly Ala Ala Val Thr Thr Glu Ser Glu Val Ile Trp Ala Ala Ser
            260                 265                 270

Leu Pro Pro Gly Thr Ser Ala Gln Arg Ala Glu Leu Ile Ala Leu Thr
        275                 280                 285

Gln Ala Leu Lys Met Ala Lys Gly Lys Lys Leu Thr Val Tyr Thr Asp
    290                 295                 300

Ser Arg Tyr Ala Phe Ala Thr Ala His Val Xaa Gly Glu Ile Tyr Arg
305                 310                 315                 320

Arg Arg Gly Xaa Leu Thr Ser Xaa Gly Lys Glu Ile Lys Asn Lys Asn
                325                 330                 335

Glu Ile Leu Ala Leu Leu Glu Ala Leu Phe Leu Pro Lys Arg Leu Ser
            340                 345                 350

Ile Ile Xaa Cys Pro Gly His Gln Lys Gly Asp Ser Pro Gln Ala Lys
        355                 360                 365

Gly Asn Arg Leu Ala Asp Asp Thr Ala Lys Lys Ala Ala Thr Glu Thr
    370                 375                 380

Gln Ser Ser Leu Thr Ile Leu
385                 390

<210> SEQ ID NO 6
<211> LENGTH: 406
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (245)..(245)
<223> OTHER INFORMATION: Xaa = Asp, Gly, Asn, or Ala
<220> FEATURE:
<221> NAME/KEY: MISC_FEATURE
<222> LOCATION: (249)..(249)
<223> OTHER INFORMATION: Xaa = Phe or Ile
<220> FEATURE:
<221> NAME/KEY: MISC_FEATURE
<222> LOCATION: (315)..(315)
<223> OTHER INFORMATION: Xaa = His or Lys
<220> FEATURE:
<221> NAME/KEY: MISC_FEATURE
<222> LOCATION: (324)..(324)
<223> OTHER INFORMATION: Xaa = Leu or Trp
<220> FEATURE:
<221> NAME/KEY: MISC_FEATURE
<222> LOCATION: (328)..(328)
<223> OTHER INFORMATION: Xaa = Glu or Lys
<220> FEATURE:
<221> NAME/KEY: MISC_FEATURE
<222> LOCATION: (355)..(355)
<223> OTHER INFORMATION: Xaa = His or Tyr

<400> SEQUENCE: 6

Arg Trp Leu Thr Lys Ala Arg Lys Glu Ala Ile Leu Ser Ile Pro Val
```

```
            1               5                   10                  15
          Pro Lys Asn Pro Arg Gln Val Arg Glu Phe Leu Gly Thr Ala Gly Tyr
                          20                  25                  30

Cys Arg Leu Trp Ile Pro Gly Phe Ala Glu Leu Ala Ala Pro Leu Tyr
                          35                  40                  45

Pro Leu Thr Arg Pro Gly Thr Leu Phe Gln Trp Gly Thr Glu Gln Gln
                          50                  55                  60

Leu Ala Phe Glu Asn Ile Arg Lys Ala Leu Leu Ser Ser Pro Ala Leu
           65                  70                  75                  80

Gly Leu Pro Asp Ile Thr Lys Pro Phe Glu Leu Phe Ile Asp Glu Asn
                              85                  90                  95

Ser Gly Phe Ala Lys Gly Val Leu Val Gln Lys Leu Gly Pro Trp Lys
                          100                 105                 110

Arg Pro Val Ala Tyr Leu Ser Lys Lys Leu Asp Thr Val Ala Ser Gly
                          115                 120                 125

Trp Pro Pro Cys Leu Arg Met Val Ala Ala Ile Ala Ile Leu Val Lys
                          130                 135                 140

Asp Ala Gly Lys Leu Thr Leu Gly Gln Pro Leu Thr Ile Leu Thr Ser
          145                 150                 155                 160

His Pro Val Glu Ala Leu Val Arg Gln Pro Pro Asn Lys Trp Leu Ser
                              165                 170                 175

Asn Ala Arg Met Thr His Tyr Gln Ala Met Leu Leu Asp Ala Glu Arg
                          180                 185                 190

Val His Phe Gly Pro Thr Val Ser Leu Asn Pro Ala Thr Leu Leu Pro
                          195                 200                 205

Leu Pro Ser Gly Lys Pro Pro Arg Leu Ser Pro Asp Leu Ala Glu Thr
                          210                 215                 220

Met Ala Gln Thr Asp Leu Thr Asp Gln Pro Leu Pro Ala Asp Leu
          225                 230                 235                 240

Thr Trp Tyr Thr Xaa Gly Ser Ser Xaa Ile Arg Asn Gly Glu Arg Lys
                          245                 250                 255

Ala Gly Ala Ala Val Thr Thr Glu Ser Glu Val Ile Trp Ala Ala Ser
                          260                 265                 270

Leu Pro Pro Gly Thr Ser Ala Gln Arg Ala Glu Leu Ile Ala Leu Thr
                          275                 280                 285

Gln Ala Leu Lys Met Ala Lys Gly Lys Lys Leu Thr Val Tyr Thr Asp
                          290                 295                 300

Ser Arg Tyr Ala Phe Ala Thr Ala His Val Xaa Gly Glu Ile Tyr Arg
          305                 310                 315                 320

Arg Arg Gly Xaa Leu Thr Ser Xaa Gly Lys Glu Ile Lys Asn Lys Asn
                          325                 330                 335

Glu Ile Leu Ala Leu Leu Glu Ala Leu Phe Leu Pro Lys Arg Leu Ser
                          340                 345                 350

Ile Ile Xaa Cys Pro Gly His Gln Lys Gly Asp Ser Pro Gln Ala Lys
                          355                 360                 365

Gly Asn Arg Leu Ala Asp Asp Thr Ala Lys Lys Ala Ala Thr Glu Thr
                          370                 375                 380

Gln Ser Ser Leu Thr Ile Leu Pro Thr Glu Leu Ile Glu Gly Pro Lys
          385                 390                 395                 400

Arg Pro Pro Trp Glu Tyr
                          405

<210> SEQ ID NO 7
```

<211> LENGTH: 391
<212> TYPE: PRT
<213> ORGANISM: Artificial Sequence
<220> FEATURE:
<223> OTHER INFORMATION: Synthetic construct

<400> SEQUENCE: 7

```
Arg Trp Leu Thr Lys Ala Arg Lys Glu Ala Ile Leu Ser Ile Pro Val
1               5                   10                  15

Pro Lys Asn Pro Arg Gln Val Arg Glu Phe Leu Gly Thr Ala Gly Tyr
            20                  25                  30

Cys Arg Leu Trp Ile Pro Gly Phe Ala Glu Leu Ala Ala Pro Leu Tyr
        35                  40                  45

Pro Leu Thr Arg Pro Gly Thr Leu Phe Gln Trp Gly Thr Glu Gln Gln
    50                  55                  60

Leu Ala Phe Glu Asn Ile Arg Lys Ala Leu Leu Ser Ser Pro Ala Leu
65                  70                  75                  80

Gly Leu Pro Asp Ile Thr Lys Pro Phe Glu Leu Phe Ile Asp Glu Asn
                85                  90                  95

Ser Gly Phe Ala Lys Gly Val Leu Val Gln Lys Leu Gly Pro Trp Lys
            100                 105                 110

Arg Pro Val Ala Tyr Leu Ser Lys Lys Leu Asp Thr Val Ala Ser Gly
        115                 120                 125

Trp Pro Pro Cys Leu Arg Met Val Ala Ala Ile Ala Ile Leu Val Lys
    130                 135                 140

Asp Ala Gly Lys Leu Thr Leu Gly Gln Pro Leu Thr Ile Leu Thr Ser
145                 150                 155                 160

His Pro Val Glu Ala Leu Val Arg Gln Pro Pro Asn Lys Trp Leu Ser
                165                 170                 175

Asn Ala Arg Met Thr His Tyr Gln Ala Met Leu Leu Asp Ala Glu Arg
            180                 185                 190

Val His Phe Gly Pro Thr Val Ser Leu Asn Pro Ala Thr Leu Leu Pro
        195                 200                 205

Leu Pro Ser Gly Lys Pro Arg Leu Ser Pro Asp Leu Ala Glu Thr
    210                 215                 220

Met Ala Gln Thr Asp Leu Thr Asp Gln Pro Leu Pro Asp Ala Asp Leu
225                 230                 235                 240

Thr Trp Tyr Thr Ala Gly Ser Ser Ile Ile Arg Asn Gly Glu Arg Lys
                245                 250                 255

Ala Gly Ala Ala Val Thr Thr Glu Ser Glu Val Ile Trp Ala Ala Ser
            260                 265                 270

Leu Pro Pro Gly Thr Ser Ala Gln Arg Ala Glu Leu Ile Ala Leu Thr
        275                 280                 285

Gln Ala Leu Lys Met Ala Lys Gly Lys Lys Leu Thr Val Tyr Thr Asp
    290                 295                 300

Ser Arg Tyr Ala Phe Ala Thr Ala His Val His Gly Glu Ile Tyr Arg
305                 310                 315                 320

Arg Arg Gly Leu Leu Thr Ser Glu Gly Lys Glu Ile Lys Asn Lys Asn
                325                 330                 335

Glu Ile Leu Ala Leu Leu Glu Ala Leu Phe Leu Pro Lys Arg Leu Ser
            340                 345                 350

Ile Ile Tyr Cys Pro Gly His Gln Lys Gly Asp Ser Pro Gln Ala Lys
        355                 360                 365

Gly Asn Arg Leu Ala Asp Asp Thr Ala Lys Lys Ala Ala Thr Glu Thr
    370                 375                 380
```

Gln Ser Ser Leu Thr Ile Leu
385                 390

<210> SEQ ID NO 8
<211> LENGTH: 406
<212> TYPE: PRT
<213> ORGANISM: Artificial Sequence
<220> FEATURE:
<223> OTHER INFORMATION: Synthetic construct

<400> SEQUENCE: 8

Arg Trp Leu Thr Lys Ala Arg Lys Glu Ala Ile Leu Ser Ile Pro Val
1               5                   10                  15

Pro Lys Asn Pro Arg Gln Val Arg Glu Phe Leu Gly Thr Ala Gly Tyr
            20                  25                  30

Cys Arg Leu Trp Ile Pro Gly Phe Ala Glu Leu Ala Ala Pro Leu Tyr
        35                  40                  45

Pro Leu Thr Arg Pro Gly Thr Leu Phe Gln Trp Gly Thr Glu Gln Gln
    50                  55                  60

Leu Ala Phe Glu Asn Ile Arg Lys Ala Leu Leu Ser Ser Pro Ala Leu
65                  70                  75                  80

Gly Leu Pro Asp Ile Thr Lys Pro Phe Glu Leu Phe Ile Asp Glu Asn
                85                  90                  95

Ser Gly Phe Ala Lys Gly Val Leu Val Gln Lys Leu Gly Pro Trp Lys
            100                 105                 110

Arg Pro Val Ala Tyr Leu Ser Lys Lys Leu Asp Thr Val Ala Ser Gly
        115                 120                 125

Trp Pro Pro Cys Leu Arg Met Val Ala Ala Ile Ala Ile Leu Val Lys
    130                 135                 140

Asp Ala Gly Lys Leu Thr Leu Gly Gln Pro Leu Thr Ile Leu Thr Ser
145                 150                 155                 160

His Pro Val Glu Ala Leu Val Arg Gln Pro Pro Asn Lys Trp Leu Ser
                165                 170                 175

Asn Ala Arg Met Thr His Tyr Gln Ala Met Leu Leu Asp Ala Glu Arg
            180                 185                 190

Val His Phe Gly Pro Thr Val Ser Leu Asn Pro Ala Thr Leu Leu Pro
        195                 200                 205

Leu Pro Ser Gly Lys Pro Pro Arg Leu Ser Pro Asp Leu Ala Glu Thr
    210                 215                 220

Met Ala Gln Thr Asp Leu Thr Asp Gln Pro Leu Pro Asp Ala Asp Leu
225                 230                 235                 240

Thr Trp Tyr Thr Gly Gly Ser Ser Phe Ile Arg Asn Gly Glu Arg Lys
                245                 250                 255

Ala Gly Ala Ala Val Thr Thr Glu Ser Glu Val Ile Trp Ala Ala Ser
            260                 265                 270

Leu Pro Pro Gly Thr Ser Ala Gln Arg Ala Glu Leu Ile Ala Leu Thr
        275                 280                 285

Gln Ala Leu Lys Met Ala Lys Gly Lys Lys Leu Thr Val Tyr Thr Asp
    290                 295                 300

Ser Arg Tyr Ala Phe Ala Thr Ala His Val His Gly Glu Ile Tyr Arg
305                 310                 315                 320

Arg Arg Gly Trp Leu Thr Ser Lys Gly Lys Glu Ile Lys Asn Lys Asn
                325                 330                 335

Glu Ile Leu Ala Leu Leu Glu Ala Leu Phe Leu Pro Lys Arg Leu Ser
            340                 345                 350

Ile Ile His Cys Pro Gly His Gln Lys Gly Asp Ser Pro Gln Ala Lys
            355                 360                 365

Gly Asn Arg Leu Ala Asp Asp Thr Ala Lys Lys Ala Ala Thr Glu Thr
370                 375                 380

Gln Ser Ser Leu Thr Ile Leu Pro Thr Glu Leu Ile Glu Gly Pro Lys
385                 390                 395                 400

Arg Pro Pro Trp Glu Tyr
                405

<210> SEQ ID NO 9
<211> LENGTH: 391
<212> TYPE: PRT
<213> ORGANISM: Artificial Sequence
<220> FEATURE:
<223> OTHER INFORMATION: Synthetic construct

<400> SEQUENCE: 9

Arg Trp Leu Thr Lys Ala Arg Lys Glu Ala Ile Leu Ser Ile Pro Val
1               5                   10                  15

Pro Lys Asn Pro Arg Gln Val Arg Glu Phe Leu Gly Thr Ala Gly Tyr
            20                  25                  30

Cys Arg Leu Trp Ile Pro Gly Phe Ala Glu Leu Ala Ala Pro Leu Tyr
        35                  40                  45

Pro Leu Thr Arg Pro Gly Thr Leu Phe Gln Trp Gly Thr Glu Gln Gln
    50                  55                  60

Leu Ala Phe Glu Asn Ile Arg Lys Ala Leu Leu Ser Ser Pro Ala Leu
65                  70                  75                  80

Gly Leu Pro Asp Ile Thr Lys Pro Phe Glu Leu Phe Ile Asp Glu Asn
                85                  90                  95

Ser Gly Phe Ala Lys Gly Val Leu Val Gln Lys Leu Gly Pro Trp Lys
            100                 105                 110

Arg Pro Val Ala Tyr Leu Ser Lys Lys Leu Asp Thr Val Ala Ser Gly
        115                 120                 125

Trp Pro Pro Cys Leu Arg Met Val Ala Ala Ile Ala Ile Leu Val Lys
    130                 135                 140

Asp Ala Gly Lys Leu Thr Leu Gly Gln Pro Leu Thr Ile Leu Thr Ser
145                 150                 155                 160

His Pro Val Glu Ala Leu Val Arg Gln Pro Pro Asn Lys Trp Leu Ser
                165                 170                 175

Asn Ala Arg Met Thr His Tyr Gln Ala Met Leu Leu Asp Ala Glu Arg
            180                 185                 190

Val His Phe Gly Pro Thr Val Ser Leu Asn Pro Ala Thr Leu Leu Pro
        195                 200                 205

Leu Pro Ser Gly Lys Pro Arg Leu Ser Pro Asp Leu Ala Glu Thr
    210                 215                 220

Met Ala Gln Thr Asp Leu Thr Asp Gln Pro Leu Pro Asp Ala Asp Leu
225                 230                 235                 240

Thr Trp Tyr Thr Gly Gly Ser Ser Phe Ile Arg Asn Gly Glu Arg Lys
                245                 250                 255

Ala Gly Ala Ala Val Thr Thr Glu Ser Glu Val Ile Trp Ala Ala Ser
            260                 265                 270

Leu Pro Pro Gly Thr Ser Ala Gln Arg Ala Glu Leu Ile Ala Leu Thr
        275                 280                 285

Gln Ala Leu Lys Met Ala Lys Gly Lys Lys Leu Thr Val Tyr Thr Asp
    290                 295                 300

```
Ser Arg Tyr Ala Phe Ala Thr Ala His Val His Gly Glu Ile Tyr Arg
305                 310                 315                 320

Arg Arg Gly Trp Leu Thr Ser Lys Gly Lys Glu Ile Lys Asn Lys Asn
                325                 330                 335

Glu Ile Leu Ala Leu Leu Glu Ala Leu Phe Leu Pro Lys Arg Leu Ser
            340                 345                 350

Ile Ile His Cys Pro Gly His Gln Lys Gly Asp Ser Pro Gln Ala Lys
        355                 360                 365

Gly Asn Arg Leu Ala Asp Asp Thr Ala Lys Lys Ala Ala Thr Glu Thr
    370                 375                 380

Gln Ser Ser Leu Thr Ile Leu
385                 390

<210> SEQ ID NO 10
<211> LENGTH: 447
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (301)..(301)
<223> OTHER INFORMATION: Xaa = Asp, Gly, Asn, or Ala
<220> FEATURE:
<221> NAME/KEY: MISC_FEATURE
<222> LOCATION: (305)..(305)
<223> OTHER INFORMATION: Xaa = Phe or Ile
<220> FEATURE:
<221> NAME/KEY: MISC_FEATURE
<222> LOCATION: (371)..(371)
<223> OTHER INFORMATION: Xaa = His or Lys
<220> FEATURE:
<221> NAME/KEY: MISC_FEATURE
<222> LOCATION: (380)..(380)
<223> OTHER INFORMATION: Xaa = Leu or Trp
<220> FEATURE:
<221> NAME/KEY: MISC_FEATURE
<222> LOCATION: (384)..(384)
<223> OTHER INFORMATION: Xaa = Glu or Lys
<220> FEATURE:
<221> NAME/KEY: MISC_FEATURE
<222> LOCATION: (411)..(411)
<223> OTHER INFORMATION: Xaa = His or Tyr

<400> SEQUENCE: 10

Tyr Val Asp Asp Leu Leu Leu Ala Ala Ala Thr Arg Thr Glu Cys Leu
1               5                   10                  15

Glu Gly Thr Lys Ala Leu Leu Glu Thr Leu Gly Asn Lys Gly Tyr Arg
            20                  25                  30

Ala Ser Ala Lys Lys Ala Gln Ile Cys Leu Gln Glu Val Thr Tyr Leu
        35                  40                  45

Gly Tyr Ser Leu Lys Asp Gly Gln Arg Trp Leu Thr Lys Ala Arg Lys
    50                  55                  60

Glu Ala Ile Leu Ser Ile Pro Val Pro Lys Asn Pro Arg Gln Val Arg
65                  70                  75                  80

Glu Phe Leu Gly Thr Ala Gly Tyr Cys Arg Leu Trp Ile Pro Gly Phe
                85                  90                  95

Ala Glu Leu Ala Ala Pro Leu Tyr Pro Leu Thr Arg Pro Gly Thr Leu
            100                 105                 110

Phe Gln Trp Gly Thr Glu Gln Gln Leu Ala Phe Glu Asn Ile Arg Lys
        115                 120                 125

Ala Leu Leu Ser Ser Pro Ala Leu Gly Leu Pro Asp Ile Thr Lys Pro
    130                 135                 140
```

```
Phe Glu Leu Phe Ile Asp Glu Asn Ser Gly Phe Ala Lys Gly Val Leu
145                 150                 155                 160

Val Gln Lys Leu Gly Pro Trp Lys Arg Pro Val Ala Tyr Leu Ser Lys
            165                 170                 175

Lys Leu Asp Thr Val Ala Ser Gly Trp Pro Pro Cys Leu Arg Met Val
        180                 185                 190

Ala Ala Ile Ala Ile Leu Val Lys Asp Ala Gly Lys Leu Thr Leu Gly
            195                 200                 205

Gln Pro Leu Thr Ile Leu Thr Ser His Pro Val Glu Ala Leu Val Arg
210                 215                 220

Gln Pro Pro Asn Lys Trp Leu Ser Asn Ala Arg Met Thr His Tyr Gln
225                 230                 235                 240

Ala Met Leu Leu Asp Ala Glu Arg Val His Phe Gly Pro Thr Val Ser
            245                 250                 255

Leu Asn Pro Ala Thr Leu Leu Pro Leu Pro Ser Gly Lys Pro Pro Arg
            260                 265                 270

Leu Ser Pro Asp Leu Ala Glu Thr Met Ala Gln Thr Asp Leu Thr Asp
            275                 280                 285

Gln Pro Leu Pro Asp Ala Asp Leu Thr Trp Tyr Thr Xaa Gly Ser Ser
290                 295                 300

Xaa Ile Arg Asn Gly Glu Arg Lys Ala Gly Ala Val Thr Thr Glu
305                 310                 315                 320

Ser Glu Val Ile Trp Ala Ala Ser Leu Pro Pro Gly Thr Ser Ala Gln
            325                 330                 335

Arg Ala Glu Leu Ile Ala Leu Thr Gln Ala Leu Lys Met Ala Lys Gly
            340                 345                 350

Lys Lys Leu Thr Val Tyr Thr Asp Ser Arg Tyr Ala Phe Ala Thr Ala
            355                 360                 365

His Val Xaa Gly Glu Ile Tyr Arg Arg Arg Gly Xaa Leu Thr Ser Xaa
        370                 375                 380

Gly Lys Glu Ile Lys Asn Lys Asn Glu Ile Leu Ala Leu Leu Glu Ala
385                 390                 395                 400

Leu Phe Leu Pro Lys Arg Leu Ser Ile Ile Xaa Cys Pro Gly His Gln
            405                 410                 415

Lys Gly Asp Ser Pro Gln Ala Lys Gly Asn Arg Leu Ala Asp Asp Thr
            420                 425                 430

Ala Lys Lys Ala Ala Thr Glu Thr Gln Ser Ser Leu Thr Ile Leu
        435                 440                 445

<210> SEQ ID NO 11
<211> LENGTH: 447
<212> TYPE: PRT
<213> ORGANISM: Artificial Sequence
<220> FEATURE:
<223> OTHER INFORMATION: Synthetic construct

<400> SEQUENCE: 11

Tyr Val Asp Asp Leu Leu Leu Ala Ala Ala Thr Arg Thr Glu Cys Leu
1               5                   10                  15

Glu Gly Thr Lys Ala Leu Leu Glu Thr Leu Gly Asn Lys Gly Tyr Arg
            20                  25                  30

Ala Ser Ala Lys Lys Ala Gln Ile Cys Leu Gln Glu Val Thr Tyr Leu
        35                  40                  45

Gly Tyr Ser Leu Lys Asp Gly Gln Arg Trp Leu Thr Lys Ala Arg Lys
50                  55                  60
```

Glu Ala Ile Leu Ser Ile Pro Val Pro Lys Asn Pro Arg Gln Val Arg
65                  70                  75                  80

Glu Phe Leu Gly Thr Ala Gly Tyr Cys Arg Leu Trp Ile Pro Gly Phe
                85                  90                  95

Ala Glu Leu Ala Ala Pro Leu Tyr Pro Leu Thr Arg Pro Gly Thr Leu
            100                 105                 110

Phe Gln Trp Gly Thr Glu Gln Gln Leu Ala Phe Glu Asn Ile Arg Lys
        115                 120                 125

Ala Leu Leu Ser Ser Pro Ala Leu Gly Leu Pro Asp Ile Thr Lys Pro
130                 135                 140

Phe Glu Leu Phe Ile Asp Glu Asn Ser Gly Phe Ala Lys Gly Val Leu
145                 150                 155                 160

Val Gln Lys Leu Gly Pro Trp Lys Arg Pro Val Ala Tyr Leu Ser Lys
                165                 170                 175

Lys Leu Asp Thr Val Ala Ser Gly Trp Pro Pro Cys Leu Arg Met Val
            180                 185                 190

Ala Ala Ile Ala Ile Leu Val Lys Asp Ala Gly Lys Leu Thr Leu Gly
        195                 200                 205

Gln Pro Leu Thr Ile Leu Thr Ser His Pro Val Glu Ala Leu Val Arg
210                 215                 220

Gln Pro Pro Asn Lys Trp Leu Ser Asn Ala Arg Met Thr His Tyr Gln
225                 230                 235                 240

Ala Met Leu Leu Asp Ala Glu Arg Val His Phe Gly Pro Thr Val Ser
                245                 250                 255

Leu Asn Pro Ala Thr Leu Leu Pro Leu Pro Ser Gly Lys Pro Pro Arg
            260                 265                 270

Leu Ser Pro Asp Leu Ala Glu Thr Met Ala Gln Thr Asp Leu Thr Asp
        275                 280                 285

Gln Pro Leu Pro Asp Ala Asp Leu Thr Trp Tyr Thr Gly Gly Ser Ser
290                 295                 300

Phe Ile Arg Asn Gly Glu Arg Lys Ala Gly Ala Ala Val Thr Thr Glu
305                 310                 315                 320

Ser Glu Val Ile Trp Ala Ala Ser Leu Pro Pro Gly Thr Ser Ala Gln
                325                 330                 335

Arg Ala Glu Leu Ile Ala Leu Thr Gln Ala Leu Lys Met Ala Lys Gly
            340                 345                 350

Lys Lys Leu Thr Val Tyr Thr Asp Ser Arg Tyr Ala Phe Ala Thr Ala
        355                 360                 365

His Val His Gly Glu Ile Tyr Arg Arg Gly Trp Leu Thr Ser Lys
370                 375                 380

Gly Lys Glu Ile Lys Asn Lys Asn Glu Ile Leu Ala Leu Leu Glu Ala
385                 390                 395                 400

Leu Phe Leu Pro Lys Arg Leu Ser Ile Ile His Cys Pro Gly His Gln
                405                 410                 415

Lys Gly Asp Ser Pro Gln Ala Lys Gly Asn Arg Leu Ala Asp Asp Thr
            420                 425                 430

Ala Lys Lys Ala Ala Thr Glu Thr Gln Ser Ser Leu Thr Ile Leu
        435                 440                 445

<210> SEQ ID NO 12
<211> LENGTH: 447
<212> TYPE: PRT
<213> ORGANISM: Artificial Sequence
<220> FEATURE:

<223> OTHER INFORMATION: Synthetic construct

<400> SEQUENCE: 12

```
Tyr Val Asp Asp Leu Leu Ala Ala Ala Thr Arg Thr Glu Cys Leu
1               5                   10                  15

Glu Gly Thr Lys Ala Leu Leu Glu Thr Leu Gly Asn Lys Gly Tyr Arg
            20                  25                  30

Ala Ser Ala Lys Lys Ala Gln Ile Cys Leu Gln Glu Val Thr Tyr Leu
        35                  40                  45

Gly Tyr Ser Leu Lys Asp Gly Gln Arg Trp Leu Thr Lys Ala Arg Lys
    50                  55                  60

Glu Ala Ile Leu Ser Ile Pro Val Pro Lys Asn Pro Arg Gln Val Arg
65                  70                  75                  80

Glu Phe Leu Gly Thr Ala Gly Tyr Cys Arg Leu Trp Ile Pro Gly Phe
                85                  90                  95

Ala Glu Leu Ala Ala Pro Leu Tyr Pro Leu Thr Arg Pro Gly Thr Leu
            100                 105                 110

Phe Gln Trp Gly Thr Glu Gln Gln Leu Ala Phe Glu Asn Ile Arg Lys
        115                 120                 125

Ala Leu Leu Ser Ser Pro Ala Leu Gly Leu Pro Asp Ile Thr Lys Pro
    130                 135                 140

Phe Glu Leu Phe Ile Asp Glu Asn Ser Gly Phe Ala Lys Gly Val Leu
145                 150                 155                 160

Val Gln Lys Leu Gly Pro Trp Lys Arg Pro Val Ala Tyr Leu Ser Lys
                165                 170                 175

Lys Leu Asp Thr Val Ala Ser Gly Trp Pro Pro Cys Leu Arg Met Val
            180                 185                 190

Ala Ala Ile Ala Ile Leu Val Lys Asp Ala Gly Lys Leu Thr Leu Gly
        195                 200                 205

Gln Pro Leu Thr Ile Leu Thr Ser His Pro Val Glu Ala Leu Val Arg
    210                 215                 220

Gln Pro Pro Asn Lys Trp Leu Ser Asn Ala Arg Met Thr His Tyr Gln
225                 230                 235                 240

Ala Met Leu Leu Asp Ala Glu Arg Val His Phe Gly Pro Thr Val Ser
                245                 250                 255

Leu Asp Pro Ala Thr Leu Leu Pro Leu Pro Ser Gly Lys Pro Pro Arg
            260                 265                 270

Leu Ser Pro Asp Leu Ala Glu Thr Met Ala Gln Thr Asp Leu Thr Asp
    275                 280                 285

Gln Pro Leu Pro Asp Ala Asp Leu Thr Trp Tyr Thr Asp Gly Ser Ser
    290                 295                 300

Phe Ile Arg Asn Gly Glu Arg Lys Ala Gly Ala Ala Val Thr Thr Glu
305                 310                 315                 320

Ser Glu Val Ile Trp Ala Ala Ser Leu Pro Pro Gly Thr Ser Ala Gln
                325                 330                 335

Arg Ala Glu Leu Ile Ala Leu Thr Gln Ala Leu Lys Met Ala Lys Gly
            340                 345                 350

Lys Lys Leu Thr Val Tyr Thr Asp Ser Arg Tyr Ala Phe Ala Thr Ala
        355                 360                 365

His Val Lys Gly Glu Ile Tyr Arg Arg Arg Gly Trp Leu Thr Ser Glu
    370                 375                 380

Gly Lys Glu Ile Lys Asn Lys Asn Glu Ile Leu Ala Leu Leu Glu Ala
385                 390                 395                 400
```

```
Leu Phe Leu Pro Lys Arg Leu Ser Ile Ile His Cys Pro Gly His Gln
                405                 410                 415

Lys Gly Asp Ser Pro Gln Ala Lys Gly Asn Arg Leu Ala Asp Asp Thr
            420                 425                 430

Ala Lys Lys Ala Ala Thr Glu Thr Gln Ser Ser Leu Thr Ile Leu
        435                 440                 445

<210> SEQ ID NO 13
<211> LENGTH: 447
<212> TYPE: PRT
<213> ORGANISM: Artificial Sequence
<220> FEATURE:
<223> OTHER INFORMATION: Synthetic construct

<400> SEQUENCE: 13

Tyr Val Asp Asp Leu Leu Ala Ala Ala Thr Arg Thr Glu Cys Leu
1               5                   10                  15

Glu Gly Thr Lys Ala Leu Leu Glu Thr Leu Gly Asn Lys Gly Tyr Arg
            20                  25                  30

Ala Ser Ala Lys Lys Ala Gln Ile Cys Leu Gln Glu Val Thr Tyr Leu
        35                  40                  45

Gly Tyr Ser Leu Lys Asp Gly Gln Arg Trp Leu Thr Lys Ala Arg Lys
    50                  55                  60

Glu Ala Ile Leu Ser Ile Pro Val Pro Lys Asn Pro Arg Gln Val Arg
65                  70                  75                  80

Glu Phe Leu Gly Thr Ala Gly Tyr Cys Arg Leu Trp Ile Pro Gly Phe
                85                  90                  95

Ala Glu Leu Ala Ala Pro Leu Tyr Pro Leu Thr Arg Pro Gly Thr Leu
            100                 105                 110

Phe Gln Trp Gly Thr Glu Gln Gln Leu Ala Phe Glu Asn Ile Arg Lys
        115                 120                 125

Ala Leu Leu Ser Ser Pro Ala Leu Gly Leu Pro Asp Ile Thr Lys Pro
    130                 135                 140

Phe Glu Leu Phe Ile Asp Glu Asn Ser Gly Phe Ala Lys Gly Val Leu
145                 150                 155                 160

Val Gln Lys Leu Gly Pro Trp Lys Arg Pro Val Ala Tyr Leu Ser Lys
                165                 170                 175

Lys Leu Asp Thr Val Ala Ser Gly Trp Pro Pro Cys Leu Arg Met Val
            180                 185                 190

Ala Ala Ile Ala Ile Leu Val Lys Asp Ala Gly Lys Leu Thr Leu Gly
        195                 200                 205

Gln Pro Leu Thr Ile Leu Thr Ser His Pro Val Glu Ala Leu Val Arg
    210                 215                 220

Gln Pro Pro Asn Lys Trp Leu Ser Asn Ala Arg Met Thr His Tyr Gln
225                 230                 235                 240

Ala Met Leu Leu Asp Ala Glu Arg Val His Phe Gly Pro Thr Val Ser
                245                 250                 255

Leu Asn Pro Ala Thr Leu Leu Pro Leu Pro Ser Gly Lys Pro Pro Arg
            260                 265                 270

Leu Ser Pro Asp Leu Ala Glu Thr Met Ala Gln Thr Asp Leu Thr Asp
        275                 280                 285

Gln Pro Leu Pro Asp Ala Asp Leu Thr Trp Tyr Thr Gly Gly Ser Ser
    290                 295                 300

Phe Ile Arg Asn Gly Glu Arg Lys Ala Gly Ala Ala Val Thr Thr Glu
305                 310                 315                 320
```

Ser Glu Val Ile Trp Ala Ala Ser Leu Pro Pro Gly Thr Ser Ala Gln
                325                 330                 335

Arg Ala Glu Leu Ile Ala Leu Thr Gln Ala Leu Lys Met Ala Lys Gly
            340                 345                 350

Lys Lys Leu Thr Val Tyr Thr Asp Ser Arg Tyr Ala Phe Ala Thr Ala
        355                 360                 365

His Val His Gly Glu Ile Tyr Arg Arg Gly Trp Leu Thr Ser Glu
    370                 375                 380

Gly Lys Glu Ile Lys Asn Lys Asn Glu Ile Leu Ala Leu Leu Glu Ala
385                 390                 395                 400

Leu Phe Leu Pro Lys Arg Leu Ser Ile Ile His Cys Pro Gly His Gln
                405                 410                 415

Lys Gly Asp Ser Pro Gln Ala Lys Gly Asn Arg Leu Ala Asn Asp Thr
            420                 425                 430

Ala Lys Lys Ala Ala Thr Glu Thr Gln Ser Ser Leu Thr Ile Leu
        435                 440                 445

<210> SEQ ID NO 14
<211> LENGTH: 669
<212> TYPE: PRT
<213> ORGANISM: Artificial Sequence
<220> FEATURE:
<223> OTHER INFORMATION: Synthetic construct

<400> SEQUENCE: 14

Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asn Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

```
Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Lys Ala Arg Lys Glu Ala
        275                 280                 285

Ile Leu Ser Ile Pro Val Pro Lys Asn Pro Arg Gln Val Arg Glu Phe
    290                 295                 300

Leu Gly Thr Ala Gly Tyr Cys Arg Leu Trp Ile Pro Gly Phe Ala Glu
305                 310                 315                 320

Leu Ala Ala Pro Leu Tyr Pro Leu Thr Arg Pro Gly Thr Leu Phe Gln
                325                 330                 335

Trp Gly Thr Glu Gln Gln Leu Ala Phe Glu Asn Ile Arg Lys Ala Leu
            340                 345                 350

Leu Ser Ser Pro Ala Leu Gly Leu Pro Asp Ile Thr Lys Pro Phe Glu
        355                 360                 365

Leu Phe Ile Asp Glu Asn Ser Gly Phe Ala Lys Gly Val Leu Val Gln
    370                 375                 380

Lys Leu Gly Pro Trp Lys Arg Pro Val Ala Tyr Leu Ser Lys Lys Leu
385                 390                 395                 400

Asp Thr Val Ala Ser Gly Trp Pro Pro Cys Leu Arg Met Val Ala Ala
                405                 410                 415

Ile Ala Ile Leu Val Lys Asp Ala Gly Lys Leu Thr Leu Gly Gln Pro
            420                 425                 430

Leu Thr Ile Leu Thr Ser His Pro Val Glu Ala Leu Val Arg Gln Pro
        435                 440                 445

Pro Asn Lys Trp Leu Ser Asn Ala Arg Met Thr His Tyr Gln Ala Met
    450                 455                 460

Leu Leu Asp Ala Glu Arg Val His Phe Gly Pro Thr Val Ser Leu Asn
465                 470                 475                 480

Pro Ala Thr Leu Leu Pro Leu Pro Ser Gly Lys Pro Pro Arg Leu Ser
                485                 490                 495

Pro Asp Leu Ala Glu Thr Met Ala Gln Thr Asp Leu Thr Asp Gln Pro
            500                 505                 510

Leu Pro Asp Ala Asp Leu Thr Trp Tyr Thr Ala Gly Ser Ser Ile Ile
        515                 520                 525

Arg Asn Gly Glu Arg Lys Ala Gly Ala Ala Val Thr Thr Glu Ser Glu
    530                 535                 540

Val Ile Trp Ala Ala Ser Leu Pro Pro Gly Thr Ser Ala Gln Arg Ala
545                 550                 555                 560

Glu Leu Ile Ala Leu Thr Gln Ala Leu Lys Met Ala Lys Gly Lys Lys
                565                 570                 575

Leu Thr Val Tyr Thr Asp Ser Arg Tyr Ala Phe Ala Thr Ala His Val
            580                 585                 590

His Gly Glu Ile Tyr Arg Arg Arg Gly Leu Leu Thr Ser Glu Gly Lys
        595                 600                 605

Glu Ile Lys Asn Lys Asn Glu Ile Leu Ala Leu Leu Glu Ala Leu Phe
    610                 615                 620

Leu Pro Lys Arg Leu Ser Ile Ile Tyr Cys Pro Gly His Gln Lys Gly
625                 630                 635                 640

Asp Ser Pro Gln Ala Lys Gly Asn Arg Leu Ala Asp Asp Thr Ala Lys
                645                 650                 655

Lys Ala Ala Thr Glu Thr Gln Ser Ser Leu Thr Ile Leu
```

-continued

<210> SEQ ID NO 15
<211> LENGTH: 684
<212> TYPE: PRT
<213> ORGANISM: Artificial Sequence
<220> FEATURE:
<223> OTHER INFORMATION: Synthetic construct

<400> SEQUENCE: 15

Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Pro Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asn Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Lys Ala Arg Lys Glu Ala
        275                 280                 285

Ile Leu Ser Ile Pro Val Pro Lys Asn Pro Arg Gln Val Arg Glu Phe
    290                 295                 300

Leu Gly Thr Ala Gly Tyr Cys Arg Leu Trp Ile Pro Gly Phe Ala Glu
305                 310                 315                 320

Leu Ala Ala Pro Leu Tyr Pro Leu Thr Arg Pro Gly Thr Leu Phe Gln
                325                 330                 335

Trp Gly Thr Glu Gln Gln Leu Ala Phe Glu Asn Ile Arg Lys Ala Leu
            340                 345                 350

Leu Ser Ser Pro Ala Leu Gly Leu Pro Asp Ile Thr Lys Pro Phe Glu

```
                355                 360                 365
Leu Phe Ile Asp Glu Asn Ser Gly Phe Ala Lys Gly Val Leu Val Gln
        370                 375                 380
Lys Leu Gly Pro Trp Lys Arg Pro Val Ala Tyr Leu Ser Lys Lys Leu
385                 390                 395                 400
Asp Thr Val Ala Ser Gly Trp Pro Pro Cys Leu Arg Met Val Ala Ala
                405                 410                 415
Ile Ala Ile Leu Val Lys Asp Ala Gly Lys Leu Thr Leu Gly Gln Pro
            420                 425                 430
Leu Thr Ile Leu Thr Ser His Pro Val Glu Ala Leu Val Arg Gln Pro
        435                 440                 445
Pro Asn Lys Trp Leu Ser Asn Ala Arg Met Thr His Tyr Gln Ala Met
450                 455                 460
Leu Leu Asp Ala Glu Arg Val His Phe Gly Pro Thr Val Ser Leu Asn
465                 470                 475                 480
Pro Ala Thr Leu Leu Pro Leu Pro Ser Gly Lys Pro Pro Arg Leu Ser
                485                 490                 495
Pro Asp Leu Ala Glu Thr Met Ala Gln Thr Asp Leu Thr Asp Gln Pro
            500                 505                 510
Leu Pro Asp Ala Asp Leu Thr Trp Tyr Thr Gly Gly Ser Ser Phe Ile
        515                 520                 525
Arg Asn Gly Glu Arg Lys Ala Gly Ala Ala Val Thr Thr Glu Ser Glu
530                 535                 540
Val Ile Trp Ala Ala Ser Leu Pro Pro Gly Thr Ser Ala Gln Arg Ala
545                 550                 555                 560
Glu Leu Ile Ala Leu Thr Gln Ala Leu Lys Met Ala Lys Gly Lys Lys
                565                 570                 575
Leu Thr Val Tyr Thr Asp Ser Arg Tyr Ala Phe Ala Thr Ala His Val
            580                 585                 590
His Gly Glu Ile Tyr Arg Arg Arg Gly Trp Leu Thr Ser Lys Gly Lys
        595                 600                 605
Glu Ile Lys Asn Lys Asn Glu Ile Leu Ala Leu Leu Glu Ala Leu Phe
610                 615                 620
Leu Pro Lys Arg Leu Ser Ile Ile His Cys Pro Gly His Gln Lys Gly
625                 630                 635                 640
Asp Ser Pro Gln Ala Lys Gly Asn Arg Leu Ala Asp Asp Thr Ala Lys
                645                 650                 655
Lys Ala Ala Thr Glu Thr Gln Ser Ser Leu Thr Ile Leu Pro Thr Glu
            660                 665                 670
Leu Ile Glu Gly Pro Lys Arg Pro Pro Trp Glu Tyr
        675                 680

<210> SEQ ID NO 16
<211> LENGTH: 669
<212> TYPE: PRT
<213> ORGANISM: Artificial Sequence
<220> FEATURE:
<223> OTHER INFORMATION: Synthetic construct

<400> SEQUENCE: 16

Met Thr Leu Asn Ile Glu Asp Glu Tyr Arg Leu His Glu Thr Ser Lys
1               5                   10                  15
Glu Pro Asp Val Ser Leu Gly Ser Thr Trp Leu Ser Asp Phe Pro Gln
            20                  25                  30
Ala Trp Ala Glu Thr Gly Gly Met Gly Leu Ala Val Arg Gln Ala Pro
```

```
                  35                  40                  45
Leu Ile Ile Pro Leu Lys Ala Thr Ser Thr Pro Val Ser Ile Lys Gln
 50                  55                  60

Tyr Pro Met Ser Gln Glu Ala Arg Leu Gly Ile Lys Pro His Ile Gln
 65                  70                  75                  80

Arg Leu Leu Asp Gln Gly Ile Leu Val Pro Cys Gln Ser Pro Trp Asn
                     85                  90                  95

Thr Pro Leu Leu Pro Val Lys Lys Pro Gly Thr Asn Asp Tyr Arg Pro
                    100                 105                 110

Val Gln Asp Leu Arg Glu Val Asn Lys Arg Val Glu Asp Ile His Pro
                115                 120                 125

Thr Val Pro Asn Pro Tyr Asn Leu Leu Ser Gly Pro Pro Ser His
130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
                180                 185                 190

Phe Lys Asn Ser Pro Thr Leu Phe Asn Glu Ala Leu His Arg Asp Leu
                195                 200                 205

Ala Asp Phe Arg Ile Gln His Pro Asp Leu Ile Leu Leu Gln Tyr Val
210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
                260                 265                 270

Leu Leu Lys Glu Gly Gln Arg Trp Leu Thr Lys Ala Arg Lys Glu Ala
                275                 280                 285

Ile Leu Ser Ile Pro Val Pro Lys Asn Pro Arg Gln Val Arg Glu Phe
290                 295                 300

Leu Gly Thr Ala Gly Tyr Cys Arg Leu Trp Ile Pro Gly Phe Ala Glu
305                 310                 315                 320

Leu Ala Ala Pro Leu Tyr Pro Leu Thr Arg Pro Gly Thr Leu Phe Gln
                325                 330                 335

Trp Gly Thr Glu Gln Gln Leu Ala Phe Glu Asn Ile Arg Lys Ala Leu
                340                 345                 350

Leu Ser Ser Pro Ala Leu Gly Leu Pro Asp Ile Thr Lys Pro Phe Glu
                355                 360                 365

Leu Phe Ile Asp Glu Asn Ser Gly Phe Ala Lys Gly Val Leu Val Gln
                370                 375                 380

Lys Leu Gly Pro Trp Lys Arg Pro Val Ala Tyr Leu Ser Lys Lys Leu
385                 390                 395                 400

Asp Thr Val Ala Ser Gly Trp Pro Pro Cys Leu Arg Met Val Ala Ala
                405                 410                 415

Ile Ala Ile Leu Val Lys Asp Ala Gly Lys Leu Thr Leu Gly Gln Pro
                420                 425                 430

Leu Thr Ile Leu Thr Ser His Pro Val Glu Ala Leu Val Arg Gln Pro
                435                 440                 445

Pro Asn Lys Trp Leu Ser Asn Ala Arg Met Thr His Tyr Gln Ala Met
450                 455                 460
```

-continued

Leu Leu Asp Ala Glu Arg Val His Phe Gly Pro Thr Val Ser Leu Asn
465                 470                 475                 480

Pro Ala Thr Leu Leu Pro Leu Pro Ser Gly Lys Pro Pro Arg Leu Ser
                485                 490                 495

Pro Asp Leu Ala Glu Thr Met Ala Gln Thr Asp Leu Thr Asp Gln Pro
            500                 505                 510

Leu Pro Asp Ala Asp Leu Thr Trp Tyr Thr Gly Gly Ser Ser Phe Ile
        515                 520                 525

Arg Asn Gly Glu Arg Lys Ala Gly Ala Ala Val Thr Thr Glu Ser Glu
    530                 535                 540

Val Ile Trp Ala Ala Ser Leu Pro Pro Gly Thr Ser Ala Gln Arg Ala
545                 550                 555                 560

Glu Leu Ile Ala Leu Thr Gln Ala Leu Lys Met Ala Lys Gly Lys Lys
                565                 570                 575

Leu Thr Val Tyr Thr Asp Ser Arg Tyr Ala Phe Ala Thr Ala His Val
            580                 585                 590

His Gly Glu Ile Tyr Arg Arg Gly Trp Leu Thr Ser Lys Gly Lys
        595                 600                 605

Glu Ile Lys Asn Lys Asn Glu Ile Leu Ala Leu Glu Ala Leu Phe
    610                 615                 620

Leu Pro Lys Arg Leu Ser Ile Ile His Cys Pro Gly His Gln Lys Gly
625                 630                 635                 640

Asp Ser Pro Gln Ala Lys Gly Asn Arg Leu Ala Asp Asp Thr Ala Lys
                645                 650                 655

Lys Ala Ala Thr Glu Thr Gln Ser Ser Leu Thr Ile Leu
            660                 665

<210> SEQ ID NO 17
<211> LENGTH: 669
<212> TYPE: PRT
<213> ORGANISM: Artificial Sequence
<220> FEATURE:
<223> OTHER INFORMATION: Synthetic construct

<400> SEQUENCE: 17

Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
                20                  25                  30

Ala Trp Ala Glu Thr Gly Gly Met Gly Leu Ala Val Arg Gln Ala Pro
            35                  40                  45

Leu Ile Ile Pro Leu Lys Ala Thr Ser Thr Pro Val Ser Ile Lys Gln
50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Pro Pro Ser His
    130                 135                 140

Gln Trp Tyr Thr Val Leu Asp Leu Lys Asp Ala Phe Phe Cys Leu Arg
145                 150                 155                 160

```
Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asn Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Arg Thr Glu Cys Leu Glu Gly
225                 230                 235                 240

Thr Lys Ala Leu Leu Glu Thr Leu Gly Asn Lys Gly Tyr Arg Ala Ser
                245                 250                 255

Ala Lys Lys Ala Gln Ile Cys Leu Gln Glu Val Thr Tyr Leu Gly Tyr
            260                 265                 270

Ser Leu Lys Asp Gly Gln Arg Trp Leu Thr Lys Ala Arg Lys Glu Ala
        275                 280                 285

Ile Leu Ser Ile Pro Val Pro Lys Asn Pro Arg Gln Val Arg Glu Phe
    290                 295                 300

Leu Gly Thr Ala Gly Tyr Cys Arg Leu Trp Ile Pro Gly Phe Ala Glu
305                 310                 315                 320

Leu Ala Ala Pro Leu Tyr Pro Leu Thr Arg Pro Gly Thr Leu Phe Gln
                325                 330                 335

Trp Gly Thr Glu Gln Gln Leu Ala Phe Glu Asn Ile Arg Lys Ala Leu
            340                 345                 350

Leu Ser Ser Pro Ala Leu Gly Leu Pro Asp Ile Thr Lys Pro Phe Glu
        355                 360                 365

Leu Phe Ile Asp Glu Asn Ser Gly Phe Ala Lys Gly Val Leu Val Gln
    370                 375                 380

Lys Leu Gly Pro Trp Lys Arg Pro Val Ala Tyr Leu Ser Lys Lys Leu
385                 390                 395                 400

Asp Thr Val Ala Ser Gly Trp Pro Pro Cys Leu Arg Met Val Ala Ala
                405                 410                 415

Ile Ala Ile Leu Val Lys Asp Ala Gly Lys Leu Thr Leu Gly Gln Pro
            420                 425                 430

Leu Thr Ile Leu Thr Ser His Pro Val Glu Ala Leu Val Arg Gln Pro
        435                 440                 445

Pro Asn Lys Trp Leu Ser Asn Ala Arg Met Thr His Tyr Gln Ala Met
    450                 455                 460

Leu Leu Asp Ala Glu Arg Val His Phe Gly Pro Thr Val Ser Leu Asn
465                 470                 475                 480

Pro Ala Thr Leu Leu Pro Leu Pro Ser Gly Lys Pro Pro Arg Leu Ser
                485                 490                 495

Pro Asp Leu Ala Glu Thr Met Ala Gln Thr Asp Leu Thr Asp Gln Pro
            500                 505                 510

Leu Pro Asp Ala Asp Leu Thr Trp Tyr Thr Gly Gly Ser Ser Phe Ile
        515                 520                 525

Arg Asn Gly Glu Arg Lys Ala Gly Ala Ala Val Thr Thr Glu Ser Glu
    530                 535                 540

Val Ile Trp Ala Ala Ser Leu Pro Pro Gly Thr Ser Ala Gln Arg Ala
545                 550                 555                 560

Glu Leu Ile Ala Leu Thr Gln Ala Leu Lys Met Ala Lys Gly Lys Lys
                565                 570                 575
```

```
Leu Thr Val Tyr Thr Asp Ser Arg Tyr Ala Phe Ala Thr Ala His Val
            580                 585                 590

His Gly Glu Ile Tyr Arg Arg Gly Trp Leu Thr Ser Lys Gly Lys
        595                 600                 605

Glu Ile Lys Asn Lys Asn Glu Ile Leu Ala Leu Leu Glu Ala Leu Phe
        610                 615                 620

Leu Pro Lys Arg Leu Ser Ile Ile His Cys Pro Gly His Gln Lys Gly
625                 630                 635                 640

Asp Ser Pro Gln Ala Lys Gly Asn Arg Leu Ala Asp Thr Ala Lys
            645                 650                 655

Lys Ala Ala Thr Glu Thr Gln Ser Ser Leu Thr Ile Leu
            660                 665
```

<210> SEQ ID NO 18
<211> LENGTH: 669
<212> TYPE: PRT
<213> ORGANISM: Artificial Sequence
<220> FEATURE:
<223> OTHER INFORMATION: Synthetic construct

<400> SEQUENCE: 18

```
Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
            85                  90                  95

Thr Pro Leu Leu Pro Val Lys Lys Pro Gly Thr Asn Asp Tyr Arg Pro
        100                 105                 110

Val Gln Asp Leu Arg Glu Val Asn Lys Arg Val Glu Asp Ile His Pro
    115                 120                 125

Thr Val Pro Asn Pro Tyr Asn Leu Leu Ser Gly Leu Pro Pro Ser His
130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
            165                 170                 175

Glu Met Gly Ile Ser Gly Gln Leu Thr Trp Thr Arg Leu Pro Gln Gly
        180                 185                 190

Phe Lys Asn Ser Pro Thr Leu Phe Asn Glu Ala Leu His Arg Asp Leu
    195                 200                 205

Ala Asp Phe Arg Ile Gln His Pro Asp Leu Ile Leu Leu Gln Tyr Val
    210                 215                 220

Asp Asp Leu Leu Leu Ala Ala Ala Thr Arg Thr Glu Cys Leu Glu Gly
225                 230                 235                 240

Thr Lys Ala Leu Leu Glu Thr Leu Gly Asn Lys Gly Tyr Arg Ala Ser
            245                 250                 255

Ala Lys Lys Ala Gln Ile Cys Leu Gln Glu Val Thr Tyr Leu Gly Tyr
        260                 265                 270
```

Ser Leu Lys Asp Gly Gln Arg Trp Leu Thr Lys Ala Arg Lys Glu Ala
            275                 280                 285

Ile Leu Ser Ile Pro Val Pro Lys Asn Pro Arg Gln Val Arg Glu Phe
        290                 295                 300

Leu Gly Thr Ala Gly Tyr Cys Arg Leu Trp Ile Pro Gly Phe Ala Glu
305                 310                 315                 320

Leu Ala Ala Pro Leu Tyr Pro Leu Thr Arg Pro Gly Thr Leu Phe Gln
                325                 330                 335

Trp Gly Thr Glu Gln Gln Leu Ala Phe Glu Asn Ile Arg Lys Ala Leu
            340                 345                 350

Leu Ser Ser Pro Ala Leu Gly Leu Pro Asp Ile Thr Lys Pro Phe Glu
        355                 360                 365

Leu Phe Ile Asp Glu Asn Ser Gly Phe Ala Lys Gly Val Leu Val Gln
        370                 375                 380

Lys Leu Gly Pro Trp Lys Arg Pro Val Ala Tyr Leu Ser Lys Lys Leu
385                 390                 395                 400

Asp Thr Val Ala Ser Gly Trp Pro Pro Cys Leu Arg Met Val Ala Ala
                405                 410                 415

Ile Ala Ile Leu Val Lys Asp Ala Gly Lys Leu Thr Leu Gly Gln Pro
            420                 425                 430

Leu Thr Ile Leu Thr Ser His Pro Val Glu Ala Leu Val Arg Gln Pro
        435                 440                 445

Pro Asn Lys Trp Leu Ser Asn Ala Arg Met Thr His Tyr Gln Ala Met
        450                 455                 460

Leu Leu Asp Ala Glu Arg Val His Phe Gly Pro Thr Val Ser Leu Asp
465                 470                 475                 480

Pro Ala Thr Leu Leu Pro Leu Pro Ser Gly Lys Pro Arg Leu Ser
                485                 490                 495

Pro Asp Leu Ala Glu Thr Met Ala Gln Thr Asp Leu Thr Asp Gln Pro
            500                 505                 510

Leu Pro Asp Ala Asp Leu Thr Trp Tyr Thr Asp Gly Ser Ser Phe Ile
        515                 520                 525

Arg Asn Gly Glu Arg Lys Ala Gly Ala Ala Val Thr Thr Glu Ser Glu
530                 535                 540

Val Ile Trp Ala Ala Ser Leu Pro Pro Gly Thr Ser Ala Gln Arg Ala
545                 550                 555                 560

Glu Leu Ile Ala Leu Thr Gln Ala Leu Lys Met Ala Lys Gly Lys Lys
                565                 570                 575

Leu Thr Val Tyr Thr Asp Ser Arg Tyr Ala Phe Ala Thr Ala His Val
            580                 585                 590

Lys Gly Glu Ile Tyr Arg Arg Arg Gly Trp Leu Thr Ser Glu Gly Lys
        595                 600                 605

Glu Ile Lys Asn Lys Asn Glu Ile Leu Ala Leu Leu Glu Ala Leu Phe
        610                 615                 620

Leu Pro Lys Arg Leu Ser Ile Ile His Cys Pro Gly His Gln Lys Gly
625                 630                 635                 640

Asp Ser Pro Gln Ala Lys Gly Asn Arg Leu Ala Asp Asp Thr Ala Lys
                645                 650                 655

Lys Ala Ala Thr Glu Thr Gln Ser Ser Leu Thr Ile Leu
            660                 665

<210> SEQ ID NO 19
<211> LENGTH: 447
<212> TYPE: PRT

<213> ORGANISM: Artificial Sequence
<220> FEATURE:
<223> OTHER INFORMATION: Synthetic construct

<400> SEQUENCE: 19

```
Tyr Val Asp Asp Leu Leu Ala Ala Thr Arg Thr Glu Cys Leu
1               5                   10                  15

Glu Gly Thr Lys Ala Leu Leu Glu Thr Leu Gly Asn Lys Gly Tyr Arg
            20                  25                  30

Ala Ser Ala Lys Lys Ala Gln Ile Cys Leu Gln Glu Val Thr Tyr Leu
        35                  40                  45

Gly Tyr Ser Leu Lys Asp Gly Gln Arg Trp Leu Thr Lys Ala Arg Lys
    50                  55                  60

Glu Ala Ile Leu Ser Ile Pro Val Pro Lys Asn Pro Arg Gln Val Arg
65                  70                  75                  80

Glu Phe Leu Gly Thr Ala Gly Tyr Cys Arg Leu Trp Ile Pro Gly Phe
                85                  90                  95

Ala Glu Leu Ala Ala Pro Leu Tyr Pro Leu Thr Arg Pro Gly Thr Leu
            100                 105                 110

Phe Gln Trp Gly Thr Glu Gln Gln Leu Ala Phe Glu Asn Ile Arg Lys
        115                 120                 125

Ala Leu Leu Ser Ser Pro Ala Leu Gly Leu Pro Asp Ile Thr Lys Pro
    130                 135                 140

Phe Glu Leu Phe Ile Asp Glu Asn Ser Gly Phe Ala Lys Gly Val Leu
145                 150                 155                 160

Val Gln Lys Leu Gly Pro Trp Lys Arg Pro Val Ala Tyr Leu Ser Lys
                165                 170                 175

Lys Leu Asp Thr Val Ala Ser Gly Trp Pro Pro Cys Leu Arg Met Val
            180                 185                 190

Ala Ala Ile Ala Ile Leu Val Lys Asp Ala Gly Lys Leu Thr Leu Gly
        195                 200                 205

Gln Pro Leu Thr Ile Leu Thr Ser His Pro Val Glu Ala Leu Val Arg
    210                 215                 220

Gln Pro Pro Asn Lys Trp Leu Ser Asn Ala Arg Met Thr His Tyr Gln
225                 230                 235                 240

Ala Met Leu Leu Asp Ala Glu Arg Val His Phe Gly Pro Thr Val Ser
                245                 250                 255

Leu Asn Pro Ala Thr Leu Leu Pro Leu Pro Ser Gly Lys Pro Pro Arg
            260                 265                 270

Leu Ser Pro Asp Leu Ala Glu Thr Met Ala Gln Thr Asp Leu Thr Asp
        275                 280                 285

Gln Pro Leu Pro Asp Ala Asp Leu Thr Trp Tyr Thr Gly Gly Ser Ser
    290                 295                 300

Phe Ile Arg Asn Gly Glu Arg Lys Ala Gly Ala Ala Val Thr Thr Glu
305                 310                 315                 320

Ser Glu Val Ile Trp Ala Ala Ser Leu Pro Pro Gly Thr Ser Ala Gln
                325                 330                 335

Arg Ala Glu Leu Ile Ala Leu Thr Gln Ala Leu Lys Met Ala Lys Gly
            340                 345                 350

Lys Lys Leu Thr Val Tyr Thr Asp Ser Arg Tyr Ala Phe Ala Thr Ala
        355                 360                 365

His Val His Gly Glu Ile Tyr Arg Arg Arg Gly Trp Leu Thr Ser Glu
    370                 375                 380

Gly Lys Glu Ile Lys Asn Lys Asn Glu Ile Leu Ala Leu Leu Glu Ala
```

```
385                 390                 395                 400
Leu Phe Leu Pro Lys Arg Leu Ser Ile Ile His Cys Pro Gly His Gln
                405                 410                 415

Lys Gly Asp Ser Pro Gln Ala Lys Gly Asn Arg Leu Ala Asn Asp Thr
                420                 425                 430

Ala Lys Lys Ala Ala Thr Glu Thr Gln Ser Ser Leu Thr Ile Leu
                435                 440                 445

<210> SEQ ID NO 20
<211> LENGTH: 692
<212> TYPE: PRT
<213> ORGANISM: Artificial Sequence
<220> FEATURE:
<223> OTHER INFORMATION: Synthetic construct

<400> SEQUENCE: 20

Met Gly Ser Ser His His His His His His Ser Ser Gly Leu Val Pro
1               5                   10                  15

Arg Gly Ser His Met Thr Leu Asn Ile Glu Asp Glu Tyr Arg Leu His
                20                  25                  30

Glu Thr Ser Lys Glu Pro Asp Val Ser Leu Gly Ser Thr Trp Leu Ser
            35                  40                  45

Asp Phe Pro Gln Ala Trp Ala Glu Thr Gly Gly Met Gly Leu Ala Val
        50                  55                  60

Arg Gln Ala Pro Leu Ile Ile Pro Leu Lys Ala Thr Ser Thr Pro Val
65                  70                  75                  80

Ser Ile Lys Gln Tyr Pro Met Ser Gln Glu Ala Arg Leu Gly Ile Lys
                85                  90                  95

Pro His Ile Gln Arg Leu Leu Asp Gln Gly Ile Leu Val Pro Cys Gln
                100                 105                 110

Ser Pro Trp Asn Thr Pro Leu Leu Pro Val Lys Lys Pro Gly Thr Asn
            115                 120                 125

Asp Tyr Arg Pro Val Gln Asp Leu Arg Glu Val Asn Lys Arg Val Glu
        130                 135                 140

Asp Ile His Pro Thr Val Pro Asn Pro Tyr Asn Leu Leu Ser Gly Pro
145                 150                 155                 160

Pro Pro Ser His Gln Trp Tyr Thr Val Leu Asp Leu Lys Asp Ala Phe
                165                 170                 175

Phe Cys Leu Arg Leu His Pro Thr Ser Gln Pro Leu Phe Ala Phe Glu
                180                 185                 190

Trp Arg Asp Pro Glu Met Gly Ile Ser Gly Gln Leu Thr Trp Thr Arg
            195                 200                 205

Leu Pro Gln Gly Phe Lys Asn Ser Pro Thr Leu Phe Asn Glu Ala Leu
        210                 215                 220

His Arg Asp Leu Ala Asp Phe Arg Ile Gln His Pro Asp Leu Ile Leu
225                 230                 235                 240

Leu Gln Tyr Val Asp Asp Leu Leu Leu Ala Ala Thr Ser Glu Leu Asp
                245                 250                 255

Cys Gln Gln Gly Thr Arg Ala Leu Leu Gln Thr Leu Gly Asn Leu Gly
                260                 265                 270

Tyr Arg Ala Ser Ala Lys Lys Ala Gln Ile Cys Gln Lys Gln Val Lys
            275                 280                 285

Tyr Leu Gly Tyr Leu Leu Lys Glu Gly Gln Arg Trp Leu Thr Lys Ala
        290                 295                 300

Arg Lys Glu Ala Ile Leu Ser Ile Pro Val Pro Lys Asn Pro Arg Gln
```

```
            305                 310                 315                 320
Val Arg Glu Phe Leu Gly Thr Ala Gly Tyr Cys Arg Leu Trp Ile Pro
                325                 330                 335

Gly Phe Ala Glu Leu Ala Ala Pro Leu Tyr Pro Leu Thr Arg Pro Gly
                340                 345                 350

Thr Leu Phe Gln Trp Gly Thr Glu Gln Gln Leu Ala Phe Glu Asn Ile
                355                 360                 365

Arg Lys Ala Leu Leu Ser Ser Pro Ala Leu Gly Leu Pro Asp Ile Thr
370                 375                 380

Lys Pro Phe Glu Leu Phe Ile Asp Glu Asn Ser Gly Phe Ala Lys Gly
385                 390                 395                 400

Val Leu Val Gln Lys Leu Gly Pro Trp Lys Arg Pro Val Ala Tyr Leu
                405                 410                 415

Ser Lys Lys Leu Asp Thr Val Ala Ser Gly Trp Pro Pro Cys Leu Arg
                420                 425                 430

Met Val Ala Ala Ile Ala Ile Leu Val Lys Asp Ala Gly Lys Leu Thr
                435                 440                 445

Leu Gly Gln Pro Leu Thr Ile Leu Thr Ser His Pro Val Glu Ala Leu
450                 455                 460

Val Arg Gln Pro Pro Asn Lys Trp Leu Ser Asn Ala Arg Met Thr His
465                 470                 475                 480

Tyr Gln Ala Met Leu Leu Asp Ala Glu Arg Val His Phe Gly Pro Thr
                485                 490                 495

Val Ser Leu Asn Pro Ala Thr Leu Leu Pro Leu Pro Ser Gly Lys Pro
                500                 505                 510

Pro Arg Leu Ser Pro Asp Leu Ala Glu Thr Met Ala Gln Thr Asp Leu
                515                 520                 525

Thr Asp Gln Pro Leu Pro Asp Ala Asp Leu Thr Trp Tyr Thr Ala Gly
                530                 535                 540

Ser Ser Ile Ile Arg Asn Gly Glu Arg Lys Ala Gly Ala Ala Val Thr
545                 550                 555                 560

Thr Glu Ser Glu Val Ile Trp Ala Ala Ser Leu Pro Pro Gly Thr Ser
                565                 570                 575

Ala Gln Arg Ala Glu Leu Ile Ala Leu Thr Gln Ala Leu Lys Met Ala
                580                 585                 590

Lys Gly Lys Lys Leu Thr Val Tyr Thr Asp Ser Arg Tyr Ala Phe Ala
                595                 600                 605

Thr Ala His Val His Gly Glu Ile Tyr Arg Arg Arg Gly Leu Leu Thr
                610                 615                 620

Ser Glu Gly Lys Glu Ile Lys Asn Lys Asn Glu Ile Leu Ala Leu Leu
625                 630                 635                 640

Glu Ala Leu Phe Leu Pro Lys Arg Leu Ser Ile Ile Tyr Cys Pro Gly
                645                 650                 655

His Gln Lys Gly Asp Ser Pro Gln Ala Lys Gly Asn Arg Leu Ala Asp
                660                 665                 670

Asp Thr Ala Lys Lys Ala Ala Thr Glu Thr Gln Ser Ser Leu Thr Ile
                675                 680                 685

Leu Ala Ala Ala
        690

<210> SEQ ID NO 21
<211> LENGTH: 707
<212> TYPE: PRT
<213> ORGANISM: Artificial Sequence
```

<220> FEATURE:
<223> OTHER INFORMATION: Synthetic construct

<400> SEQUENCE: 21

```
Met Gly Ser Ser His His His His His Ser Ser Gly Leu Val Pro
1               5                   10                  15

Arg Gly Ser His Met Thr Leu Asn Ile Glu Asp Glu Tyr Arg Leu His
            20                  25                  30

Glu Thr Ser Lys Glu Pro Asp Val Ser Leu Gly Ser Thr Trp Leu Ser
                35                  40                  45

Asp Phe Pro Gln Ala Trp Ala Glu Thr Gly Gly Met Gly Leu Ala Val
        50                  55                  60

Arg Gln Ala Pro Leu Ile Ile Pro Leu Lys Ala Thr Ser Thr Pro Val
65                  70                  75                  80

Ser Ile Lys Gln Tyr Pro Met Ser Gln Glu Ala Arg Leu Gly Ile Lys
                85                  90                  95

Pro His Ile Gln Arg Leu Leu Asp Gln Gly Ile Leu Val Pro Cys Gln
            100                 105                 110

Ser Pro Trp Asn Thr Pro Leu Leu Pro Val Lys Lys Pro Gly Thr Asn
            115                 120                 125

Asp Tyr Arg Pro Val Gln Asp Leu Arg Glu Val Asn Lys Arg Val Glu
130                 135                 140

Asp Ile His Pro Thr Val Pro Asn Pro Tyr Asn Leu Leu Ser Gly Pro
145                 150                 155                 160

Pro Pro Ser His Gln Trp Tyr Thr Val Leu Asp Leu Lys Asp Ala Phe
            165                 170                 175

Phe Cys Leu Arg Leu His Pro Thr Ser Gln Pro Leu Phe Ala Phe Glu
            180                 185                 190

Trp Arg Asp Pro Glu Met Gly Ile Ser Gly Gln Leu Thr Trp Thr Arg
            195                 200                 205

Leu Pro Gln Gly Phe Lys Asn Ser Pro Thr Leu Phe Asn Glu Ala Leu
            210                 215                 220

His Arg Asp Leu Ala Asp Phe Arg Ile Gln His Pro Asp Leu Ile Leu
225                 230                 235                 240

Leu Gln Tyr Val Asp Asp Leu Leu Leu Ala Ala Thr Ser Glu Leu Asp
                245                 250                 255

Cys Gln Gln Gly Thr Arg Ala Leu Leu Gln Thr Leu Gly Asn Leu Gly
            260                 265                 270

Tyr Arg Ala Ser Ala Lys Lys Ala Gln Ile Cys Gln Lys Gln Val Lys
            275                 280                 285

Tyr Leu Gly Tyr Leu Leu Lys Glu Gly Gln Arg Trp Leu Thr Lys Ala
            290                 295                 300

Arg Lys Glu Ala Ile Leu Ser Ile Pro Val Pro Lys Asn Pro Arg Gln
305                 310                 315                 320

Val Arg Glu Phe Leu Gly Thr Ala Gly Tyr Cys Arg Leu Trp Ile Pro
            325                 330                 335

Gly Phe Ala Glu Leu Ala Ala Pro Leu Tyr Pro Leu Thr Arg Pro Gly
            340                 345                 350

Thr Leu Phe Gln Trp Gly Thr Glu Gln Gln Leu Ala Phe Glu Asn Ile
            355                 360                 365

Arg Lys Ala Leu Leu Ser Ser Pro Ala Leu Gly Leu Pro Asp Ile Thr
370                 375                 380

Lys Pro Phe Glu Leu Phe Ile Asp Glu Asn Ser Gly Phe Ala Lys Gly
385                 390                 395                 400
```

Val Leu Val Gln Lys Leu Gly Pro Trp Lys Arg Pro Val Ala Tyr Leu
            405                 410                 415

Ser Lys Lys Leu Asp Thr Val Ala Ser Gly Trp Pro Cys Leu Arg
        420                 425                 430

Met Val Ala Ala Ile Ala Ile Leu Val Lys Asp Ala Gly Lys Leu Thr
            435                 440                 445

Leu Gly Gln Pro Leu Thr Ile Leu Thr Ser His Pro Val Glu Ala Leu
        450                 455                 460

Val Arg Gln Pro Pro Asn Lys Trp Leu Ser Asn Ala Arg Met Thr His
465                 470                 475                 480

Tyr Gln Ala Met Leu Leu Asp Ala Glu Arg Val His Phe Gly Pro Thr
                485                 490                 495

Val Ser Leu Asn Pro Ala Thr Leu Leu Pro Leu Pro Ser Gly Lys Pro
            500                 505                 510

Pro Arg Leu Ser Pro Asp Leu Ala Glu Thr Met Ala Gln Thr Asp Leu
        515                 520                 525

Thr Asp Gln Pro Leu Pro Asp Ala Asp Leu Thr Trp Tyr Thr Gly Gly
    530                 535                 540

Ser Ser Phe Ile Arg Asn Gly Glu Arg Lys Ala Gly Ala Ala Val Thr
545                 550                 555                 560

Thr Glu Ser Glu Val Ile Trp Ala Ala Ser Leu Pro Pro Gly Thr Ser
                565                 570                 575

Ala Gln Arg Ala Glu Leu Ile Ala Leu Thr Gln Ala Leu Lys Met Ala
            580                 585                 590

Lys Gly Lys Lys Leu Thr Val Tyr Thr Asp Ser Arg Tyr Ala Phe Ala
        595                 600                 605

Thr Ala His Val His Gly Glu Ile Tyr Arg Arg Arg Gly Trp Leu Thr
    610                 615                 620

Ser Lys Gly Lys Glu Ile Lys Asn Lys Asn Glu Ile Leu Ala Leu Leu
625                 630                 635                 640

Glu Ala Leu Phe Leu Pro Lys Arg Leu Ser Ile Ile His Cys Pro Gly
                645                 650                 655

His Gln Lys Gly Asp Ser Pro Gln Ala Lys Gly Asn Arg Leu Ala Asp
            660                 665                 670

Asp Thr Ala Lys Lys Ala Ala Thr Glu Thr Gln Ser Ser Leu Thr Ile
        675                 680                 685

Leu Pro Thr Glu Leu Ile Glu Gly Pro Lys Arg Pro Pro Trp Glu Tyr
    690                 695                 700

Ala Ala Ala
705

<210> SEQ ID NO 22
<211> LENGTH: 692
<212> TYPE: PRT
<213> ORGANISM: Artificial Sequence
<220> FEATURE:
<223> OTHER INFORMATION: Synthetic construct

<400> SEQUENCE: 22

Met Gly Ser Ser His His His His His His Ser Ser Gly Leu Val Pro
1               5                   10                  15

Arg Gly Ser His Met Thr Leu Asn Ile Glu Asp Glu Tyr Arg Leu His
                20                  25                  30

Glu Thr Ser Lys Glu Pro Asp Val Ser Leu Gly Ser Thr Trp Leu Ser
        35                  40                  45

-continued

Asp Phe Pro Gln Ala Trp Ala Glu Thr Gly Gly Met Gly Leu Ala Val
 50                  55                  60

Arg Gln Ala Pro Leu Ile Ile Pro Leu Lys Ala Thr Ser Thr Pro Val
 65                  70                  75                  80

Ser Ile Lys Gln Tyr Pro Met Ser Gln Glu Ala Arg Leu Gly Ile Lys
                     85                  90                  95

Pro His Ile Gln Arg Leu Leu Asp Gln Gly Ile Leu Val Pro Cys Gln
                100                 105                 110

Ser Pro Trp Asn Thr Pro Leu Leu Pro Val Lys Lys Pro Gly Thr Asn
                115                 120                 125

Asp Tyr Arg Pro Val Gln Asp Leu Arg Glu Val Asn Lys Arg Val Glu
            130                 135                 140

Asp Ile His Pro Thr Val Pro Asn Pro Tyr Asn Leu Leu Ser Gly Pro
145                 150                 155                 160

Pro Pro Ser His Gln Trp Tyr Thr Val Leu Asp Leu Lys Asp Ala Phe
                    165                 170                 175

Phe Cys Leu Arg Leu His Pro Thr Ser Gln Pro Leu Phe Ala Phe Glu
                180                 185                 190

Trp Arg Asp Pro Glu Met Gly Ile Ser Gly Gln Leu Thr Trp Thr Arg
                195                 200                 205

Leu Pro Gln Gly Phe Lys Asn Ser Pro Thr Leu Phe Asn Glu Ala Leu
    210                 215                 220

His Arg Asp Leu Ala Asp Phe Arg Ile Gln His Pro Asp Leu Ile Leu
225                 230                 235                 240

Leu Gln Tyr Val Asp Asp Leu Leu Leu Ala Ala Thr Ser Glu Leu Asp
                245                 250                 255

Cys Gln Gln Gly Thr Arg Ala Leu Leu Gln Thr Leu Gly Asn Leu Gly
                260                 265                 270

Tyr Arg Ala Ser Ala Lys Lys Ala Gln Ile Cys Gln Lys Gln Val Lys
    275                 280                 285

Tyr Leu Gly Tyr Leu Leu Lys Glu Gly Gln Arg Trp Leu Thr Lys Ala
    290                 295                 300

Arg Lys Glu Ala Ile Leu Ser Ile Pro Val Pro Lys Asn Pro Arg Gln
305                 310                 315                 320

Val Arg Glu Phe Leu Gly Thr Ala Gly Tyr Cys Arg Leu Trp Ile Pro
                325                 330                 335

Gly Phe Ala Glu Leu Ala Ala Pro Leu Tyr Pro Leu Thr Arg Pro Gly
                340                 345                 350

Thr Leu Phe Gln Trp Gly Thr Glu Gln Gln Leu Ala Phe Glu Asn Ile
            355                 360                 365

Arg Lys Ala Leu Leu Ser Ser Pro Ala Leu Gly Leu Pro Asp Ile Thr
    370                 375                 380

Lys Pro Phe Glu Leu Phe Ile Asp Glu Asn Ser Gly Phe Ala Lys Gly
385                 390                 395                 400

Val Leu Val Gln Lys Leu Gly Pro Trp Lys Arg Pro Val Ala Tyr Leu
                405                 410                 415

Ser Lys Lys Leu Asp Thr Val Ala Ser Gly Trp Pro Pro Cys Leu Arg
                420                 425                 430

Met Val Ala Ala Ile Ala Ile Leu Val Lys Asp Ala Gly Lys Leu Thr
            435                 440                 445

Leu Gly Gln Pro Leu Thr Ile Leu Thr Ser His Pro Val Glu Ala Leu
    450                 455                 460

Val Arg Gln Pro Pro Asn Lys Trp Leu Ser Asn Ala Arg Met Thr His
465                 470                 475                 480

Tyr Gln Ala Met Leu Leu Asp Ala Glu Arg Val His Phe Gly Pro Thr
            485                 490                 495

Val Ser Leu Asn Pro Ala Thr Leu Leu Pro Leu Pro Ser Gly Lys Pro
        500                 505                 510

Pro Arg Leu Ser Pro Asp Leu Ala Glu Thr Met Ala Gln Thr Asp Leu
    515                 520                 525

Thr Asp Gln Pro Leu Pro Asp Ala Asp Leu Thr Trp Tyr Thr Gly Gly
530                 535                 540

Ser Ser Phe Ile Arg Asn Gly Glu Arg Lys Ala Gly Ala Ala Val Thr
545                 550                 555                 560

Thr Glu Ser Glu Val Ile Trp Ala Ala Ser Leu Pro Pro Gly Thr Ser
            565                 570                 575

Ala Gln Arg Ala Glu Leu Ile Ala Leu Thr Gln Ala Leu Lys Met Ala
        580                 585                 590

Lys Gly Lys Lys Leu Thr Val Tyr Thr Asp Ser Arg Tyr Ala Phe Ala
    595                 600                 605

Thr Ala His Val His Gly Glu Ile Tyr Arg Arg Arg Gly Trp Leu Thr
610                 615                 620

Ser Lys Gly Lys Glu Ile Lys Asn Lys Asn Glu Ile Leu Ala Leu Leu
625                 630                 635                 640

Glu Ala Leu Phe Leu Pro Lys Arg Leu Ser Ile Ile His Cys Pro Gly
            645                 650                 655

His Gln Lys Gly Asp Ser Pro Gln Ala Lys Gly Asn Arg Leu Ala Asp
        660                 665                 670

Asp Thr Ala Lys Lys Ala Ala Thr Glu Thr Gln Ser Ser Leu Thr Ile
    675                 680                 685

Leu Ala Ala Ala
    690

<210> SEQ ID NO 23
<211> LENGTH: 692
<212> TYPE: PRT
<213> ORGANISM: Artificial Sequence
<220> FEATURE:
<223> OTHER INFORMATION: Synthetic construct

<400> SEQUENCE: 23

Met Gly Ser Ser His His His His His His Ser Ser Gly Leu Val Pro
1               5                   10                  15

Arg Gly Ser His Met Thr Leu Asn Ile Glu Asp Glu Tyr Arg Leu His
            20                  25                  30

Glu Thr Ser Lys Glu Pro Asp Val Ser Leu Gly Ser Thr Trp Leu Ser
        35                  40                  45

Asp Phe Pro Gln Ala Trp Ala Glu Thr Gly Gly Met Gly Leu Ala Val
    50                  55                  60

Arg Gln Ala Pro Leu Ile Ile Pro Leu Lys Ala Thr Ser Thr Pro Val
65                  70                  75                  80

Ser Ile Lys Gln Tyr Pro Met Ser Gln Glu Ala Arg Leu Gly Ile Lys
            85                  90                  95

Pro His Ile Gln Arg Leu Leu Asp Gln Gly Ile Leu Val Pro Cys Gln
        100                 105                 110

Ser Pro Trp Asn Thr Pro Leu Leu Pro Val Lys Lys Pro Gly Thr Asn
    115                 120                 125

Asp Tyr Arg Pro Val Gln Asp Leu Arg Glu Val Asn Lys Arg Val Glu
130                 135                 140

Asp Ile His Pro Thr Val Pro Asn Pro Tyr Asn Leu Leu Ser Gly Pro
145                 150                 155                 160

Pro Pro Ser His Gln Trp Tyr Thr Val Leu Asp Leu Lys Asp Ala Phe
                165                 170                 175

Phe Cys Leu Arg Leu His Pro Thr Ser Gln Pro Leu Phe Ala Phe Glu
                180                 185                 190

Trp Arg Asp Pro Glu Met Gly Ile Ser Gly Gln Leu Thr Trp Thr Arg
                195                 200                 205

Leu Pro Gln Gly Phe Lys Asn Ser Pro Thr Leu Phe Asn Glu Ala Leu
210                 215                 220

His Arg Asp Leu Ala Asp Phe Arg Ile Gln His Pro Asp Leu Ile Leu
225                 230                 235                 240

Leu Gln Tyr Val Asp Asp Leu Leu Leu Ala Ala Thr Arg Thr Glu
                245                 250                 255

Cys Leu Glu Gly Thr Lys Ala Leu Leu Glu Thr Leu Gly Asn Lys Gly
                260                 265                 270

Tyr Arg Ala Ser Ala Lys Lys Ala Gln Ile Cys Leu Gln Glu Val Thr
                275                 280                 285

Tyr Leu Gly Tyr Ser Leu Lys Asp Gly Gln Arg Trp Leu Thr Lys Ala
290                 295                 300

Arg Lys Glu Ala Ile Leu Ser Ile Pro Val Pro Lys Asn Pro Arg Gln
305                 310                 315                 320

Val Arg Glu Phe Leu Gly Thr Ala Gly Tyr Cys Arg Leu Trp Ile Pro
                325                 330                 335

Gly Phe Ala Glu Leu Ala Ala Pro Leu Tyr Pro Leu Thr Arg Pro Gly
                340                 345                 350

Thr Leu Phe Gln Trp Gly Thr Glu Gln Gln Leu Ala Phe Glu Asn Ile
                355                 360                 365

Arg Lys Ala Leu Leu Ser Ser Pro Ala Leu Gly Leu Pro Asp Ile Thr
370                 375                 380

Lys Pro Phe Glu Leu Phe Ile Asp Glu Asn Ser Gly Phe Ala Lys Gly
385                 390                 395                 400

Val Leu Val Gln Lys Leu Gly Pro Trp Lys Arg Pro Val Ala Tyr Leu
                405                 410                 415

Ser Lys Lys Leu Asp Thr Val Ala Ser Gly Trp Pro Pro Cys Leu Arg
                420                 425                 430

Met Val Ala Ala Ile Ala Ile Leu Val Lys Asp Ala Gly Lys Leu Thr
                435                 440                 445

Leu Gly Gln Pro Leu Thr Ile Leu Thr Ser His Pro Val Glu Ala Leu
450                 455                 460

Val Arg Gln Pro Pro Asn Lys Trp Leu Ser Asn Ala Arg Met Thr His
465                 470                 475                 480

Tyr Gln Ala Met Leu Leu Asp Ala Glu Arg Val His Phe Gly Pro Thr
                485                 490                 495

Val Ser Leu Asn Pro Ala Thr Leu Leu Pro Leu Pro Ser Gly Lys Pro
                500                 505                 510

Pro Arg Leu Ser Pro Asp Leu Ala Glu Thr Met Ala Gln Thr Asp Leu
                515                 520                 525

Thr Asp Gln Pro Leu Pro Asp Ala Asp Leu Thr Trp Tyr Thr Gly Gly
530                 535                 540

Ser Ser Phe Ile Arg Asn Gly Glu Arg Lys Ala Gly Ala Ala Val Thr

```
                545                 550                 555                 560
Thr Glu Ser Glu Val Ile Trp Ala Ala Ser Leu Pro Pro Gly Thr Ser
                    565                 570                 575
Ala Gln Arg Ala Glu Leu Ile Ala Leu Thr Gln Ala Leu Lys Met Ala
                580                 585                 590
Lys Gly Lys Lys Leu Thr Val Tyr Thr Asp Ser Arg Tyr Ala Phe Ala
                595                 600                 605
Thr Ala His Val His Gly Glu Ile Tyr Arg Arg Gly Trp Leu Thr
            610                 615                 620
Ser Lys Gly Lys Glu Ile Lys Asn Lys Asn Glu Ile Leu Ala Leu Leu
625                 630                 635                 640
Glu Ala Leu Phe Leu Pro Lys Arg Leu Ser Ile Ile His Cys Pro Gly
                    645                 650                 655
His Gln Lys Gly Asp Ser Pro Gln Ala Lys Gly Asn Arg Leu Ala Asp
                660                 665                 670
Asp Thr Ala Lys Lys Ala Ala Thr Glu Thr Gln Ser Ser Leu Thr Ile
                675                 680                 685
Leu Ala Ala Ala
        690
```

<210> SEQ ID NO 24
<211> LENGTH: 692
<212> TYPE: PRT
<213> ORGANISM: Artificial Sequence
<220> FEATURE:
<223> OTHER INFORMATION: Synthetic construct

<400> SEQUENCE: 24

```
Met Gly Ser Ser His His His His His His Ser Ser Gly Leu Val Pro
1               5                   10                  15
Arg Gly Ser His Met Thr Leu Asn Ile Glu Asp Glu Tyr Arg Leu His
                20                  25                  30
Glu Thr Ser Lys Glu Pro Asp Val Ser Leu Gly Ser Thr Trp Leu Ser
            35                  40                  45
Asp Phe Pro Gln Ala Trp Ala Glu Thr Gly Gly Met Gly Leu Ala Val
50                  55                  60
Arg Gln Ala Pro Leu Ile Ile Pro Leu Lys Ala Thr Ser Thr Pro Val
65                  70                  75                  80
Ser Ile Lys Gln Tyr Pro Met Ser Gln Glu Ala Arg Leu Gly Ile Lys
                85                  90                  95
Pro His Ile Gln Arg Leu Leu Asp Gln Gly Ile Leu Val Pro Cys Gln
            100                 105                 110
Ser Pro Trp Asn Thr Pro Leu Leu Pro Val Lys Lys Pro Gly Thr Asn
        115                 120                 125
Asp Tyr Arg Pro Val Gln Asp Leu Arg Glu Val Asn Lys Arg Val Glu
    130                 135                 140
Asp Ile His Pro Thr Val Pro Asn Pro Tyr Asn Leu Leu Ser Gly Leu
145                 150                 155                 160
Pro Pro Ser His Gln Trp Tyr Thr Val Leu Asp Leu Lys Asp Ala Phe
                165                 170                 175
Phe Cys Leu Arg Leu His Pro Thr Ser Gln Pro Leu Phe Ala Phe Glu
            180                 185                 190
Trp Arg Asp Pro Glu Met Gly Ile Ser Gly Gln Leu Thr Trp Thr Arg
        195                 200                 205
Leu Pro Gln Gly Phe Lys Asn Ser Pro Thr Leu Phe Asn Glu Ala Leu
```

-continued

```
                210                 215                 220

His Arg Asp Leu Ala Asp Phe Arg Ile Gln His Pro Asp Leu Ile Leu
225                 230                 235                 240

Leu Gln Tyr Val Asp Asp Leu Leu Ala Ala Thr Arg Thr Glu
                245                 250                 255

Cys Leu Glu Gly Thr Lys Ala Leu Leu Glu Thr Leu Gly Asn Lys Gly
                260                 265                 270

Tyr Arg Ala Ser Ala Lys Lys Ala Gln Ile Cys Leu Gln Glu Val Thr
                275                 280                 285

Tyr Leu Gly Tyr Ser Leu Lys Asp Gly Gln Arg Trp Leu Thr Lys Ala
                290                 295                 300

Arg Lys Glu Ala Ile Leu Ser Ile Pro Val Pro Lys Asn Pro Arg Gln
305                 310                 315                 320

Val Arg Glu Phe Leu Gly Thr Ala Gly Tyr Cys Arg Leu Trp Ile Pro
                325                 330                 335

Gly Phe Ala Glu Leu Ala Ala Pro Leu Tyr Pro Leu Thr Arg Pro Gly
                340                 345                 350

Thr Leu Phe Gln Trp Gly Thr Glu Gln Gln Leu Ala Phe Glu Asn Ile
                355                 360                 365

Arg Lys Ala Leu Leu Ser Ser Pro Ala Leu Gly Leu Pro Asp Ile Thr
                370                 375                 380

Lys Pro Phe Glu Leu Phe Ile Asp Glu Asn Ser Gly Phe Ala Lys Gly
385                 390                 395                 400

Val Leu Val Gln Lys Leu Gly Pro Trp Lys Arg Pro Val Ala Tyr Leu
                405                 410                 415

Ser Lys Lys Leu Asp Thr Val Ala Ser Gly Trp Pro Pro Cys Leu Arg
                420                 425                 430

Met Val Ala Ala Ile Ala Ile Leu Val Lys Asp Ala Gly Lys Leu Thr
                435                 440                 445

Leu Gly Gln Pro Leu Thr Ile Leu Thr Ser His Pro Val Glu Ala Leu
                450                 455                 460

Val Arg Gln Pro Pro Asn Lys Trp Leu Ser Asn Ala Arg Met Thr His
465                 470                 475                 480

Tyr Gln Ala Met Leu Leu Asp Ala Glu Arg Val His Phe Gly Pro Thr
                485                 490                 495

Val Ser Leu Asp Pro Ala Thr Leu Leu Pro Leu Pro Ser Gly Lys Pro
                500                 505                 510

Pro Arg Leu Ser Pro Asp Leu Ala Glu Thr Met Ala Gln Thr Asp Leu
                515                 520                 525

Thr Asp Gln Pro Leu Pro Asp Ala Asp Leu Thr Trp Tyr Thr Asp Gly
                530                 535                 540

Ser Ser Phe Ile Arg Asn Gly Glu Arg Lys Ala Gly Ala Ala Val Thr
545                 550                 555                 560

Thr Glu Ser Glu Val Ile Trp Ala Ala Ser Leu Pro Pro Gly Thr Ser
                565                 570                 575

Ala Gln Arg Ala Glu Leu Ile Ala Leu Thr Gln Ala Leu Lys Met Ala
                580                 585                 590

Lys Gly Lys Lys Leu Thr Val Tyr Thr Asp Ser Arg Tyr Ala Phe Ala
                595                 600                 605

Thr Ala His Val Lys Gly Glu Ile Tyr Arg Arg Gly Trp Leu Thr
                610                 615                 620

Ser Glu Gly Lys Glu Ile Lys Asn Lys Asn Glu Ile Leu Ala Leu Leu
625                 630                 635                 640
```

```
Glu Ala Leu Phe Leu Pro Lys Arg Leu Ser Ile Ile His Cys Pro Gly
                645                 650                 655

His Gln Lys Gly Asp Ser Pro Gln Ala Lys Gly Asn Arg Leu Ala Asp
            660                 665                 670

Asp Thr Ala Lys Lys Ala Ala Thr Glu Thr Gln Ser Ser Leu Thr Ile
        675                 680                 685

Leu Ala Ala Ala
    690

<210> SEQ ID NO 25
<211> LENGTH: 692
<212> TYPE: PRT
<213> ORGANISM: Artificial Sequence
<220> FEATURE:
<223> OTHER INFORMATION: Synthetic construct

<400> SEQUENCE: 25

Met Gly Ser Ser His His His His His His Ser Ser Gly Leu Val Pro
1               5                   10                  15

Arg Gly Ser His Met Thr Leu Asn Ile Glu Asp Glu Tyr Arg Leu His
            20                  25                  30

Glu Thr Ser Lys Glu Pro Asp Val Ser Leu Gly Ser Thr Trp Leu Ser
        35                  40                  45

Asp Phe Pro Gln Ala Trp Ala Glu Thr Gly Met Gly Leu Ala Val
    50                  55                  60

Arg Gln Ala Pro Leu Ile Ile Pro Leu Lys Ala Thr Ser Thr Pro Val
65                  70                  75                  80

Ser Ile Lys Gln Tyr Pro Met Ser Gln Glu Ala Arg Leu Gly Ile Lys
                85                  90                  95

Pro His Ile Gln Arg Leu Leu Asp Gln Gly Ile Leu Val Pro Cys Gln
            100                 105                 110

Ser Pro Trp Asn Thr Pro Leu Leu Pro Val Lys Lys Pro Gly Thr Asn
        115                 120                 125

Asp Tyr Arg Pro Val Gln Asp Leu Arg Glu Val Asn Lys Arg Val Glu
    130                 135                 140

Asp Ile His Pro Thr Val Pro Asn Pro Tyr Asn Leu Leu Ser Gly Leu
145                 150                 155                 160

Pro Pro Ser His Gln Trp Tyr Thr Val Leu Asp Leu Lys Asp Ala Phe
                165                 170                 175

Phe Cys Leu Arg Leu His Pro Thr Ser Gln Pro Leu Phe Ala Phe Glu
            180                 185                 190

Trp Arg Asp Pro Glu Met Gly Ile Ser Gly Gln Leu Thr Trp Thr Arg
        195                 200                 205

Leu Pro Gln Gly Phe Lys Asn Ser Pro Thr Leu Phe Asn Glu Ala Leu
    210                 215                 220

His Arg Asp Leu Ala Asp Phe Arg Ile Gln His Pro Asp Leu Ile Leu
225                 230                 235                 240

Leu Gln Tyr Val Asp Asp Leu Leu Ala Ala Thr Arg Thr Glu
                245                 250                 255

Cys Leu Glu Gly Thr Lys Ala Leu Leu Glu Thr Leu Gly Asn Lys Gly
            260                 265                 270

Tyr Arg Ala Ser Ala Lys Lys Ala Gln Ile Cys Leu Gln Glu Val Thr
        275                 280                 285

Tyr Leu Gly Tyr Ser Leu Lys Asp Gly Gln Arg Trp Leu Thr Lys Ala
    290                 295                 300
```

Arg Lys Glu Ala Ile Leu Ser Ile Pro Val Pro Lys Asn Pro Arg Gln
305                 310                 315                 320

Val Arg Glu Phe Leu Gly Thr Ala Gly Tyr Cys Arg Leu Trp Ile Pro
            325                 330                 335

Gly Phe Ala Glu Leu Ala Ala Pro Leu Tyr Pro Leu Thr Arg Pro Gly
        340                 345                 350

Thr Leu Phe Gln Trp Gly Thr Glu Gln Gln Leu Ala Phe Glu Asn Ile
    355                 360                 365

Arg Lys Ala Leu Leu Ser Ser Pro Ala Leu Gly Leu Pro Asp Ile Thr
    370                 375                 380

Lys Pro Phe Glu Leu Phe Ile Asp Glu Asn Ser Gly Phe Ala Lys Gly
385                 390                 395                 400

Val Leu Val Gln Lys Leu Gly Pro Trp Lys Arg Pro Val Ala Tyr Leu
                405                 410                 415

Ser Lys Lys Leu Asp Thr Val Ala Ser Gly Trp Pro Pro Cys Leu Arg
                420                 425                 430

Met Val Ala Ala Ile Ala Ile Leu Val Lys Asp Ala Gly Lys Leu Thr
            435                 440                 445

Leu Gly Gln Pro Leu Thr Ile Leu Thr Ser His Pro Val Glu Ala Leu
    450                 455                 460

Val Arg Gln Pro Pro Asn Lys Trp Leu Ser Asn Ala Arg Met Thr His
465                 470                 475                 480

Tyr Gln Ala Met Leu Leu Asp Ala Glu Arg Val His Phe Gly Pro Thr
            485                 490                 495

Val Ser Leu Asn Pro Ala Thr Leu Leu Pro Leu Pro Ser Gly Lys Pro
                500                 505                 510

Pro Arg Leu Ser Pro Asp Leu Ala Glu Thr Met Ala Gln Thr Asp Leu
            515                 520                 525

Thr Asp Gln Pro Leu Pro Asp Ala Asp Leu Thr Trp Tyr Thr Gly Gly
    530                 535                 540

Ser Ser Phe Ile Arg Asn Gly Glu Arg Lys Ala Gly Ala Ala Val Thr
545                 550                 555                 560

Thr Glu Ser Glu Val Ile Trp Ala Ala Ser Leu Pro Pro Gly Thr Ser
                565                 570                 575

Ala Gln Arg Ala Glu Leu Ile Ala Leu Thr Gln Ala Leu Lys Met Ala
            580                 585                 590

Lys Gly Lys Lys Leu Thr Val Tyr Thr Asp Ser Arg Tyr Ala Phe Ala
            595                 600                 605

Thr Ala His Val His Gly Glu Ile Tyr Arg Arg Gly Trp Leu Thr
    610                 615                 620

Ser Glu Gly Lys Glu Ile Lys Asn Lys Asn Glu Ile Leu Ala Leu Leu
625                 630                 635                 640

Glu Ala Leu Phe Leu Pro Lys Arg Leu Ser Ile Ile His Cys Pro Gly
            645                 650                 655

His Gln Lys Gly Asp Ser Pro Gln Ala Lys Gly Asn Arg Leu Ala Asn
            660                 665                 670

Asp Thr Ala Lys Lys Ala Ala Thr Glu Thr Gln Ser Ser Leu Thr Ile
            675                 680                 685

Leu Ala Ala Ala
    690

<210> SEQ ID NO 26
<211> LENGTH: 279

```
<212> TYPE: PRT
<213> ORGANISM: Unknown
<220> FEATURE:
<223> OTHER INFORMATION: Feline Leukemia Virus

<400> SEQUENCE: 26

Met Thr Leu Gln Leu Glu Glu Glu Tyr Arg Leu Phe Glu Pro Glu Ser
1               5                   10                  15

Thr Gln Lys Gln Glu Met Asp Ile Trp Leu Lys Asn Phe Pro Gln Ala
            20                  25                  30

Trp Ala Glu Thr Gly Gly Met Gly Met Ala His Cys Gln Ala Pro Val
        35                  40                  45

Leu Ile Gln Leu Lys Ala Thr Ala Thr Pro Ile Ser Ile Arg Gln Tyr
    50                  55                  60

Pro Met Pro His Glu Ala Tyr Gln Gly Ile Lys Pro His Ile Arg Arg
65                  70                  75                  80

Met Leu Asp Gln Gly Ile Leu Lys Pro Cys Gln Ser Pro Trp Asn Thr
                85                  90                  95

Pro Leu Leu Pro Val Lys Lys Pro Gly Thr Lys Asp Tyr Arg Pro Val
            100                 105                 110

Gln Asp Leu Arg Glu Val Asn Lys Arg Val Glu Asp Ile His Pro Thr
        115                 120                 125

Val Pro Asn Pro Tyr Asn Leu Leu Ser Thr Leu Pro Pro Ser His Pro
130                 135                 140

Trp Tyr Thr Val Leu Asp Leu Lys Asp Ala Phe Phe Cys Leu Arg Leu
145                 150                 155                 160

His Ser Glu Ser Gln Leu Leu Phe Ala Phe Glu Trp Arg Asp Pro Glu
                165                 170                 175

Ile Gly Leu Ser Gly Gln Leu Thr Trp Thr Arg Leu Pro Gln Gly Phe
            180                 185                 190

Lys Asn Ser Pro Thr Leu Phe Asp Glu Ala Leu His Ser Asp Leu Ala
        195                 200                 205

Asp Phe Arg Val Arg Tyr Pro Ala Leu Val Leu Leu Gln Tyr Val Asp
    210                 215                 220

Asp Leu Leu Leu Ala Ala Ala Thr Arg Thr Glu Cys Leu Glu Gly Thr
225                 230                 235                 240

Lys Ala Leu Leu Glu Thr Leu Gly Asn Lys Gly Tyr Arg Ala Ser Ala
                245                 250                 255

Lys Lys Ala Gln Ile Cys Leu Gln Glu Val Thr Tyr Leu Gly Tyr Ser
            260                 265                 270

Leu Lys Asp Gly Gln Arg Trp
        275

<210> SEQ ID NO 27
<211> LENGTH: 497
<212> TYPE: PRT
<213> ORGANISM: Unknown
<220> FEATURE:
<223> OTHER INFORMATION: Feline Leukemia Virus

<400> SEQUENCE: 27

Met Thr Leu Gln Leu Glu Glu Glu Tyr Arg Leu Phe Glu Pro Glu Ser
1               5                   10                  15

Thr Gln Lys Gln Glu Met Asp Ile Trp Leu Lys Asn Phe Pro Gln Ala
            20                  25                  30

Trp Ala Glu Thr Gly Gly Met Gly Met Ala His Cys Gln Ala Pro Val
        35                  40                  45
```

Leu Ile Gln Leu Lys Ala Thr Ala Thr Pro Ile Ser Ile Arg Gln Tyr
        50                  55                  60

Pro Met Pro His Glu Ala Tyr Gln Gly Ile Lys Pro His Ile Arg Arg
65                  70                  75                  80

Met Leu Asp Gln Gly Ile Leu Lys Pro Cys Gln Ser Pro Trp Asn Thr
                    85                  90                  95

Pro Leu Leu Pro Val Lys Lys Pro Gly Thr Lys Asp Tyr Arg Pro Val
                100                 105                 110

Gln Asp Leu Arg Glu Val Asn Lys Arg Val Glu Asp Ile His Pro Thr
                115                 120                 125

Val Pro Asn Pro Tyr Asn Leu Leu Ser Thr Leu Pro Pro Ser His Pro
        130                 135                 140

Trp Tyr Thr Val Leu Asp Leu Lys Asp Ala Phe Phe Cys Leu Arg Leu
145                 150                 155                 160

His Ser Glu Ser Gln Leu Leu Phe Ala Phe Glu Trp Arg Asp Pro Glu
                    165                 170                 175

Ile Gly Leu Ser Gly Gln Leu Thr Trp Thr Arg Leu Pro Gln Gly Phe
                180                 185                 190

Lys Asn Ser Pro Thr Leu Phe Asp Glu Ala Leu His Ser Asp Leu Ala
                195                 200                 205

Asp Phe Arg Val Arg Tyr Pro Ala Leu Val Leu Leu Gln Tyr Val Asp
        210                 215                 220

Asp Leu Leu Leu Ala Ala Ala Thr Arg Thr Glu Cys Leu Glu Gly Thr
225                 230                 235                 240

Lys Ala Leu Leu Glu Thr Leu Gly Asn Lys Gly Tyr Arg Ala Ser Ala
                    245                 250                 255

Lys Lys Ala Gln Ile Cys Leu Gln Glu Val Thr Tyr Leu Gly Tyr Ser
                260                 265                 270

Leu Lys Asp Gly Gln Arg Trp Leu Thr Lys Ala Arg Lys Glu Ala Ile
                275                 280                 285

Leu Ser Ile Pro Val Pro Lys Asn Pro Arg Gln Val Arg Glu Phe Leu
        290                 295                 300

Gly Thr Ala Gly Tyr Cys Arg Leu Trp Ile Pro Gly Phe Ala Glu Leu
305                 310                 315                 320

Ala Ala Pro Leu Tyr Pro Leu Thr Arg Pro Gly Thr Leu Phe Gln Trp
                    325                 330                 335

Gly Thr Glu Gln Gln Leu Ala Phe Glu Asn Ile Arg Lys Ala Leu Leu
                340                 345                 350

Ser Ser Pro Ala Leu Gly Leu Pro Asp Ile Thr Lys Pro Phe Glu Leu
                355                 360                 365

Phe Ile Asp Glu Asn Ser Gly Phe Ala Lys Gly Val Leu Val Gln Lys
        370                 375                 380

Leu Gly Pro Trp Lys Arg Pro Val Ala Tyr Leu Ser Lys Lys Leu Asp
385                 390                 395                 400

Thr Val Ala Ser Gly Trp Pro Pro Cys Leu Arg Met Val Ala Ala Ile
                    405                 410                 415

Ala Ile Leu Val Lys Asp Ala Gly Lys Leu Thr Leu Gly Gln Pro Leu
                420                 425                 430

Thr Ile Leu Thr Ser His Pro Val Glu Ala Leu Val Arg Gln Pro Pro
                435                 440                 445

Asn Lys Trp Leu Ser Asn Ala Arg Met Thr His Tyr Gln Ala Met Leu
        450                 455                 460

```
Leu Asp Ala Glu Arg Val His Phe Gly Pro Thr Val Ser Leu Asn Pro
465                 470                 475                 480

Ala Thr Leu Leu Pro Leu Pro Ser Gly Lys Pro Pro Arg Leu Ser Pro
                485                 490                 495

Asp

<210> SEQ ID NO 28
<211> LENGTH: 392
<212> TYPE: PRT
<213> ORGANISM: Unknown
<220> FEATURE:
<223> OTHER INFORMATION: Mouse Leukemia Virus

<400> SEQUENCE: 28

Leu Thr Glu Ala Arg Lys Glu Thr Val Met Gly Gln Pro Thr Pro Lys
1               5                   10                  15

Thr Pro Arg Gln Leu Arg Glu Phe Leu Gly Thr Ala Gly Phe Cys Arg
            20                  25                  30

Leu Trp Ile Pro Gly Phe Ala Glu Met Ala Ala Pro Leu Tyr Pro Leu
        35                  40                  45

Thr Lys Thr Gly Thr Leu Phe Asn Trp Gly Pro Asp Gln Gln Lys Ala
    50                  55                  60

Tyr Gln Glu Ile Lys Gln Ala Leu Leu Thr Ala Pro Ala Leu Gly Leu
65                  70                  75                  80

Pro Asp Leu Thr Lys Pro Phe Glu Leu Phe Val Asp Glu Lys Gln Gly
                85                  90                  95

Tyr Ala Lys Gly Val Leu Thr Gln Lys Leu Gly Pro Trp Arg Arg Pro
            100                 105                 110

Val Ala Tyr Leu Ser Lys Lys Leu Asp Pro Val Ala Ala Gly Trp Pro
        115                 120                 125

Pro Cys Leu Arg Met Val Ala Ala Ile Ala Val Leu Thr Lys Asp Ala
    130                 135                 140

Gly Lys Leu Thr Met Gly Gln Pro Leu Val Ile Leu Ala Pro His Ala
145                 150                 155                 160

Val Glu Ala Leu Val Lys Gln Pro Pro Asp Arg Trp Leu Ser Asn Ala
                165                 170                 175

Arg Met Thr His Tyr Gln Ala Leu Leu Leu Asp Thr Asp Arg Val Gln
            180                 185                 190

Phe Gly Pro Val Val Ala Leu Asn Pro Ala Thr Leu Leu Pro Leu Pro
        195                 200                 205

Glu Glu Gly Leu Gln His Asp Cys Leu Asp Ile Leu Ala Glu Ala His
    210                 215                 220

Gly Thr Arg Ser Asp Leu Thr Asp Gln Pro Leu Pro Asp Ala Asp His
225                 230                 235                 240

Thr Trp Tyr Thr Asp Gly Ser Ser Phe Leu Gln Glu Gly Gln Arg Lys
                245                 250                 255

Ala Gly Ala Ala Val Thr Thr Glu Thr Glu Val Ile Trp Ala Arg Ala
            260                 265                 270

Leu Pro Ala Gly Thr Ser Ala Gln Arg Ala Glu Leu Ile Ala Leu Thr
        275                 280                 285

Gln Ala Leu Lys Met Ala Glu Gly Lys Lys Leu Asn Val Tyr Thr Asp
    290                 295                 300

Ser Arg Tyr Ala Phe Ala Thr Ala His Ile His Gly Glu Ile Tyr Arg
305                 310                 315                 320

Arg Arg Gly Leu Leu Thr Ser Glu Gly Lys Glu Ile Lys Asn Lys Asp
```

```
                    325                 330                 335
Glu Ile Leu Ala Leu Leu Lys Ala Leu Phe Leu Pro Lys Arg Leu Ser
                340                 345                 350
Ile Ile His Cys Pro Gly His Gln Lys Gly Asn Ser Ala Glu Ala Arg
            355                 360                 365
Gly Asn Arg Met Ala Asp Gln Ala Ala Arg Glu Val Ala Thr Arg Glu
        370                 375                 380
Thr Pro Gly Thr Ser Thr Leu Leu
385                 390

<210> SEQ ID NO 29
<211> LENGTH: 174
<212> TYPE: PRT
<213> ORGANISM: Unknown
<220> FEATURE:
<223> OTHER INFORMATION: Mouse Leukemia Virus

<400> SEQUENCE: 29

Ile Leu Ala Glu Ala His Gly Thr Arg Ser Asp Leu Thr Asp Gln Pro
1               5                   10                  15
Leu Pro Asp Ala Asp His Thr Trp Tyr Thr Asp Gly Ser Ser Phe Leu
            20                  25                  30
Gln Glu Gly Gln Arg Lys Ala Gly Ala Ala Val Thr Thr Glu Thr Glu
        35                  40                  45
Val Ile Trp Ala Arg Ala Leu Pro Ala Gly Thr Ser Ala Gln Arg Ala
    50                  55                  60
Glu Leu Ile Ala Leu Thr Gln Ala Leu Lys Met Ala Glu Gly Lys Lys
65                  70                  75                  80
Leu Asn Val Tyr Thr Asp Ser Arg Tyr Ala Phe Ala Thr Ala His Ile
                85                  90                  95
His Gly Glu Ile Tyr Arg Arg Arg Gly Leu Leu Thr Ser Glu Gly Lys
            100                 105                 110
Glu Ile Lys Asn Lys Asp Glu Ile Leu Ala Leu Leu Lys Ala Leu Phe
        115                 120                 125
Leu Pro Lys Arg Leu Ser Ile Ile His Cys Pro Gly His Gln Lys Gly
    130                 135                 140
Asn Ser Ala Glu Ala Arg Gly Asn Arg Met Ala Asp Gln Ala Ala Arg
145                 150                 155                 160
Glu Val Ala Thr Arg Glu Thr Pro Gly Thr Ser Thr Leu Leu
                165                 170

<210> SEQ ID NO 30
<211> LENGTH: 671
<212> TYPE: PRT
<213> ORGANISM: Artificial Sequence
<220> FEATURE:
<223> OTHER INFORMATION: Synthetic construct

<400> SEQUENCE: 30

Met Thr Leu Gln Leu Glu Glu Tyr Arg Leu Phe Glu Pro Glu Ser
1               5                   10                  15
Thr Gln Lys Gln Glu Met Asp Ile Trp Leu Lys Asn Phe Pro Gln Ala
            20                  25                  30
Trp Ala Glu Thr Gly Gly Met Gly Met Ala His Cys Gln Ala Pro Val
        35                  40                  45
Leu Ile Gln Leu Lys Ala Thr Ala Thr Pro Ile Ser Ile Arg Gln Tyr
    50                  55                  60
```

-continued

```
Pro Met Pro His Glu Ala Tyr Gln Gly Ile Lys Pro His Ile Arg Arg
 65                  70                  75                  80

Met Leu Asp Gln Gly Ile Leu Lys Pro Cys Gln Ser Pro Trp Asn Thr
                 85                  90                  95

Pro Leu Leu Pro Val Lys Lys Pro Gly Thr Lys Asp Tyr Arg Pro Val
            100                 105                 110

Gln Asp Leu Arg Glu Val Asn Lys Arg Val Glu Asp Ile His Pro Thr
        115                 120                 125

Val Pro Asn Pro Tyr Asn Leu Leu Ser Thr Leu Pro Pro Ser His Pro
    130                 135                 140

Trp Tyr Thr Val Leu Asp Leu Lys Asp Ala Phe Phe Cys Leu Arg Leu
145                 150                 155                 160

His Ser Glu Ser Gln Leu Leu Phe Ala Phe Glu Trp Arg Asp Pro Glu
                165                 170                 175

Ile Gly Leu Ser Gly Gln Leu Thr Trp Thr Arg Leu Pro Gln Gly Phe
            180                 185                 190

Lys Asn Ser Pro Thr Leu Phe Asp Glu Ala Leu His Ser Asp Leu Ala
        195                 200                 205

Asp Phe Arg Val Arg Tyr Pro Ala Leu Val Leu Leu Gln Tyr Val Asp
    210                 215                 220

Asp Leu Leu Leu Ala Ala Ala Thr Arg Thr Glu Cys Leu Glu Gly Thr
225                 230                 235                 240

Lys Ala Leu Leu Glu Thr Leu Gly Asn Lys Gly Tyr Arg Ala Ser Ala
                245                 250                 255

Lys Lys Ala Gln Ile Cys Leu Gln Glu Val Thr Tyr Leu Gly Tyr Ser
            260                 265                 270

Leu Lys Asp Gly Gln Arg Trp Leu Thr Glu Ala Arg Lys Glu Thr Val
        275                 280                 285

Met Gly Gln Pro Thr Pro Lys Thr Pro Arg Gln Leu Arg Glu Phe Leu
    290                 295                 300

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Thr Leu Phe Asn Trp
                325                 330                 335

Gly Pro Asp Gln Gln Lys Ala Tyr Gln Glu Ile Lys Gln Ala Leu Leu
            340                 345                 350

Thr Ala Pro Ala Leu Gly Leu Pro Asp Leu Thr Lys Pro Phe Glu Leu
        355                 360                 365

Phe Val Asp Glu Lys Gln Gly Tyr Ala Lys Gly Val Leu Thr Gln Lys
    370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
            420                 425                 430

Val Ile Leu Ala Pro His Ala Val Glu Ala Leu Val Lys Gln Pro Pro
        435                 440                 445

Asp Arg Trp Leu Ser Asn Ala Arg Met Thr His Tyr Gln Ala Leu Leu
    450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asp Cys Leu
```

```
                485                 490                 495
Asp Ile Leu Ala Glu Ala His Gly Thr Arg Ser Asp Leu Thr Asp Gln
                500                 505                 510

Pro Leu Pro Asp Ala Asp His Thr Trp Tyr Thr Asp Gly Ser Ser Phe
            515                 520                 525

Leu Gln Glu Gly Gln Arg Lys Ala Gly Ala Ala Val Thr Thr Glu Thr
        530                 535                 540

Glu Val Ile Trp Ala Arg Ala Leu Pro Ala Gly Thr Ser Ala Gln Arg
545                 550                 555                 560

Ala Glu Leu Ile Ala Leu Thr Gln Ala Leu Lys Met Ala Glu Gly Lys
                565                 570                 575

Lys Leu Asn Val Tyr Thr Asp Ser Arg Tyr Ala Phe Ala Thr Ala His
            580                 585                 590

Ile His Gly Glu Ile Tyr Arg Arg Arg Gly Leu Leu Thr Ser Glu Gly
        595                 600                 605

Lys Glu Ile Lys Asn Lys Asp Glu Ile Leu Ala Leu Leu Lys Ala Leu
            610                 615                 620

Phe Leu Pro Lys Arg Leu Ser Ile Ile His Cys Pro Gly His Gln Lys
625                 630                 635                 640

Gly Asn Ser Ala Glu Ala Arg Gly Asn Arg Met Ala Asp Gln Ala Ala
                645                 650                 655

Arg Glu Val Ala Thr Arg Glu Thr Pro Gly Thr Ser Thr Leu Leu
            660                 665                 670

<210> SEQ ID NO 31
<211> LENGTH: 671
<212> TYPE: PRT
<213> ORGANISM: Artificial Sequence
<220> FEATURE:
<223> OTHER INFORMATION: Synthetic construct

<400> SEQUENCE: 31

Met Thr Leu Gln Leu Glu Glu Tyr Arg Leu Phe Glu Pro Glu Ser
1               5                   10                  15

Thr Gln Lys Gln Glu Met Asp Ile Trp Leu Lys Asn Phe Pro Gln Ala
                20                  25                  30

Trp Ala Glu Thr Gly Gly Met Gly Met Ala His Cys Gln Ala Pro Val
            35                  40                  45

Leu Ile Gln Leu Lys Ala Thr Ala Thr Pro Ile Ser Ile Arg Gln Tyr
        50                  55                  60

Pro Met Pro His Glu Ala Tyr Gln Gly Ile Lys Pro His Ile Arg Arg
65                  70                  75                  80

Met Leu Asp Gln Gly Ile Leu Lys Pro Cys Gln Ser Pro Trp Asn Thr
                85                  90                  95

Pro Leu Leu Pro Val Lys Lys Pro Gly Thr Lys Asp Tyr Arg Pro Val
            100                 105                 110

Gln Asp Leu Arg Glu Val Asn Lys Arg Val Glu Asp Ile His Pro Thr
        115                 120                 125

Val Pro Asn Pro Tyr Asn Leu Leu Ser Thr Leu Pro Pro Ser His Pro
    130                 135                 140

Trp Tyr Thr Val Leu Asp Leu Lys Asp Ala Phe Phe Cys Leu Arg Leu
145                 150                 155                 160

His Ser Glu Ser Gln Leu Leu Phe Ala Phe Glu Trp Arg Asp Pro Glu
                165                 170                 175

Ile Gly Leu Ser Gly Gln Leu Thr Trp Thr Arg Leu Pro Gln Gly Phe
```

-continued

```
                180                 185                 190
Lys Asn Ser Pro Thr Leu Phe Asp Glu Ala Leu His Ser Asp Leu Ala
            195                 200                 205
Asp Phe Arg Val Arg Tyr Pro Ala Leu Val Leu Leu Gln Tyr Val Asp
        210                 215                 220
Asp Leu Leu Leu Ala Ala Thr Arg Thr Glu Cys Leu Glu Gly Thr
225                 230                 235                 240
Lys Ala Leu Leu Glu Thr Leu Gly Asn Lys Gly Tyr Arg Ala Ser Ala
                245                 250                 255
Lys Lys Ala Gln Ile Cys Leu Gln Glu Val Thr Tyr Leu Gly Tyr Ser
            260                 265                 270
Leu Lys Asp Gly Gln Arg Trp Leu Thr Lys Ala Arg Lys Glu Ala Ile
        275                 280                 285
Leu Ser Ile Pro Val Pro Lys Asn Pro Arg Gln Val Arg Glu Phe Leu
290                 295                 300
Gly Thr Ala Gly Tyr Cys Arg Leu Trp Ile Pro Gly Phe Ala Glu Leu
305                 310                 315                 320
Ala Ala Pro Leu Tyr Pro Leu Thr Arg Pro Gly Thr Leu Phe Gln Trp
                325                 330                 335
Gly Thr Glu Gln Gln Leu Ala Phe Glu Asn Ile Arg Lys Ala Leu Leu
            340                 345                 350
Ser Ser Pro Ala Leu Gly Leu Pro Asp Ile Thr Lys Pro Phe Glu Leu
        355                 360                 365
Phe Ile Asp Glu Asn Ser Gly Phe Ala Lys Gly Val Leu Val Gln Lys
    370                 375                 380
Leu Gly Pro Trp Lys Arg Pro Val Ala Tyr Leu Ser Lys Lys Leu Asp
385                 390                 395                 400
Thr Val Ala Ser Gly Trp Pro Pro Cys Leu Arg Met Val Ala Ala Ile
                405                 410                 415
Ala Ile Leu Val Lys Asp Ala Gly Lys Leu Thr Leu Gly Gln Pro Leu
            420                 425                 430
Thr Ile Leu Thr Ser His Pro Val Glu Ala Leu Val Arg Gln Pro Pro
        435                 440                 445
Asn Lys Trp Leu Ser Asn Ala Arg Met Thr His Tyr Gln Ala Met Leu
    450                 455                 460
Leu Asp Ala Glu Arg Val His Phe Gly Pro Thr Val Ser Leu Asn Pro
465                 470                 475                 480
Ala Thr Leu Leu Pro Leu Pro Ser Gly Lys Pro Pro Arg Leu Ser Pro
                485                 490                 495
Asp Ile Leu Ala Glu Ala His Gly Thr Arg Ser Asp Leu Thr Asp Gln
            500                 505                 510
Pro Leu Pro Asp Ala Asp His Thr Trp Tyr Thr Asp Gly Ser Ser Phe
        515                 520                 525
Leu Gln Glu Gly Gln Arg Lys Ala Gly Ala Ala Val Thr Thr Glu Thr
    530                 535                 540
Glu Val Ile Trp Ala Arg Ala Leu Pro Ala Gly Thr Ser Ala Gln Arg
545                 550                 555                 560
Ala Glu Leu Ile Ala Leu Thr Gln Ala Leu Lys Met Ala Glu Gly Lys
                565                 570                 575
Lys Leu Asn Val Tyr Thr Asp Ser Arg Tyr Ala Phe Ala Thr Ala His
            580                 585                 590
Ile His Gly Glu Ile Tyr Arg Arg Arg Gly Leu Leu Thr Ser Glu Gly
        595                 600                 605
```

```
Lys Glu Ile Lys Asn Lys Asp Glu Ile Leu Ala Leu Leu Lys Ala Leu
        610                 615                 620
Phe Leu Pro Lys Arg Leu Ser Ile Ile His Cys Pro Gly His Gln Lys
625                 630                 635                 640
Gly Asn Ser Ala Glu Ala Arg Gly Asn Arg Met Ala Asp Gln Ala Ala
                645                 650                 655
Arg Glu Val Ala Thr Arg Glu Thr Pro Gly Thr Ser Thr Leu Leu
            660                 665                 670

<210> SEQ ID NO 32
<211> LENGTH: 671
<212> TYPE: PRT
<213> ORGANISM: Unknown
<220> FEATURE:
<223> OTHER INFORMATION: Mouse Leukemia Virus

<400> SEQUENCE: 32

Thr Leu Asn Ile Glu Asp Glu His Arg Leu His Glu Thr Ser Lys Glu
1               5                   10                  15
Pro Asp Val Ser Leu Gly Ser Thr Trp Leu Ser Asp Phe Pro Gln Ala
                20                  25                  30
Trp Ala Glu Thr Gly Gly Met Gly Leu Ala Val Arg Gln Ala Pro Leu
            35                  40                  45
Ile Ile Pro Leu Lys Ala Thr Ser Thr Pro Val Ser Ile Lys Gln Tyr
    50                  55                  60
Pro Met Ser Gln Glu Ala Arg Leu Gly Ile Lys Pro His Ile Gln Arg
65                  70                  75                  80
Leu Leu Asp Gln Gly Ile Leu Val Pro Cys Gln Ser Pro Trp Asn Thr
                85                  90                  95
Pro Leu Leu Pro Val Lys Lys Pro Gly Thr Asn Asp Tyr Arg Pro Val
                100                 105                 110
Gln Asp Leu Arg Glu Val Asn Lys Arg Val Glu Asp Ile His Pro Thr
            115                 120                 125
Val Pro Asn Pro Tyr Asn Leu Leu Ser Gly Leu Pro Pro Ser His Gln
    130                 135                 140
Trp Tyr Thr Val Leu Asp Leu Lys Asp Ala Phe Phe Cys Leu Arg Leu
145                 150                 155                 160
His Pro Thr Ser Gln Pro Leu Phe Ala Phe Glu Trp Arg Asp Pro Glu
                165                 170                 175
Met Gly Ile Ser Gly Gln Leu Thr Trp Thr Arg Leu Pro Gln Gly Phe
            180                 185                 190
Lys Asn Ser Pro Thr Leu Phe Asp Glu Ala Leu His Arg Asp Leu Ala
    195                 200                 205
Asp Phe Arg Ile Gln His Pro Asp Leu Ile Leu Leu Gln Tyr Val Asp
    210                 215                 220
Asp Leu Leu Leu Ala Ala Thr Ser Glu Leu Asp Cys Gln Gln Gly Thr
225                 230                 235                 240
Arg Ala Leu Leu Gln Thr Leu Gly Asn Leu Gly Tyr Arg Ala Ser Ala
                245                 250                 255
Lys Lys Ala Gln Ile Cys Gln Lys Gln Val Lys Tyr Leu Gly Tyr Leu
                260                 265                 270
Leu Lys Glu Gly Gln Arg Trp Leu Thr Glu Ala Arg Lys Glu Thr Val
            275                 280                 285
Met Gly Gln Pro Thr Pro Lys Thr Pro Arg Gln Leu Arg Glu Phe Leu
    290                 295                 300
```

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Thr Leu Phe Asn Trp
            325                 330                 335

Gly Pro Asp Gln Gln Lys Ala Tyr Gln Glu Ile Lys Gln Ala Leu Leu
        340                 345                 350

Thr Ala Pro Ala Leu Gly Leu Pro Asp Leu Thr Lys Pro Phe Glu Leu
    355                 360                 365

Phe Val Asp Glu Lys Gln Gly Tyr Ala Lys Gly Val Leu Thr Gln Lys
370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
            420                 425                 430

Val Ile Leu Ala Pro His Ala Val Glu Ala Leu Val Lys Gln Pro Pro
        435                 440                 445

Asp Arg Trp Leu Ser Asn Ala Arg Met Thr His Tyr Gln Ala Leu Leu
    450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
            500                 505                 510

Pro Leu Pro Asp Ala Asp His Thr Trp Tyr Thr Asp Gly Ser Ser Leu
        515                 520                 525

Leu Gln Glu Gly Gln Arg Lys Ala Gly Ala Ala Val Thr Thr Glu Thr
    530                 535                 540

Glu Val Ile Trp Ala Lys Ala Leu Pro Ala Gly Thr Ser Ala Gln Arg
545                 550                 555                 560

Ala Glu Leu Ile Ala Leu Thr Gln Ala Leu Lys Met Ala Glu Gly Lys
                565                 570                 575

Lys Leu Asn Val Tyr Thr Asp Ser Arg Tyr Ala Phe Ala Thr Ala His
            580                 585                 590

Ile His Gly Glu Ile Tyr Arg Arg Gly Leu Leu Thr Ser Glu Gly
        595                 600                 605

Lys Glu Ile Lys Asn Lys Asp Glu Ile Leu Ala Leu Leu Lys Ala Leu
    610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
                645                 650                 655

Arg Lys Ala Ala Ile Thr Glu Thr Pro Asp Thr Ser Thr Leu Leu
            660                 665                 670

<210> SEQ ID NO 33
<211> LENGTH: 667
<212> TYPE: PRT
<213> ORGANISM: Unknown
<220> FEATURE:
<223> OTHER INFORMATION: Feline Leukemia Virus

<400> SEQUENCE: 33

-continued

```
Thr Leu Gln Leu Glu Glu Tyr Arg Leu Phe Glu Pro Glu Ser Thr
1               5                   10                  15

Gln Lys Gln Glu Met Asp Ile Trp Leu Lys Asn Phe Pro Gln Ala Trp
            20                  25                  30

Ala Glu Thr Gly Gly Met Gly Met Ala His Cys Gln Ala Pro Val Leu
        35                  40                  45

Ile Gln Leu Lys Ala Thr Ala Thr Pro Ile Ser Ile Arg Gln Tyr Pro
    50                  55                  60

Met Pro His Glu Ala Tyr Gln Gly Ile Lys Pro His Ile Arg Arg Met
65                  70                  75                  80

Leu Asp Gln Gly Ile Leu Lys Pro Cys Gln Ser Pro Trp Asn Thr Pro
                85                  90                  95

Leu Leu Pro Val Lys Lys Pro Gly Thr Lys Asp Tyr Arg Pro Val Gln
            100                 105                 110

Asp Leu Arg Glu Val Asn Lys Arg Val Glu Asp Ile His Pro Thr Val
        115                 120                 125

Pro Asn Pro Tyr Asn Leu Leu Ser Thr Leu Pro Pro Ser His Pro Trp
    130                 135                 140

Tyr Thr Val Leu Asp Leu Lys Asp Ala Phe Phe Cys Leu Arg Leu His
145                 150                 155                 160

Ser Glu Ser Gln Leu Leu Phe Ala Phe Glu Trp Arg Asp Pro Glu Ile
                165                 170                 175

Gly Leu Ser Gly Gln Leu Thr Trp Thr Arg Leu Pro Gln Gly Phe Lys
            180                 185                 190

Asn Ser Pro Thr Leu Phe Asp Glu Ala Leu His Ser Asp Leu Ala Asp
        195                 200                 205

Phe Arg Val Arg Tyr Pro Ala Leu Val Leu Leu Gln Tyr Val Asp Asp
    210                 215                 220

Leu Leu Leu Ala Ala Ala Thr Arg Thr Glu Cys Leu Glu Gly Thr Lys
225                 230                 235                 240

Ala Leu Leu Glu Thr Leu Gly Asn Lys Gly Tyr Arg Ala Ser Ala Lys
                245                 250                 255

Lys Ala Gln Ile Cys Leu Gln Glu Val Thr Tyr Leu Gly Tyr Ser Leu
            260                 265                 270

Lys Asp Gly Gln Arg Trp Leu Thr Lys Ala Arg Lys Glu Ala Ile Leu
        275                 280                 285

Ser Ile Pro Val Pro Lys Asn Pro Arg Gln Val Arg Glu Phe Leu Gly
    290                 295                 300

Thr Ala Gly Tyr Cys Arg Leu Trp Ile Pro Gly Phe Ala Glu Leu Ala
305                 310                 315                 320

Ala Pro Leu Tyr Pro Leu Thr Arg Pro Gly Thr Leu Phe Gln Trp Gly
                325                 330                 335

Thr Glu Gln Gln Leu Ala Phe Glu Asn Ile Arg Lys Ala Leu Leu Ser
            340                 345                 350

Ser Pro Ala Leu Gly Leu Pro Asp Ile Thr Lys Pro Phe Glu Leu Phe
        355                 360                 365

Ile Asp Glu Asn Ser Gly Phe Ala Lys Gly Val Leu Val Gln Lys Leu
    370                 375                 380

Gly Pro Trp Lys Arg Pro Val Ala Tyr Leu Ser Lys Lys Leu Asp Thr
385                 390                 395                 400

Val Ala Ser Gly Trp Pro Pro Cys Leu Arg Met Val Ala Ala Ile Ala
                405                 410                 415
```

Ile Leu Val Lys Asp Ala Gly Lys Leu Thr Leu Gly Gln Pro Leu Thr
            420                 425                 430

Ile Leu Thr Ser His Pro Val Glu Ala Leu Val Arg Gln Pro Pro Asn
        435                 440                 445

Lys Trp Leu Ser Asn Ala Arg Met Thr His Tyr Gln Ala Met Leu Leu
450                 455                 460

Asp Ala Glu Arg Val His Phe Gly Pro Thr Val Ser Leu Asn Pro Ala
465                 470                 475                 480

Thr Leu Leu Pro Leu Pro Ser Gly Lys Pro Pro Arg Leu Ser Pro Asp
                485                 490                 495

Leu Ala Glu Thr Met Ala Gln Thr Asp Leu Thr Asp Gln Pro Leu Pro
            500                 505                 510

Asp Ala Asp Leu Thr Trp Tyr Thr Asp Gly Ser Ser Phe Ile Arg Asn
        515                 520                 525

Gly Glu Arg Lys Ala Gly Ala Ala Val Thr Thr Glu Ser Glu Val Ile
530                 535                 540

Trp Ala Ala Ser Leu Pro Pro Gly Thr Ser Ala Gln Arg Ala Glu Leu
545                 550                 555                 560

Ile Ala Leu Thr Gln Ala Leu Lys Met Ala Lys Gly Lys Lys Leu Thr
                565                 570                 575

Val Tyr Thr Asp Ser Arg Tyr Ala Phe Ala Thr Ala His Val His Gly
            580                 585                 590

Glu Ile Tyr Arg Arg Arg Gly Leu Leu Thr Ser Glu Gly Lys Glu Ile
        595                 600                 605

Lys Asn Lys Asn Glu Ile Leu Ala Leu Leu Glu Ala Leu Phe Leu Pro
610                 615                 620

Lys Arg Leu Ser Ile Ile His Cys Pro Gly His Gln Lys Gly Asp Ser
625                 630                 635                 640

Pro Gln Ala Lys Gly Asn Arg Leu Ala Asp Asp Thr Ala Lys Lys Ala
                645                 650                 655

Ala Thr Glu Thr Gln Ser Ser Leu Thr Ile Leu
            660                 665

<210> SEQ ID NO 34
<211> LENGTH: 684
<212> TYPE: PRT
<213> ORGANISM: Artificial Sequence
<220> FEATURE:
<223> OTHER INFORMATION: Synthetic construct

<400> SEQUENCE: 34

Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
                115                 120                 125

Thr Val Pro Asn Pro Tyr Asn Leu Leu Ser Gly Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asn Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Lys Ala Arg Lys Glu Ala
        275                 280                 285

Ile Leu Ser Ile Pro Val Pro Lys Asn Pro Arg Gln Val Arg Glu Phe
    290                 295                 300

Leu Gly Thr Ala Gly Tyr Cys Arg Leu Trp Ile Pro Gly Phe Ala Glu
305                 310                 315                 320

Leu Ala Ala Pro Leu Tyr Pro Leu Thr Arg Pro Gly Thr Leu Phe Gln
                325                 330                 335

Trp Gly Thr Glu Gln Gln Leu Ala Phe Glu Asn Ile Arg Lys Ala Leu
            340                 345                 350

Leu Ser Ser Pro Ala Leu Gly Leu Pro Asp Ile Thr Lys Pro Phe Glu
        355                 360                 365

Leu Phe Ile Asp Glu Asn Ser Gly Phe Ala Lys Gly Val Leu Val Gln
    370                 375                 380

Lys Leu Gly Pro Trp Lys Arg Pro Val Ala Tyr Leu Ser Lys Lys Leu
385                 390                 395                 400

Asp Thr Val Ala Ser Gly Trp Pro Pro Cys Leu Arg Met Val Ala Ala
                405                 410                 415

Ile Ala Ile Leu Val Lys Asp Ala Gly Lys Leu Thr Leu Gly Gln Pro
            420                 425                 430

Leu Thr Ile Leu Thr Ser His Pro Val Glu Ala Leu Val Arg Gln Pro
        435                 440                 445

Pro Asn Lys Trp Leu Ser Asn Ala Arg Met Thr His Tyr Gln Ala Met
450                 455                 460

Leu Leu Asp Ala Glu Arg Val His Phe Gly Pro Thr Val Ser Leu Asn
465                 470                 475                 480

Pro Ala Thr Leu Leu Pro Leu Pro Ser Gly Lys Pro Arg Leu Ser
                485                 490                 495

Pro Asp Leu Ala Glu Thr Met Ala Gln Thr Asp Leu Thr Asp Gln Pro
            500                 505                 510

Leu Pro Asp Ala Asp Leu Thr Trp Tyr Thr Ala Gly Ser Ser Ile Ile
        515                 520                 525

Arg Asn Gly Glu Arg Lys Ala Gly Ala Ala Val Thr Thr Glu Ser Glu

```
                530               535               540
Val Ile Trp Ala Ala Ser Leu Pro Pro Gly Thr Ser Ala Gln Arg Ala
545                 550                 555                 560

Glu Leu Ile Ala Leu Thr Gln Ala Leu Lys Met Ala Lys Gly Lys Lys
                565                 570                 575

Leu Thr Val Tyr Thr Asp Ser Arg Tyr Ala Phe Ala Thr Ala His Val
                580                 585                 590

His Gly Glu Ile Tyr Arg Arg Gly Leu Leu Thr Ser Glu Gly Lys
                595                 600                 605

Glu Ile Lys Asn Lys Asn Glu Ile Leu Ala Leu Leu Glu Ala Leu Phe
610                 615                 620

Leu Pro Lys Arg Leu Ser Ile Ile Tyr Cys Pro Gly His Gln Lys Gly
625                 630                 635                 640

Asp Ser Pro Gln Ala Lys Gly Asn Arg Leu Ala Asp Asp Thr Ala Lys
                645                 650                 655

Lys Ala Ala Thr Glu Thr Gln Ser Ser Leu Thr Ile Leu Pro Thr Glu
                660                 665                 670

Leu Ile Glu Gly Pro Lys Arg Pro Pro Trp Glu Tyr
                675                 680

<210> SEQ ID NO 35
<211> LENGTH: 684
<212> TYPE: PRT
<213> ORGANISM: Artificial Sequence
<220> FEATURE:
<223> OTHER INFORMATION: Synthetic construct

<400> SEQUENCE: 35

Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
                20                  25                  30

Ala Trp Ala Glu Thr Gly Gly Met Gly Leu Ala Val Arg Gln Ala Pro
            35                  40                  45

Leu Ile Ile Pro Leu Lys Ala Thr Ser Thr Pro Val Ser Ile Lys Gln
        50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Pro Pro Ser His
130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asn Glu Ala Leu His Arg Asp Leu
        195                 200                 205

Ala Asp Phe Arg Ile Gln His Pro Asp Leu Ile Leu Leu Gln Tyr Val
```

-continued

```
            210                 215                 220
Asp Asp Leu Leu Leu Ala Ala Thr Arg Thr Glu Cys Leu Glu Gly
225                 230                 235                 240

Thr Lys Ala Leu Leu Glu Thr Leu Gly Asn Lys Gly Tyr Arg Ala Ser
                245                 250                 255

Ala Lys Lys Ala Gln Ile Cys Leu Gln Glu Val Thr Tyr Leu Gly Tyr
                    260                 265                 270

Ser Leu Lys Asp Gly Gln Arg Trp Leu Thr Lys Ala Arg Lys Glu Ala
            275                 280                 285

Ile Leu Ser Ile Pro Val Pro Lys Asn Pro Arg Gln Val Arg Glu Phe
        290                 295                 300

Leu Gly Thr Ala Gly Tyr Cys Arg Leu Trp Ile Pro Gly Phe Ala Glu
305                 310                 315                 320

Leu Ala Ala Pro Leu Tyr Pro Leu Thr Arg Pro Gly Thr Leu Phe Gln
                325                 330                 335

Trp Gly Thr Glu Gln Gln Leu Ala Phe Glu Asn Ile Arg Lys Ala Leu
                340                 345                 350

Leu Ser Ser Pro Ala Leu Gly Leu Pro Asp Ile Thr Lys Pro Phe Glu
            355                 360                 365

Leu Phe Ile Asp Glu Asn Ser Gly Phe Ala Lys Gly Val Leu Val Gln
        370                 375                 380

Lys Leu Gly Pro Trp Lys Arg Pro Val Ala Tyr Leu Ser Lys Lys Leu
385                 390                 395                 400

Asp Thr Val Ala Ser Gly Trp Pro Pro Cys Leu Arg Met Val Ala Ala
                405                 410                 415

Ile Ala Ile Leu Val Lys Asp Ala Gly Lys Leu Thr Leu Gly Gln Pro
                420                 425                 430

Leu Thr Ile Leu Thr Ser His Pro Val Glu Ala Leu Val Arg Gln Pro
            435                 440                 445

Pro Asn Lys Trp Leu Ser Asn Ala Arg Met Thr His Tyr Gln Ala Met
        450                 455                 460

Leu Leu Asp Ala Glu Arg Val His Phe Gly Pro Thr Val Ser Leu Asn
465                 470                 475                 480

Pro Ala Thr Leu Leu Pro Leu Pro Ser Gly Lys Pro Arg Leu Ser
                485                 490                 495

Pro Asp Leu Ala Glu Thr Met Ala Gln Thr Asp Leu Thr Asp Gln Pro
            500                 505                 510

Leu Pro Asp Ala Asp Leu Thr Trp Tyr Thr Gly Gly Ser Ser Phe Ile
        515                 520                 525

Arg Asn Gly Glu Arg Lys Ala Gly Ala Ala Val Thr Thr Glu Ser Glu
        530                 535                 540

Val Ile Trp Ala Ala Ser Leu Pro Pro Gly Thr Ser Ala Gln Arg Ala
545                 550                 555                 560

Glu Leu Ile Ala Leu Thr Gln Ala Leu Lys Met Ala Lys Gly Lys Lys
                565                 570                 575

Leu Thr Val Tyr Thr Asp Ser Arg Tyr Ala Phe Ala Thr Ala His Val
                580                 585                 590

His Gly Glu Ile Tyr Arg Arg Arg Gly Trp Leu Thr Ser Lys Gly Lys
            595                 600                 605

Glu Ile Lys Asn Lys Asn Glu Ile Leu Ala Leu Leu Glu Ala Leu Phe
        610                 615                 620

Leu Pro Lys Arg Leu Ser Ile Ile His Cys Pro Gly His Gln Lys Gly
625                 630                 635                 640
```

-continued

```
Asp Ser Pro Gln Ala Lys Gly Asn Arg Leu Ala Asp Thr Ala Lys
            645                 650                 655

Lys Ala Ala Thr Glu Thr Gln Ser Ser Leu Thr Ile Leu Pro Thr Glu
        660                 665                 670

Leu Ile Glu Gly Pro Lys Arg Pro Pro Trp Glu Tyr
    675                 680

<210> SEQ ID NO 36
<211> LENGTH: 278
<212> TYPE: PRT
<213> ORGANISM: Artificial Sequence
<220> FEATURE:
<223> OTHER INFORMATION: Synthetic construct

<400> SEQUENCE: 36

Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asn Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln
        275

<210> SEQ ID NO 37
<211> LENGTH: 406
<212> TYPE: PRT
<213> ORGANISM: Artificial Sequence
```

<220> FEATURE:
<223> OTHER INFORMATION: Synthetic construct

<400> SEQUENCE: 37

```
Arg Trp Leu Thr Lys Ala Arg Lys Glu Ala Ile Leu Ser Ile Pro Val
1               5                   10                  15

Pro Lys Asn Pro Arg Gln Val Arg Glu Phe Leu Gly Thr Ala Gly Tyr
            20                  25                  30

Cys Arg Leu Trp Ile Pro Gly Phe Ala Glu Leu Ala Ala Pro Leu Tyr
        35                  40                  45

Pro Leu Thr Arg Pro Gly Thr Leu Phe Gln Trp Gly Thr Glu Gln Gln
    50                  55                  60

Leu Ala Phe Glu Asn Ile Arg Lys Ala Leu Leu Ser Ser Pro Ala Leu
65                  70                  75                  80

Gly Leu Pro Asp Ile Thr Lys Pro Phe Glu Leu Phe Ile Asp Glu Asn
                85                  90                  95

Ser Gly Phe Ala Lys Gly Val Leu Val Gln Lys Leu Gly Pro Trp Lys
            100                 105                 110

Arg Pro Val Ala Tyr Leu Ser Lys Lys Leu Asp Thr Val Ala Ser Gly
        115                 120                 125

Trp Pro Pro Cys Leu Arg Met Val Ala Ala Ile Ala Ile Leu Val Lys
    130                 135                 140

Asp Ala Gly Lys Leu Thr Leu Gly Gln Pro Leu Thr Ile Leu Thr Ser
145                 150                 155                 160

His Pro Val Glu Ala Leu Val Arg Gln Pro Pro Asn Lys Trp Leu Ser
                165                 170                 175

Asn Ala Arg Met Thr His Tyr Gln Ala Met Leu Leu Asp Ala Glu Arg
            180                 185                 190

Val His Phe Gly Pro Thr Val Ser Leu Asn Pro Ala Thr Leu Leu Pro
        195                 200                 205

Leu Pro Ser Gly Lys Pro Pro Arg Leu Ser Pro Asp Leu Ala Glu Thr
    210                 215                 220

Met Ala Gln Thr Asp Leu Thr Asp Gln Pro Leu Pro Asp Ala Asp Leu
225                 230                 235                 240

Thr Trp Tyr Thr Ala Gly Ser Ser Ile Ile Arg Asn Gly Glu Arg Lys
                245                 250                 255

Ala Gly Ala Ala Val Thr Thr Glu Ser Glu Val Ile Trp Ala Ala Ser
            260                 265                 270

Leu Pro Pro Gly Thr Ser Ala Gln Arg Ala Glu Leu Ile Ala Leu Thr
        275                 280                 285

Gln Ala Leu Lys Met Ala Lys Gly Lys Lys Leu Thr Val Tyr Thr Asp
    290                 295                 300

Ser Arg Tyr Ala Phe Ala Thr Ala His Val His Gly Glu Ile Tyr Arg
305                 310                 315                 320

Arg Arg Gly Leu Leu Thr Ser Glu Gly Lys Glu Ile Lys Asn Lys Asn
                325                 330                 335

Glu Ile Leu Ala Leu Leu Glu Ala Leu Phe Leu Pro Lys Arg Leu Ser
            340                 345                 350

Ile Ile Tyr Cys Pro Gly His Gln Lys Gly Asp Ser Pro Gln Ala Lys
        355                 360                 365

Gly Asn Arg Leu Ala Asp Asp Thr Ala Lys Lys Ala Ala Thr Glu Thr
    370                 375                 380

Gln Ser Ser Leu Thr Ile Leu Pro Thr Glu Leu Ile Glu Gly Pro Lys
385                 390                 395                 400
```

Arg Pro Pro Trp Glu Tyr
                405

<210> SEQ ID NO 38
<211> LENGTH: 222
<212> TYPE: PRT
<213> ORGANISM: Artificial Sequence
<220> FEATURE:
<223> OTHER INFORMATION: Synthetic construct

<400> SEQUENCE: 38

Met Thr Leu Asn Ile Glu Asp Glu Tyr Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asn Glu Ala Leu His Arg Asp Leu
        195                 200                 205

Ala Asp Phe Arg Ile Gln His Pro Asp Leu Ile Leu Leu Gln
    210                 215                 220

<210> SEQ ID NO 39
<211> LENGTH: 462
<212> TYPE: PRT
<213> ORGANISM: Artificial Sequence
<220> FEATURE:
<223> OTHER INFORMATION: Synthetic construct

<400> SEQUENCE: 39

Tyr Val Asp Asp Leu Leu Leu Ala Ala Ala Thr Arg Thr Glu Cys Leu
1               5                   10                  15

Glu Gly Thr Lys Ala Leu Leu Glu Thr Leu Gly Asn Lys Gly Tyr Arg
            20                  25                  30

Ala Ser Ala Lys Lys Ala Gln Ile Cys Leu Gln Glu Val Thr Tyr Leu
        35                  40                  45

Gly Tyr Ser Leu Lys Asp Gly Gln Arg Trp Leu Thr Lys Ala Arg Lys
    50                  55                  60

Glu Ala Ile Leu Ser Ile Pro Val Pro Lys Asn Pro Arg Gln Val Arg

```
            65                  70                  75                  80
        Glu Phe Leu Gly Thr Ala Gly Tyr Cys Arg Leu Trp Ile Pro Gly Phe
                        85                  90                  95
        Ala Glu Leu Ala Ala Pro Leu Tyr Pro Leu Thr Arg Pro Gly Thr Leu
                    100                 105                 110
        Phe Gln Trp Gly Thr Glu Gln Leu Ala Phe Glu Asn Ile Arg Lys
                115                 120                 125
        Ala Leu Leu Ser Ser Pro Ala Leu Gly Leu Pro Asp Ile Thr Lys Pro
            130                 135                 140
        Phe Glu Leu Phe Ile Asp Glu Asn Ser Gly Phe Ala Lys Gly Val Leu
        145                 150                 155                 160
        Val Gln Lys Leu Gly Pro Trp Lys Arg Pro Val Ala Tyr Leu Ser Lys
                        165                 170                 175
        Lys Leu Asp Thr Val Ala Ser Gly Trp Pro Pro Cys Leu Arg Met Val
                    180                 185                 190
        Ala Ala Ile Ala Ile Leu Val Lys Asp Ala Gly Lys Leu Thr Leu Gly
                195                 200                 205
        Gln Pro Leu Thr Ile Leu Thr Ser His Pro Val Glu Ala Leu Val Arg
            210                 215                 220
        Gln Pro Pro Asn Lys Trp Leu Ser Asn Ala Arg Met Thr His Tyr Gln
        225                 230                 235                 240
        Ala Met Leu Leu Asp Ala Glu Arg Val His Phe Gly Pro Thr Val Ser
                        245                 250                 255
        Leu Asn Pro Ala Thr Leu Leu Pro Leu Pro Ser Gly Lys Pro Pro Arg
                    260                 265                 270
        Leu Ser Pro Asp Leu Ala Glu Thr Met Ala Gln Thr Asp Leu Thr Asp
                275                 280                 285
        Gln Pro Leu Pro Asp Ala Asp Leu Thr Trp Tyr Thr Gly Gly Ser Ser
            290                 295                 300
        Phe Ile Arg Asn Gly Glu Arg Lys Ala Gly Ala Ala Val Thr Thr Glu
        305                 310                 315                 320
        Ser Glu Val Ile Trp Ala Ala Ser Leu Pro Pro Gly Thr Ser Ala Gln
                        325                 330                 335
        Arg Ala Glu Leu Ile Ala Leu Thr Gln Ala Leu Lys Met Ala Lys Gly
                    340                 345                 350
        Lys Lys Leu Thr Val Tyr Thr Asp Ser Arg Tyr Ala Phe Ala Thr Ala
                355                 360                 365
        His Val His Gly Glu Ile Tyr Arg Arg Arg Gly Trp Leu Thr Ser Lys
            370                 375                 380
        Gly Lys Glu Ile Lys Asn Lys Asn Glu Ile Leu Ala Leu Leu Glu Ala
        385                 390                 395                 400
        Leu Phe Leu Pro Lys Arg Leu Ser Ile Ile His Cys Pro Gly His Gln
                        405                 410                 415
        Lys Gly Asp Ser Pro Gln Ala Lys Gly Asn Arg Leu Ala Asp Asp Thr
                    420                 425                 430
        Ala Lys Lys Ala Ala Thr Glu Thr Gln Ser Ser Leu Thr Ile Leu Pro
                435                 440                 445
        Thr Glu Leu Ile Glu Gly Pro Lys Arg Pro Pro Trp Glu Tyr
            450                 455                 460

<210> SEQ ID NO 40
<211> LENGTH: 707
<212> TYPE: PRT
<213> ORGANISM: Artificial Sequence
```

<220> FEATURE:
<223> OTHER INFORMATION: Synthetic construct

<400> SEQUENCE: 40

```
Met Gly Ser Ser His His His His His His Ser Ser Gly Leu Val Pro
1               5                   10                  15

Arg Gly Ser His Met Thr Leu Asn Ile Glu Asp Glu Tyr Arg Leu His
            20                  25                  30

Glu Thr Ser Lys Glu Pro Asp Val Ser Leu Gly Ser Thr Trp Leu Ser
        35                  40                  45

Asp Phe Pro Gln Ala Trp Ala Glu Thr Gly Gly Met Gly Leu Ala Val
    50                  55                  60

Arg Gln Ala Pro Leu Ile Ile Pro Leu Lys Ala Thr Ser Thr Pro Val
65                  70                  75                  80

Ser Ile Lys Gln Tyr Pro Met Ser Gln Glu Ala Arg Leu Gly Ile Lys
                85                  90                  95

Pro His Ile Gln Arg Leu Leu Asp Gln Gly Ile Leu Val Pro Cys Gln
            100                 105                 110

Ser Pro Trp Asn Thr Pro Leu Leu Pro Val Lys Lys Pro Gly Thr Asn
        115                 120                 125

Asp Tyr Arg Pro Val Gln Asp Leu Arg Glu Val Asn Lys Arg Val Glu
    130                 135                 140

Asp Ile His Pro Thr Val Pro Asn Pro Tyr Asn Leu Leu Ser Gly Pro
145                 150                 155                 160

Pro Pro Ser His Gln Trp Tyr Thr Val Leu Asp Leu Lys Asp Ala Phe
                165                 170                 175

Phe Cys Leu Arg Leu His Pro Thr Ser Gln Pro Leu Phe Ala Phe Glu
            180                 185                 190

Trp Arg Asp Pro Glu Met Gly Ile Ser Gly Gln Leu Thr Trp Thr Arg
        195                 200                 205

Leu Pro Gln Gly Phe Lys Asn Ser Pro Thr Leu Phe Asn Glu Ala Leu
    210                 215                 220

His Arg Asp Leu Ala Asp Phe Arg Ile Gln His Pro Asp Leu Ile Leu
225                 230                 235                 240

Leu Gln Tyr Val Asp Asp Leu Leu Leu Ala Ala Thr Ser Glu Leu Asp
                245                 250                 255

Cys Gln Gln Gly Thr Arg Ala Leu Leu Gln Thr Leu Gly Asn Leu Gly
            260                 265                 270

Tyr Arg Ala Ser Ala Lys Lys Ala Gln Ile Cys Gln Lys Gln Val Lys
        275                 280                 285

Tyr Leu Gly Tyr Leu Leu Lys Glu Gly Gln Arg Trp Leu Thr Lys Ala
    290                 295                 300

Arg Lys Glu Ala Ile Leu Ser Ile Pro Val Pro Lys Asn Pro Arg Gln
305                 310                 315                 320

Val Arg Glu Phe Leu Gly Thr Ala Gly Tyr Cys Arg Leu Trp Ile Pro
                325                 330                 335

Gly Phe Ala Glu Leu Ala Ala Pro Leu Tyr Pro Leu Thr Arg Pro Gly
            340                 345                 350

Thr Leu Phe Gln Trp Gly Thr Glu Gln Gln Leu Ala Phe Glu Asn Ile
        355                 360                 365

Arg Lys Ala Leu Leu Ser Ser Pro Ala Leu Gly Leu Pro Asp Ile Thr
    370                 375                 380

Lys Pro Phe Glu Leu Phe Ile Asp Glu Asn Ser Gly Phe Ala Lys Gly
385                 390                 395                 400
```

Val Leu Val Gln Lys Leu Gly Pro Trp Lys Arg Pro Val Ala Tyr Leu
            405                 410                 415

Ser Lys Lys Leu Asp Thr Val Ala Ser Gly Trp Pro Pro Cys Leu Arg
        420                 425                 430

Met Val Ala Ala Ile Ala Ile Leu Val Lys Asp Ala Gly Lys Leu Thr
            435                 440                 445

Leu Gly Gln Pro Leu Thr Ile Leu Thr Ser His Pro Val Glu Ala Leu
        450                 455                 460

Val Arg Gln Pro Pro Asn Lys Trp Leu Ser Asn Ala Arg Met Thr His
465                 470                 475                 480

Tyr Gln Ala Met Leu Leu Asp Ala Glu Arg Val His Phe Gly Pro Thr
                485                 490                 495

Val Ser Leu Asn Pro Ala Thr Leu Leu Pro Leu Pro Ser Gly Lys Pro
            500                 505                 510

Pro Arg Leu Ser Pro Asp Leu Ala Glu Thr Met Ala Gln Thr Asp Leu
        515                 520                 525

Thr Asp Gln Pro Leu Pro Asp Ala Asp Leu Thr Trp Tyr Thr Ala Gly
        530                 535                 540

Ser Ser Ile Ile Arg Asn Gly Glu Arg Lys Ala Gly Ala Ala Val Thr
545                 550                 555                 560

Thr Glu Ser Glu Val Ile Trp Ala Ala Ser Leu Pro Pro Gly Thr Ser
                565                 570                 575

Ala Gln Arg Ala Glu Leu Ile Ala Leu Thr Gln Ala Leu Lys Met Ala
            580                 585                 590

Lys Gly Lys Lys Leu Thr Val Tyr Thr Asp Ser Arg Tyr Ala Phe Ala
        595                 600                 605

Thr Ala His Val His Gly Glu Ile Tyr Arg Arg Arg Gly Leu Leu Thr
        610                 615                 620

Ser Glu Gly Lys Glu Ile Lys Asn Lys Asn Glu Ile Leu Ala Leu Leu
625                 630                 635                 640

Glu Ala Leu Phe Leu Pro Lys Arg Leu Ser Ile Ile Tyr Cys Pro Gly
                645                 650                 655

His Gln Lys Gly Asp Ser Pro Gln Ala Lys Gly Asn Arg Leu Ala Asp
            660                 665                 670

Asp Thr Ala Lys Lys Ala Ala Thr Glu Thr Gln Ser Ser Leu Thr Ile
        675                 680                 685

Leu Pro Thr Glu Leu Ile Glu Gly Pro Lys Arg Pro Pro Trp Glu Tyr
        690                 695                 700

Ala Ala Ala
705

<210> SEQ ID NO 41
<211> LENGTH: 707
<212> TYPE: PRT
<213> ORGANISM: Artificial Sequence
<220> FEATURE:
<223> OTHER INFORMATION: Synthetic construct

<400> SEQUENCE: 41

Met Gly Ser Ser His His His His His His Ser Ser Gly Leu Val Pro
1               5                   10                  15

Arg Gly Ser His Met Thr Leu Asn Ile Glu Asp Glu Tyr Arg Leu His
                20                  25                  30

Glu Thr Ser Lys Glu Pro Asp Val Ser Leu Gly Ser Thr Trp Leu Ser
            35                  40                  45

```
Asp Phe Pro Gln Ala Trp Ala Glu Thr Gly Gly Met Gly Leu Ala Val
 50                  55                  60

Arg Gln Ala Pro Leu Ile Ile Pro Leu Lys Ala Thr Ser Thr Pro Val
 65                  70                  75                  80

Ser Ile Lys Gln Tyr Pro Met Ser Gln Glu Ala Arg Leu Gly Ile Lys
                 85                  90                  95

Pro His Ile Gln Arg Leu Leu Asp Gln Gly Ile Leu Val Pro Cys Gln
                100                 105                 110

Ser Pro Trp Asn Thr Pro Leu Leu Pro Val Lys Lys Pro Gly Thr Asn
            115                 120                 125

Asp Tyr Arg Pro Val Gln Asp Leu Arg Glu Val Asn Lys Arg Val Glu
130                 135                 140

Asp Ile His Pro Thr Val Pro Asn Pro Tyr Asn Leu Leu Ser Gly Pro
145                 150                 155                 160

Pro Pro Ser His Gln Trp Tyr Thr Val Leu Asp Leu Lys Asp Ala Phe
                165                 170                 175

Phe Cys Leu Arg Leu His Pro Thr Ser Gln Pro Leu Phe Ala Phe Glu
                180                 185                 190

Trp Arg Asp Pro Glu Met Gly Ile Ser Gly Gln Leu Thr Trp Thr Arg
                195                 200                 205

Leu Pro Gln Gly Phe Lys Asn Ser Pro Thr Leu Phe Asn Glu Ala Leu
    210                 215                 220

His Arg Asp Leu Ala Asp Phe Arg Ile Gln His Pro Asp Leu Ile Leu
225                 230                 235                 240

Leu Gln Tyr Val Asp Asp Leu Leu Leu Ala Ala Thr Arg Thr Glu
                245                 250                 255

Cys Leu Glu Gly Thr Lys Ala Leu Leu Glu Thr Leu Gly Asn Lys Gly
                260                 265                 270

Tyr Arg Ala Ser Ala Lys Lys Ala Gln Ile Cys Leu Gln Glu Val Thr
    275                 280                 285

Tyr Leu Gly Tyr Ser Leu Lys Asp Gly Gln Arg Trp Leu Thr Lys Ala
    290                 295                 300

Arg Lys Glu Ala Ile Leu Ser Ile Pro Val Pro Lys Asn Pro Arg Gln
305                 310                 315                 320

Val Arg Glu Phe Leu Gly Thr Ala Gly Tyr Cys Arg Leu Trp Ile Pro
                325                 330                 335

Gly Phe Ala Glu Leu Ala Ala Pro Leu Tyr Pro Leu Thr Arg Pro Gly
                340                 345                 350

Thr Leu Phe Gln Trp Gly Thr Glu Gln Gln Leu Ala Phe Glu Asn Ile
                355                 360                 365

Arg Lys Ala Leu Leu Ser Ser Pro Ala Leu Gly Leu Pro Asp Ile Thr
    370                 375                 380

Lys Pro Phe Glu Leu Phe Ile Asp Glu Asn Ser Gly Phe Ala Lys Gly
385                 390                 395                 400

Val Leu Val Gln Lys Leu Gly Pro Trp Lys Arg Pro Val Ala Tyr Leu
                405                 410                 415

Ser Lys Lys Leu Asp Thr Val Ala Ser Gly Trp Pro Pro Cys Leu Arg
                420                 425                 430

Met Val Ala Ala Ile Ala Ile Leu Val Lys Asp Ala Gly Lys Leu Thr
                435                 440                 445

Leu Gly Gln Pro Leu Thr Ile Leu Thr Ser His Pro Val Glu Ala Leu
    450                 455                 460
```

```
Val Arg Gln Pro Pro Asn Lys Trp Leu Ser Asn Ala Arg Met Thr His
465                 470                 475                 480

Tyr Gln Ala Met Leu Leu Asp Ala Glu Arg Val His Phe Gly Pro Thr
                485                 490                 495

Val Ser Leu Asn Pro Ala Thr Leu Leu Pro Leu Pro Ser Gly Lys Pro
                500                 505                 510

Pro Arg Leu Ser Pro Asp Leu Ala Glu Thr Met Ala Gln Thr Asp Leu
            515                 520                 525

Thr Asp Gln Pro Leu Pro Asp Ala Asp Leu Thr Trp Tyr Thr Gly Gly
        530                 535                 540

Ser Ser Phe Ile Arg Asn Gly Glu Arg Lys Ala Gly Ala Ala Val Thr
545                 550                 555                 560

Thr Glu Ser Glu Val Ile Trp Ala Ala Ser Leu Pro Pro Gly Thr Ser
                565                 570                 575

Ala Gln Arg Ala Glu Leu Ile Ala Leu Thr Gln Ala Leu Lys Met Ala
                580                 585                 590

Lys Gly Lys Lys Leu Thr Val Tyr Thr Asp Ser Arg Tyr Ala Phe Ala
            595                 600                 605

Thr Ala His Val His Gly Glu Ile Tyr Arg Arg Arg Gly Trp Leu Thr
        610                 615                 620

Ser Lys Gly Lys Glu Ile Lys Asn Lys Asn Glu Ile Leu Ala Leu Leu
625                 630                 635                 640

Glu Ala Leu Phe Leu Pro Lys Arg Leu Ser Ile Ile His Cys Pro Gly
                645                 650                 655

His Gln Lys Gly Asp Ser Pro Gln Ala Lys Gly Asn Arg Leu Ala Asp
            660                 665                 670

Asp Thr Ala Lys Lys Ala Ala Thr Glu Thr Gln Ser Ser Leu Thr Ile
        675                 680                 685

Leu Pro Thr Glu Leu Ile Glu Gly Pro Lys Arg Pro Pro Trp Glu Tyr
    690                 695                 700

Ala Ala Ala
705

<210> SEQ ID NO 42
<211> LENGTH: 8
<212> TYPE: PRT
<213> ORGANISM: Artificial Sequence
<220> FEATURE:
<223> OTHER INFORMATION: Synthetic construct

<400> SEQUENCE: 42

Asp Tyr Lys Asp Asp Asp Asp Lys
1               5
```

REVERSE TRANSCRIPTASES AND USES THEREOF

CROSS-REFERENCE TO RELATED PATENT APPLICATIONS

The present patent application claims benefit of priority to U.S. Provisional Patent Application No. 62/459,974, filed on Feb. 16, 2017, which is incorporated by reference for all purposes.

REFERENCE TO A "SEQUENCE LISTING" SUBMITTED AS ASCII TEXT FILES VIA EFS-WEB

The Sequence Listing written in file 094260-1076456-112710US_SequenceListing.txt created on Feb. 2, 2018, 184,742 bytes, machine format IBM-PC, MS-Windows operating system, in accordance with 37 C.F.R. §§ 1.821- to 1.825, is hereby incorporated by reference in its entirety for all purposes.

BACKGROUND OF THE INVENTION

The detection, analysis, transcription, and amplification of nucleic acids are frequently-used procedures in modern molecular biology. DNA polymerases are useful for detection and amplification of DNA or RNA. The application of such procedures for RNA analysis can involve the investigation of gene expression, diagnosis of infectious agents or genetic diseases, and the generation of cDNA, to name but a few applications. The reverse transcription of RNA thus has many uses. In some instances, the reverse transcriptase is followed by polymerase chain reaction amplification which can be used for rapid detection and quantification of RNA.

BRIEF SUMMARY OF THE INVENTION

In some embodiments, a hybrid reverse transcriptase is provided comprising a finger domain, a palm domain, a thumb domain, a connection domain and an RNase H domain, wherein at least one of said domains is a mouse leukemia virus reverse transcriptase (MLVRT) and other of said domains are from feline leukemia virus reverse transcriptase (FLVRT).

In some embodiments, the hybrid reverse transcriptase comprises: a portion of mouse leukemia virus reverse transcriptase (MLVRT) comprising finger and palm domains linked to a portion of feline leukemia virus reverse transcriptase (FLVRT) comprising thumb, connection, and RNase H domains. In some embodiments, the portion of the MLVRT has a carboxyl terminus and the carboxyl terminus is linked directly to an amino terminus of the portion of the FLVRT. In some embodiments, the portion of the MLVRT has a carboxyl terminus and the carboxyl terminus is linked to an amino terminus of the portion of the FLVRT via a linking amino acid sequence of 1-100 amino acids. In some embodiments, the portion of the MLVRT is at least 95% identical to SEQ ID NO:1 and the portion of the FLVRT is at least 95% identical to SEQ ID NO:5.

In some embodiments, the portion of the MLVRT comprises SEQ ID NO:1 and the portion of the FLVRT comprises SEQ ID NO:5. In some embodiments, the portion of the FLVRT comprises SEQ ID NO:6 or SEQ ID NO:10. In some embodiments, the portion of the FLVRT comprises SEQ ID NO:7, SEQ ID NO:8, SEQ ID NO:9, or SEQ ID NO:11.

In some embodiments, the portion of the MLVRT comprises SEQ ID NO:2. In some embodiments, the portion of the MLVRT comprises SEQ ID NO:3 or SEQ ID NO:4.

In some embodiments, the portion of the MLVRT comprises SEQ ID NO:4 and the portion of the FLVRT comprises SEQ ID NO:7; or
the portion of the MLVRT comprises SEQ ID NO:4 and the portion of the FLVRT comprises SEQ ID NO:8; or
the portion of the MLVRT comprises SEQ ID NO:4 and the portion of the FLVRT comprises SEQ ID NO:9; or
the portion of the MLVRT comprises SEQ ID NO:3 and the portion of the FLVRT comprises SEQ ID NO:11; or
the portion of the MLVRT comprises SEQ ID NO:3 and the portion of the FLVRT comprises SEQ ID NO:10; or
the portion of the MLVRT comprises SEQ ID NO:4 and the portion of the FLVRT comprises SEQ ID NO:13.

In some embodiments, the hybrid reverse transcriptase comprises a sequence substantially (e.g., at least 70%, 80%, 85%, 90%, or 95%) identical to SEQ ID NO: 14, 15, 16, 17, 18, 19, 34, or 35.

In some embodiments, the hybrid reverse transcriptase comprises a portion of feline leukemia virus reverse transcriptase (FLVRT) comprising finger and palm domains linked to a portion of mouse leukemia virus reverse transcriptase (MLVRT) comprising RNase H domains. In some embodiments, the portion of MLVRT comprises thumb, connection, and RNase H domains. In some embodiments, the portion of FLVRT comprises a sequence at least 95% identical to SEQ ID NO:26; and the portion of MLVRT comprises a sequence at least 95% identical to SEQ ID NO:28. In some embodiments, the hybrid reverse transcriptase comprises a sequence substantially (e.g., at least 70%, 80%, 85%, 90%, or 95%) identical to SEQ ID NO:30.

In some embodiments, the portion of FLVRT comprises finger, palm, thumb and connection domains. In some embodiments, the portion of FLVRT comprises a sequence substantially (e.g., at least 70%, 80%, 85%, 90%, or 95%) identical to SEQ ID NO:27; and the portion of MLVRT comprises a sequence substantially (e.g., at least 70%, 80%, 85%, 90%, or 95%) identical to SEQ ID NO:29. In some embodiments, the hybrid reverse transcriptase comprises a sequence substantially (e.g., at least 70%, 80%, 85%, 90%, or 95%) identical to SEQ ID NO:31.

In some embodiments, the hybrid reverse transcriptase as described above or elsewhere herein has at least one mutation that improves thermostability. In some embodiments, the at least one mutation at a position corresponding to L139, D200, N479, D522, F526, H592, L601, E605, and H632 in SEQ ID NO:34.

Also provided is a nucleic acid comprising a polynucleotide encoding the hybrid reverse transcriptase as described above or elsewhere herein. In some embodiments, the nucleic acid further comprises a (optionally heterologous) promoter operably linked to the polynucleotide.

Also provided is an expression vector comprising the nucleic acid as described above or elsewhere herein. Also provided is a cell comprising the expression vector. In some embodiments, the cell is a bacterial cell.

Also provided is a reaction mixture comprising: an RNA or DNA template; and the hybrid reverse transcriptase as described above or elsewhere herein. In some embodiments, the reaction mixture further comprises at least one oligonucleotide primer and/or deoxynucleotides.

Also provided is a method of performing reverse transcription. In some embodiments, the method comprises contacting the hybrid reverse transcriptase as described above or elsewhere herein in a reaction mixture with a template RNA and a primer that hybridizes to the template RNA under conditions such that the hybrid reverse transcriptase extends the primer in a template RNA-dependent manner to form a cDNA In some embodiments, the conditions comprise an extension step between 42-60° C.

Also provided is a kit comprising the hybrid reverse transcriptase as described above or elsewhere herein. In some embodiments, the kit further comprises a DNA polymerase.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization described below are those well-known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well-known and commonly employed in the art. Standard techniques, or modifications thereof, are used for chemical syntheses and chemical analyses.

"Heterologous", when used with reference to portions of a protein, indicates that the protein comprises two or more domains that are not found in the same relationship to each other in nature. Such a protein, e.g., a fusion protein such as the hybrid RTs described herein, contains two or more sequences covalently linked via a peptide bond or peptide linker sequence arranged to make a new functional protein.

A "primer" refers to a polynucleotide sequence that hybridizes to a sequence on a target nucleic acid and serves as a point of initiation of nucleic acid synthesis. Primers can be of a variety of lengths and are often less than 50 nucleotides in length, for example 12-30 nucleotides, in length. The length and sequences of primers for use in PCR can be designed based on principles known to those of skill in the art, see, e.g., Innis et al., supra.

"Polymerase" refers to an enzyme that performs template-directed synthesis of polynucleotides. The term encompasses both the full length polypeptide and a domain that has polymerase activity.

A "template" refers to a polynucleotide sequence that comprises the polynucleotide to be amplified, optionally flanked by one or two primer hybridization sites.

As used herein, "nucleic acid" means DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, points of attachment and functionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications such as capping with a fluorophore (e.g., quantum dot) or another moiety.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, .gamma.-carboxyglutamate, and O-phosphoserine. Amino acid analogs refers to compounds that have the same basic chemical structure as a naturally occurring amino acid, i.e., a carbon atom that is bound to a hydrogen atom, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "promoter" refers to regions or sequence located upstream and/or downstream from the start of transcription and which are involved in recognition and binding of RNA polymerase and other proteins to initiate transcription.

A "vector" refers to a polynucleotide, which when independent of the host chromosome, is capable replication in a host organism. Preferred vectors include plasmids and typically have an origin of replication. Vectors can comprise, e.g., transcription and translation terminators, transcription and translation initiation sequences, and promoters useful for regulation of the expression of the particular nucleic acid.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, Computer Applic. Biol. Sci. 4:11-17 (1988) e.g., as implemented in the program PC/GENE (Intelligenetics, Mountain View, Calif., USA).

Sequences are "substantially identical" to each other if they have a specified percentage of nucleotides or amino acid residues that are the same (e.g., at least 60%, 65%, 70%, 75%, 80%, 85%, 90%, 91%, 92%, 93%, 94%, 95%, 96%, 97%, 98%, or 99% identity over a specified region or when not specified the whole sequence (SEQ ID NO)), when compared and aligned for maximum correspondence over a comparison window, or designated region as measured using one of the following sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Accelrys), or by manual alignment and visual inspection.

Percent sequence identity and sequence similarity is determined using the BLAST algorithm, which is described in Altschul et al., J. Mol. Biol. 215:403-410 (1990). Software for performing BLAST analyses is publicly available through the National Center for Biotechnology Information (http://www.ncbi.nlm.nih.go-v/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

BRIEF DESCRIPTION OF THE DRAWINGS

FIG. 1 depicts an exemplary soluble fraction SDS-PAGE gel following RT mutant expression.

DETAILED DESCRIPTION OF THE INVENTION

The inventors have discovered that reverse transcriptase (RT) hybrids formed from a mouse leukemia virus reverse transcriptase (MLVRT) and feline leukemia virus reverse transcriptase (FLVRT) have improved solubility compared to FLVRT enzymes. The hybrids described herein are also expected to have improved stability, expression, or a combination thereof compared to at least one of non-hybrid MLVRT or FLVRT enzymes. For example, the inventors have generated hybrid reverse transcriptases comprising a finger domain, a palm domain, a thumb domain, a connection domain and an RNase H domain, wherein at least one of said domains is a mouse leukemia virus reverse transcriptase (MLVRT) and other of said domains are from feline leukemia virus reverse transcriptase (FLVRT). As discussed in more detail, the inventors have generated hybrids in which the finger and palm domains are either FLVRT or MLVRT sequences with at least some of the remainder being from the alternative enzyme.

Polypeptides

Provided herein are hybrid reverse transcriptases (RTs) that have the five RT domains (from amino to carboxyl: finger, palm, thumb, connection, and RNase H domains) where at least one (e.g., 1, 2, 3, or 4) of those domains are from MLVRT and the remaining domain(s) are from FLVRT. The structure of MLVRT and finger, palm, thumb, connection, and RNase H domains are described in, e.g., Das and Georgiadis, Structure 12:819-829 (2004). The resulting hybrid RTs have improved expression (e.g., in *E. coli*) compared to an RT where all of the domains are from FLVRT (i.e., wildtype FLVRT) while in some embodiments having improved accuracy compared to MLVRT.

MLV-FLV Hybrids

In some embodiments, the hybrid RT comprises the finger and palm domains of MLVRT linked to the thumb, connection, and RNase H domains of FLVRT. Exemplary portions of MLVRT that comprise finger and palm domains include, for example, SEQ ID NO:1 or a substantially identical sequence thereof. In some embodiments, the portion of MLVRT that comprises finger and palm domains comprises SEQ ID NO:2 or a sequence substantially identical thereto. The above-described MLVRT portion can be linked to a portion of FLVRT that comprises the thumb, connection, and RNase H domains. An exemplary portion of FLVRT that comprises the thumb, connection, and RNase H domains is SEQ ID NO: 5 or a substantially identical sequence thereof. In some embodiments, the portion of FLVRT that comprises the thumb, connection, and RNase H domains is SEQ ID NO: 6 or a substantially identical sequence thereof or SEQ ID NO:10 or a substantially identical sequence thereof. Exemplary hybrid RTs can comprise, for example SEQ ID NO:1 or SEQ ID NO:2 any of SEQ ID NO:5, SEQ ID NO:6, or SEQ ID NO:10. In some embodiments, the hybrid RT comprises one of SEQ ID NOs: 14, 15, 16, 17, 18, or 19 or a substantially identical sequence thereof.

FLV-MLV Hybrids

In some embodiments, the hybrid RT comprises at least the finger and palm domains of FLVRT linked to the thumb and connection domains of either FLVRT or MLVRT, which in turn is linked to the RNase H domains of MLVRT. In some embodiments, the hybrid RT comprises finger and palm domains of FLVRT and thumb, connection, and RNase H domains of MLVRT. Exemplary portions of FLVRT that comprise finger and palm domains include, for example, SEQ ID NO:26 or a substantially identical sequence thereof. Exemplary portions of MLVRT that comprise thumb, connection, and RNase H domains include, for example, SEQ ID NO:28 or a substantially identical sequence thereof.

In some embodiments, the hybrid RT comprises finger, palm, thumb, and connection domains of FLVRT and RNase H domain of MLVRT. Exemplary portions of FLVRT that comprise finger, palm, thumb, and connection domains include, for example, SEQ ID NO:27 or a substantially identical sequence thereof. Exemplary portions of MLVRT that comprise the RNase H domain include, for example, SEQ ID NO:29 or a substantially identical sequence thereof. In some embodiments, the hybrid RT comprises one of SEQ ID NO: 30 or 31, or a substantially identical sequence thereof.

Any of the hybrid RTs described herein can include further amino acids at the amino or carboxyl terminus. Exemplary additional amino acid sequences can include, for example, epitope tags or other tags that allow for purification of the proteins or whose underlying codons allow for cloning sites. Such tags can be fused at either end of the hybrid RT as most convenient for purification. Examples of such tags include, but are not limited to, poly-histidine sequences or FLAG-tag. Various linker sequences can also be include to link such tags or other sequences to the hybrid RT sequence. Linkers can include, for example glycine, serine or other amino acids that do not significantly interfere with protein folding such that the activity of the hybrid RT is not harmed. The linker sequences can also include protease cleavage sequences such that the tag can be removed by a protease or other cleavage mechanism, optionally once the hybrid RT has been purified (e.g., using the tag). In some embodiments, the hybrid RT includes one or more (e.g., 2-20, 2-5, e.g., 3) alanines at the carboxyl terminus.

Thermostable Mutations

As noted herein, any hybrid RTs as described herein can include one or more mutation that improves the thermostability (i.e., ability to remain active during or after exposure to temperatures over 37° C., e.g., 42-60° C.) of the enzyme. Exemplary mutations include one or more (e.g., 2, 3, 4, 5, 6, or more) mutation at a position corresponding to L139 (including but not limited to L139P), D200 (including but not limited to D200N), N479 (including but not limited to N479D), D522 (including but not limited to, D522G, D522N, or D522A), F526 (including but not limited to F526I), H592 (including but not limited to H592K), L601 (including but not limited to L601W), E605 (including but not limited to E605K), and H632 (including but not limited to H632Y) in SEQ ID NO:34. It should be understood that such position designations do not indicate the number of amino acids in the claimed molecule per se, but indicate where in the claimed molecule the residue occurs when the claimed molecule sequence is maximally aligned with SEQ ID NO:34.

Linking of Portions

Two portions of different RTs as described herein as described can be joined via a linker by methods well known to those of skill in the art. These methods can include either recombinant and chemical methods.

Linking portions of different RTs may also comprise a peptide bond formed between moieties that are separately synthesized by standard peptide synthesis chemistry or recombinant methods. Alternatively, in some embodiments, the coding sequences of each portion in the hybrid RT are directly joined and expressed as a fusion protein. Alternatively, an amino acid linker sequence may also be encoded in the polypeptide coding sequence and employed to separate the first and second RT portions by a distance sufficient to ensure that each polypeptide folds into its secondary and tertiary structures. Such an amino acid linker sequence is incorporated into the fusion protein using recombinant techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Typical peptide linker sequences contain Gly, Ser, Val and Thr residues. Other near neutral amino acids, such as Ala can also be used in the linker sequence. Amino acid sequences which may be usefully employed as linkers include those disclosed in Maratea et al. (1985) Gene 40:39-46; Murphy et al. (1986) Proc. Natl. Acad. Sci. USA 83:8258-8262; U.S. Pat. Nos. 4,935,233 and 4,751,180. The linker sequence may generally be from 1 to about 50 amino acids in length, e.g., 3, 4, 6, or 10 amino acids in length, but can be 100 or 200 amino acids in length. Linker sequences are not necessarily required.

Chemical linking can be performed, for example, as described in Bioconjugate Techniques, Hermanson, Ed., Academic Press (1996). Joining can include, for example, derivitization for the purpose of linking the two proteins to each other, either directly or through a linking compound, by methods that are well known in the art of protein chemistry. For example, in one chemical conjugation embodiment, the means of linking the catalytic domain and the nucleic acid binding domain comprises a heterobifunctional-coupling reagent which ultimately contributes to formation of an intermolecular disulfide bond between the two moieties. Other types of coupling reagents that are useful in this capacity for the present invention are described, for example, in U.S. Pat. No. 4,545,985. Alternatively, an intermolecular disulfide may conveniently be formed between cysteines in each moiety, which occur naturally or are inserted by genetic engineering. The means of linking moieties may also use thioether linkages between heterobifunctional crosslinking reagents or specific low pH cleavable crosslinkers or specific protease cleavable linkers or other cleavable or noncleavable chemical linkages. Other chemical linkers include carbohydrate linkers, lipid linkers, fatty acid linkers, polyether linkers, e.g., PEG, etc. For example, poly(ethylene glycol) linkers are available from Shearwater Polymers, Inc. Huntsville, Ala. These linkers optionally have amide linkages, sulfhydryl linkages, or heterobifunctional linkages. The linking group can be a chemical cross-linking agent, including, for example, succinimidyl-(N-maleimidomethyl)-cyclohexane-1-carboxylate (SMCC). The linking group can also be an additional amino acid sequence(s), including but not limited to, for example, a polyalanine, polyglycine or similarly, linking group.

In some embodiments, nonclassical amino acids or chemical amino acid analogs can be introduced as a substitution or addition into the sequence. Non-classical amino acids include, but are not limited to, the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxy-proline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, N-methyl amino acids, and amino acid analogs in general. Furthermore, the amino acid can be D (dextrorotary) or L (levorotary).

Expression and Purification

Nucleic acids encoding the hybrid RTs can be obtained using routine techniques in the field of recombinant genetics. Basic texts disclosing the general methods of use in this invention include Sambrook and Russell, Molecular Cloning, A Laboratory Manual (3rd ed. 2001); Kriegler, Gene Transfer and Expression: A Laboratory Manual (1990); and Current Protocols in Molecular Biology (Ausubel et al., eds., 1994-1999). Such nucleic acids may also be obtained through in vitro amplification methods such as those described herein and in Berger, Sambrook, and Ausubel, as well as Mullis et al., (1987) U.S. Pat. No. 4,683,202; PCR Protocols A Guide to Methods and Applications (Innis et al., eds) Academic Press Inc. San Diego, Calif. (1990) (Innis); Arnheim & Levinson (Oct. 1, 1990) C&EN 36-47; The Journal Of NIH Research (1991) 3: 81-94; Kwoh et al. (1989) Proc. Natl. Acad. Sci. USA 86: 1173; Guatelli et al. (1990) Proc. Natl. Acad. Sci. USA 87, 1874; Lomeli et al. (1989) J. Clin. Chem., 35: 1826; Landegren et al., (1988) Science 241: 1077-1080; Van Brunt (1990) Biotechnology 8: 291-294; Wu and Wallace (1989) Gene 4: 560; and Barringer et al. (1990) Gene 89: 117, each of which is incorporated by reference in its entirety for all purposes and in particular for all teachings related to amplification methods.

One of skill will recognize that modifications can additionally be made to the hybrid RTs without diminishing their biological activity. Some modifications may be made to facilitate the cloning, expression, or incorporation of a domain into a fusion protein. Such modifications are well known to those of skill in the art and include, for example, the addition of codons at either terminus of the polynucleotide that encodes the binding domain to provide, for example, a methionine added at the amino terminus to provide an initiation site, or additional amino acids (e.g., poly His) placed on either terminus to create conveniently located restriction sites or termination codons or purification sequences.

The hybrid RT polypeptides as described herein can be expressed in a variety of host cells, including *E. coli*, other bacterial hosts, yeasts, filamentous fungi, and various higher eukaryotic cells such as the COS, CHO and HeLa cells lines and myeloma cell lines. Techniques for gene expression in microorganisms are described in, for example, Smith, Gene Expression in Recombinant Microorganisms (Bioprocess Technology, Vol. 22), Marcel Dekker, 1994. Examples of bacteria that are useful for expression include, but are not limited to, *Escherichia, Enterobacter, Azotobacter, Erwinia, Bacillus, Pseudomonas, Klebsielia, Proteus, Salmonella, Serratia, Shigella, Rhizobia, Vitreoscilla*, and *Paracoccus*. Filamentous fungi that are useful as expression hosts include, for example, the following genera: *Aspergillus, Trichoderma, Neurospora, Penicillium, Cephalosporium, Achlya, Podospora, Mucor, Cochliobolus*, and *Pyricularia*. See, e.g., U.S. Pat. No. 5,679,543 and Stahl and Tudzynski, Eds., Molecular Biology in Filamentous Fungi, John Wiley & Sons, 1992. Synthesis of heterologous proteins in yeast is well known and described in the literature. Methods in Yeast Genetics, Sherman, F., et al., Cold Spring Harbor Laboratory, (1982) is a well-recognized work describing the various methods available to produce the enzymes in yeast.

There are many expression systems for producing the polypeptides that are well known to those of ordinary skill in the art. (See, e.g., Gene Expression Systems, Fernandex and Hoeffler, Eds. Academic Press, 1999; Sambrook and Russell, supra; and Ausubel et al, supra.) Typically, the polynucleotide that encodes the polypeptide is placed under the control of a promoter that is functional in the desired host cell. Many different promoters are available and known to one of skill in the art, and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed "expression cassettes." Accordingly, the nucleic acids that encode the joined polypeptides are incorporated for high level expression in a desired host cell.

Expression control sequences that are suitable for use in a particular host cell are often obtained by cloning a gene that is expressed in that cell. Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Change et al., Nature (1977) 198: 1056), the tryptophan (trp) promoter system (Goeddel et al., Nucleic Acids Res. (1980) 8: 4057), the tac promoter (DeBoer, et al., Proc. Natl. Acad. Sci. U.S.A. (1983) 80:21-25); and the lambda-derived PL promoter and N-gene ribosome binding site (Shimatake et al., Nature (1981) 292: 128). The particular promoter system is not critical; any available promoter that functions in prokaryotes and provides the desired level of activity can be used. Standard bacterial expression vectors include plasmids such as pBR322-based plasmids, e.g., pBLUE-SCRIPT™, pSKF, pET23D, lambda-phage derived vectors, and fusion expression systems such as GST and LacZ. Epitope tags can also be added to recombinant proteins to provide convenient methods of isolation, e.g., c-myc, HAtag, 6-His tag, maltose binding protein, VSV-G tag, anti-DYKDDDDK (SEQ ID NO:42) tag, or any such tag, a large number of which are well known to those of skill in the art.

The polypeptides described herein can be expressed intracellularly, or can be secreted from the cell. Intracellular expression often results in high yields. If necessary, the amount of soluble, active fusion polypeptide may be increased by performing refolding procedures (see, e.g., Sambrook et al., supra.; Marston et al., Bio/Technology (1984) 2: 800; Schoner et al., Bio/Technology (1985) 3: 151). Polypeptides can be expressed in a variety of host cells, including *E. coli*, other bacterial hosts, yeast, and various higher eukaryotic cells such as the COS, CHO and HeLa cells lines and myeloma cell lines. The host cells can be mammalian cells, insect cells, or microorganisms, such as, for example, yeast cells, bacterial cells, or fungal cells.

Once expressed, the polypeptides can be purified according to standard procedures of the art, including ammonium sulfate precipitation, affinity columns, column chromatography, gel electrophoresis and the like (see, generally, R. Scopes, Protein Purification, Springer-Verlag, N.Y. (1982), Deutscher, Methods in Enzymology Vol. 182: Guide to Protein Purification. Academic Press, Inc. N.Y. (1990)). Substantially pure compositions of at least about 90 to 95% homogeneity are preferred, and 98 to 99% or more homogeneity are most preferred. Once purified, partially or to homogeneity as desired, the polypeptides may then be used (e.g., as immunogens for antibody production).

To facilitate purification of the polypeptides, the nucleic acids that encode the polypeptides can also include a coding sequence for an epitope or "tag" for which an affinity binding reagent is available. Examples of suitable epitopes include the myc and V-5 reporter genes; expression vectors useful for recombinant production of fusion polypeptides having these epitopes are commercially available (e.g., Invitrogen (Carlsbad Calif.) vectors pcDNA3.1/Myc-His and pcDNA3.1N5-His are suitable for expression in mammalian cells). Additional expression vectors suitable for attaching a tag to the fusion proteins of the invention, and corresponding detection systems are known to those of skill in the art, and several are commercially available (e.g., "FLAG" (Kodak, Rochester N.Y.). Another example of a suitable tag is a polyhistidine sequence, which is capable of binding to metal chelate affinity ligands. Typically, six adjacent histidines are used, although one can use more or less than six. Suitable metal chelate affinity ligands that can serve as the binding moiety for a polyhistidine tag include nitrilo-tri-acetic acid (NTA) (Hochuli, E. (1990) "Purification of recombinant proteins with metal chelating adsorbents" In Genetic Engineering: Principles and Methods, J. K. Setlow, Ed., Plenum Press, N.Y.; commercially available from Qiagen (Santa Clarita, Calif.)).

After biological expression or purification, the hybrid RT polypeptide(s) may possess a conformation substantially different than the native conformations of the constituent polypeptides. In this case, it may be necessary or desirable to denature and reduce the polypeptide and then to cause the polypeptide to re-fold into the preferred conformation. Methods of reducing and denaturing proteins and inducing re-folding are well known to those of skill in the art (See, Debinski et al. (1993) J. Biol. Chem. 268: 14065-14070; Kreitman and Pastan (1993) Bioconjug. Chem. 4: 581-585; and Buchner et al. (1992) Anal. Biochem. 205: 263-270). Debinski et al., for example, describe the denaturation and reduction of inclusion body proteins in guanidine-DTE. The protein is then refolded in a redox buffer containing oxidized glutathione and L-arginine.

V. Methods of Use

Reverse transcription (RT) is an amplification method that copies RNA into DNA. RT reactions can be performed with reaction mixtures as described herein. For example, the invention provides for reverse transcribing one or more RNA (including for example, all RNA in a cell, e.g., to make a cDNA library) under conditions to allow for reverse transcription using a hybrid RT as described herein and generation of a first and optionally second strand cDNA. The RT reaction can be primed with a random primer, an oligo dT, or an RNA-specific primer. Components and conditions for RT reactions are generally known.

If desired, the reactions can further comprise RT-PCR. Standard techniques for performing PCR assays are known in the art (PCR Technology: Principles and Applications for DNA Amplification (Erlich, ed., 1989); PCR Protocols: A Guide to Methods and Applications (Innis, Gelfland, Sninsky, &, White, eds., 1990); Mattila et al., *Nucleic Acids Res.* 19: 4967 (1991); Eckert & Kunkel, PCR Methods and Applications 1: 17 (1991); Wallace et al., Ligase Chain Reaction, in Technologies for Detection of DNA Damage and Mutations, pp. 307-322 (Pfiefer, ed., 1996)). RT and PCR reactions are often used in the same assay and are referred to as RT-PCR. RT-PCR combines reverse transcription of RNA into DNA and subsequent DNA amplification reactions in a single reaction. Optimal reverse transcription, hybridization, and amplification conditions will vary depending upon the sequence composition and length(s) of the primers and target(s) employed, and the experimental method selected by the practitioner. Various guidelines may be used to select appropriate primer sequences and hybridization conditions (see, e.g., Sambrook et al., Molecular Cloning: A Laboratory Manual (2nd ed.) (1989); Ausubel, F. M. et al., eds. (1999) Short Protocols in Molecular Biology, 4th edition, John Wiley & Sons); Ausubel, F. M. et al., eds. (1999-2010) Current Protocols in Molecular Biology, John Wiley & Sons).

In some embodiments, hybrid RTs described herein are used in a reverse transcriptase reaction at a higher temperature than would ordinarily be used. Thus, in embodiments, the some hybrid RTs described herein can be used at, 37° or 42° C., or a temperature greater than 42° C., for example, between 42°-60°, 43°-55°, 45°-56°, 45°-65° C., etc. Higher temperature RT reactions are particularly helpful in situations where the template RNA forms secondary structure at normal RT temperatures (e.g., 37° or 42° C.) that partially or completely inhibit reverse transcription.

VI. Reaction Mixtures

Reaction mixtures comprising the hybrid RT polypeptides described herein are provided. The reaction mixtures can comprise, for example, a target nucleic acid, e.g., an RNA target where reverse transcription is to take place. The reaction mixtures can comprise appropriate nucleotides (e.g., deoxynucleotides (dNTPs) or dideoxynucleotides) and in some embodiments, at least one buffer. Exemplary buffers can include, for example and without limitation, Tris, HEPES, ACES, PIPES, MOPSO, BES, MOPS, TES, TAPSO, POPSO, BICINE, TAPS, or AMPSO. The reaction mixtures can optionally comprise one or more oligonucleotides that function as a primer for template-dependent nucleic acid extension, one or more oligonucleotides that function as a probe (e.g., linked to a label such as a quencher, fluorescent dye, etc.), and/or a double stranded DNA binding dye (e.g., SYBRGREEN). In some embodiments, the reaction mixture will further comprises a separate DNA-dependent DNA polymerase. In some embodiments, the reaction mixture will further comprises magnesium ($Mg^{++}$).

VII. Kits

In one aspect, kits for conducting reverse transcription (and optionally cyclic amplification, e.g., such as PCR) reactions are provided. In some embodiments, such kits include a hybrid RT as described herein, and optionally dNTPs, and at least one buffer. Such kits may also include stabilizers and other additives to increase the efficiency of the amplification reactions. Such kits may also include one or more primers (e.g. poly-T, random hexamers, or specific primers) as well as instructions for conducting reverse transcription reactions using the components of the kits. In some embodiments, the kits will further comprises a separate DNA-dependent DNA polymerase.

EXAMPLES

In order to increase the recombinant FLV RT solubility in *E. coli* cells, hybrid RTs were constructed with part of the RT polypeptide sequence from MLV RT, and part of the RT sequence from FLV RT. Hybrid RT constructs made exhibited improved solubility in *E. coli* cells as demonstrated in FIG. 1.

The hybrid RT FM1 (⅓ FLV-⅔ MLV RT) included a N-terminal sequence of FLV RT from amino acid 1-279, which includes the finger and palm domains, and a C-terminal sequence of MLV RT from amino acid 280-671, which includes the thumb, connection and RNase H domain.

The hybrid RT FM2 (⅔ FLV-⅓ MLV RT) included a N-terminal sequence of FLV RT from amino acid 1-497, which includes the finger, palm, thumb, and connection domains, and a C-terminal sequence of MLV RT from amino acid 498-671, which includes the RNase H domain.

The hybrid RT MF includes a N-terminal sequence of MLV RT from amino acid 1-277, which includes the finger and palm domains, and a C-terminal sequence of FLV RT from amino acid 276-667, which includes the thumb, connection, and RNase H domains.

The hybrid RT MF(P) includes a N-terminal sequence of MLV RT from amino acid 1-221, which includes the finger and palm domains, and a C-terminal sequence of FLV RT from amino acid 221-667, which includes the thumb, connection, and RNase H domains.

Point mutations were introduced into MF and MF(P) hybrid RTs in order to improve the enzyme performance.
Method of Expression of Recombinant RT Constructs:

Fresh LB broth was inoculated with overnight culture of BL21 cells containing expression plasmids in a ratio of 100:1. The cultures were grown at 25° C. for about 6 hr or until OD600 nm=0.6-0.8. IPTG was added to 0.1 mM, and grown O/N for 16 hrs at 16° C. Cells were harvested by collecting the pellet after centrifugation. Cells were resuspended in 200 ml lysis buffer and lysed by sonication. The cell debris was spun down and 200 µl of supernatant was collected. 5 µl sample and 5 µl loading buffer were combined in a PCR strip and heated at 95° C. for 5 min. 6 ul of the samples were loaded onto an SDS-PAGE gel for analysis. Exemplary results are shown in FIG. 1.

The hybrid and mutant proteins were tested for a number of characteristics, which is summarized in part in the following table (blanks indicate the activity was not tested):

|          | Thermostability | Reaction Speed | Processivity | Expression Level |
|----------|-----------------|----------------|--------------|------------------|
| MF5PNAIYC | ++++           |                |              | ++++             |
| MF5PNAIY  | ++++           | ++++           | ++++         | ++++             |
| MF4GC     | ++++           |                |              | ++++             |
| MF4G      | ++++           | ++++           | ++++         | ++++             |
| MF(P)4GC  | ++++           |                |              | ++++             |
| MF(P)4G   | ++++           | +++            | ++++         | ++++             |
| FF4G      | +++            | ++++           | ++++         | ++               |
| FF4GC     | +++            |                |              | ++               |
| MF6PAIKYC | ++++           |                |              | ++++             |
| FF4NDKW   | ++             | +++            | +            | ++               |
| MF(P)4NDKW | ++            | ++++           | ++           | ++++             |
| MF3AIY    | +++            | ++++           | ++++         | ++++             |
| MF4CH     | ++++           | ++++           | ++++         | ++++             |
| FF4CH     | +++            | ++++           | ++           | ++               |
| FF4C      | +++            | ++++           | ++           | ++               |
| MF(P)4C   | ++++           | ++++           | +++          | ++++             |
| FF4NGWN   | ++             | ++++           | ++           | ++               |
| MF(P)4NGWN | ++            | ++++           | ++           | ++++             |
| MD524G    | +++            | ++++           | ++++         | ++++             |

MF(P)4C, FF4C: All "C" at the end represents an additional 15 amino acid C-terminus native sequence from FLV RT.
MF4CH, FF4CH: The "H" at the end represents a histidine Tag at the C-terminus in addition to a N-terminus His-Tag.
FF4G, FF4GC "FF" represents Feline RT mutants not the fusion between MLV and FLV RT.
FF4NDKW, MF(P)4NDKW FLV RT and Fusion RT that have 4 point mutations at D200N, N477D, H592K, L601W.
FF4NGWN, MF(P)4NGWN FLV RT and Fusion RT that have 4 point mutations at D200N, D522G, L601W, D651N.

A listing of exemplary mutant and hybrid sequences is provided below:

```
1. NF5PNAIY
Based on FP(M)-TCH(F), which has finger and palm
domains from MLV RT and thumb, connection and
RNase H domain from FLV RT. Amino acids at the
following positions were mutated: L139P    ,
D200N    , D522A    , F526I    , H632Y    .
Italics indicate sequence from MLV; bolded text
indicates sequence from FLV.
                             (SEQ ID NO: 20)
MGSSHHHHHHSSGLVPRGSHMTLNIEDEYRLHETSKEPDVSLGSTW

LSDFPQAWAETGGMGLAVRQAPHIPLKATSTPVSIKQYPMSQEARL

GIKPHIQRLLDQGILVPCQSPWNTPLLPVKKPGTNDYRPVQDLREV

NKRVEDIHPTVPNPYNLLSG PPSHQWYTVLDLKDAFFCLRLHPTS

QPLFAFEWRDPEMGISGQLTWTRLPQGFKNSPTLF EALHRDLADF

RIQHPDLILLQYVDDLLLAATSELDCQQGTRALLQTLGNLGYRASA

KKAQICQKQVKYLGYLLKEGQRWLTKARKEAILSIPVPKNPRQVRE

FLGTAGYCRLWIPGFAELAAPLYPLTRPGTLFQWGTEQQLAFENIR

KALLSSPALGLPDITKPFELFIDENSGFAKGVLVQKLGPWKRPVAY

LSKKLDTVASGWPPCLRMVAAIAILVKDAGKLTLGQPLTILTSHPV

EALVRQPPNKVVLSNARMTHYQAMLLDAERVHFGPTVSLNPATLLP

LPSGKPPRLSPDLAETMAQTDLTDQPLPDADLTWYT GSS IRNG

ERKAGAAVTTESEVIWAASLPPGTSAQRAELIALTQALKMAKGKKL

TVYTDSRYAFATAHVHGEIYRRRGLLTSEGKEIKNKNEILALLEAL

FLPKRLSII CPGHQKGDSPQAKGNRLADDTAKKAATETQSSLTIL

AAA
```

-continued

2. MF4GC
Based on FP(M)-TCH(F), which has finger and palm domains from MLV RT and thumb, connection and RNase H domain from FLV RT with an extended C-terminal sequence. Amino acids at the following positions were mutated: L139P, D200N, D522G, L601W, E605K. Italics indicate sequence from MLV; bolded text indicates sequence from FLV.

(SEQ ID NO: 21)

MGSSHHHHHHSSGLVPRGSH*MTLNIEDEYRLHETSKEPDVSLGSTW*

*LSDFPQAWAETGGMGLAVRQAPHIPLKATSTPVSIKQYPMSQEARL*

*GIKPHIQRLLDQGILVPCQSPWNTPLLPVKKPGTNDYRPVQDLREV*

*NKRVEDIHPTVPNPYNLLSG PPSHQWYTVLDLKDAFFCLRLHPTS*

*QPLFAFEWRDPEMGISGQLTWTRLPQGFKNSPTLF EALHRDLADF*

*RIQHPDLILLQYVDDLLLAATSELDCQQGTRALLQTLGNLGYRASA*

*KKAQICQKQVKYLGYLLKEGQ*RWLTKARKEAILSIPVPKNPRQVRE

FLGTAGYCRLWIPGFAELAAPLYPLTRPGTLFQWGTEQQLAFENIR

KALLSSPALGLPDITKPFELFIDENSGFAKGVLVQKLGPWKRPVAY

LSKKLDTVASGWPPCLRMVAAIAILVKDAGKLTLGQPLTILTSHPV

EALVRQPPNKVVLSNARMTHYQAMLLDAERVHFGPTVSL PATLLP

LPSGKPPRLSPDLAETMAQTDLTDQPLPDADLTWYT GSSFIRNG

ERKAGAAVTTESEVIWAASLPPGTSAQRAELIALTQALKMAKGKKL

TVYTDSRYAFATAHVHGEIYRRRG LTS GKEIKNKNEILALLEAL

FLPKRLSIIHCPGHQKGDSPQAKGNRLADDTAKKAATETQSSLTIL

PTELIEGPKRPPWEYAAA

3. MF4G
Based on FP(M)-TCH(F), which has finger and palm domains from MLV RT and thumb, connection and RNase H domain from FLV RT without an extended C-terminal sequence. Amino acids at the following positions were mutated: L139P, D200N, D522G, L601W, E605K. Italics indicate sequence from MLV; bolded text indicates sequence from FLV.

(SEQ ID NO: 22)

MGSSHHHHHHSSGLVPRGSH*MTLNIEDEYRLHETSKEPDVSLGSTW*

*LSDFPQAWAETGGMGLAVRQAPHIPLKATSTPVSIKQYPMSQEARL*

*GIKPHIQRLLDQGILVPCQSPWNTPLLPVKKPGTNDYRPVQDLREV*

*NKRVEDIHPTVPNPYNLLSG PPSHQWYTVLDLKDAFFCLRLHPTS*

*QPLFAFEWRDPEMGISGQLTWTRLPQGFKNSPTLF EALHRDLADF*

*RIQHPDLILLQYVDDLLLAATSELDCQQGTRALLQTLGNLGYRASA*

*KKAQICQKQVKYLGYLLKEGQ*RWLTKARKEAILSIPVPKNPRQVRE

FLGTAGYCRLWIPGFAELAAPLYPLTRPGTLFQWGTEQQLAFENIR

KALLSSPALGLPDITKPFELFIDENSGFAKGVLVQKLGPWKRPVAY

LSKKLDTVASGWPPCLRMVAAIAILVKDAGKLTLGQPLTILTSHPV

EALVRQPPNKWLSNARMTHYQAMLLDAERVHFGPTVSLNPATLLP

LPSGKPPRLSPDLAETMAQTDLTDQPLPDADLTWYT GSSFIRNG

ERKAGAAVTTESEVIWAASLPPGTSAQRAELIALTQALKMAKGKKL

TVYTDSRYAFATAHVHGEIYRRRG LTS GKEIKNKNEILALLEAL

FLPKRLSIIHCPGHQKGDSPQAKGNRLADDTAKKAATETQSSLTIL

AAA

4. MF(P)4G
Based on FP(M)$^{PstI}$-TCH(F), which has a shorter finger and palm domains sequence from MLV RT compared to MF4G. The thumb, connection and RNase H domains from FLV RT without an extended C-terminal sequence. Amino acids at the following positions were mutated: L139P, D200N, D522G, L601W, E605K. Italics indicate sequence from MLV; bolded text indicates sequence from FLV.

(SEQ ID NO: 23)

MGSSHHHHHHSSGLVPRGSH*MTLNIEDEYRLHETSKEPDVSLGSTW*

*LSDFPQAWAETGGMGLAVRQAPHIPLKATSTPVSIKQYPMSQEARL*

*GIKPHIQRLLDQGILVPCQSPWNTPLLPVKKPGTNDYRPVQDLREV*

*NKRVEDIHPTVPNPYNLLSG PPSHQWYTVLDLKDAFFCLRLHPTS*

*QPLFAFEWRDPEMGISGQLTWTRLPQGFKNSPTLF EALHRDLADF*

*RIQHPDLILLQYVDDLLLAAATRTECLEGTKALLETLGNKGYRASA*

*KKAQICLQEVTYLGYSLKDGQ*RWLTKARKEAILSIPVPKNPRQVRE

FLGTAGYCRLWIPGFAELAAPLYPLTRPGTLFQWGTEQQLAFENIR

KALLSSPALGLPDITKPFELFIDENSGFAKGVLVQKLGPWKRPVAY

LSKKLDTVASGWPPCLRMVAAIAILVKDAGKLTLGQPLTILTSHPV

EALVRQPPNKWLSNARMTHYQAMLLDAERVHFGPTVSLNPATLLP

LPSGKPPRLSPDLAETMAQTDLTDQPLPDADLTWYT GSSFIRNG

ERKAGAAVTTESEVIWAASLPPGTSAQRAELIALTQALKMAKGKKL

TVYTDSRYAFATAHVHGEIYRRRG LTS GKEIKNKNEILALLEAL

FLPKRLSIIHCPGHQKGDSPQAKGNRLADDTAKKAATETQSSLTIL

AAA

5. MF(P)4NDKW
Based on FP(M)$^{PstI}$-TCH(F), which has a shorter finger and palm domains sequence from MLV RT compared to MF4G. The thumb, connection and RNase H domains from FLV RT without an extended C-terminal sequence. Amino acids at the following positions were mutated: D200N, N479D, H592K, L601W. Italics indicate sequence from MLV; bolded text indicates sequence from FLV.

(SEQ ID NO: 24)

MGSSHHHHHHSSGLVPRGSH*MTLNIEDEYRLHETSKEPDVSLGSTW*

*LSDFPQAWAETGGMGLAVRQAPHIPLKATSTPVSIKQYPMSQEARL*

*GIKPHIQRLLDQGILVPCQSPWNTPLLPVKKPGTNDYRPVQDLREV*

*NKRVEDIHPTVPNPYNLLSGLPPSHQWYTVLDLKDAFFCLRLHPTS*

*QPLFAFEWRDPEMGISGQLTWTRLPQGFKNSPTLF EALHRDLADF*

*RIQHPDLILLQYVDDLLLAAATRTECLEGTKALLETLGNKGYRASA*

*KKAQICLQEVTYLGYSLKDGQ*RWLTKARKEAILSIPVPKNPRQVRE

FLGTAGYCRLWIPGFAELAAPLYPLTRPGTLFQWGTEQQLAFENIR

KALLSSPALGLPDITKPFELFIDENSGFAKGVLVQKLGPWKRPVAY

LSKKLDTVASGWPPCLRMVAAIAILVKDAGKLTLGQPLTILTSHPV

EALVRQPPNKWLSNARMTHYQAMLLDAERVHFGPTVSL PATLLP

LPSGKPPRLSPDLAETMAQTDLTDQPLPDADLTWYTDGSSFIRNG

ERKAGAAVTTESEVIWAASLPPGTSAQRAELIALTQALKMAKGKKL

TVYTDSRYAFATAHV*GEIYRRRG*LTSEGKEIKNKNEILALLEAL

FLPKRLSIIHCPGHQKGDSPQAKGNRLADDTAKKAATETQSSLTIL

AAA

6. MF(P)4NGWN
Based on FP(M)$^{PstI}$-TCH(F), which has a shorter
finger and palm domains sequence from MLV
RT compared to MF4G. The thumb, connection and
RNase H domains from FLV RT without an
extended C-terminal sequence. Amino acids at
the following positions were mutated:
D200N, D522G, L601W, D651N.
Italics indicate sequence from MLV;
bolded text indicates sequence from FLV.
(SEQ ID NO: 25)
MGSSHHHHHHSSGLVPRGSH*MTLNIEDEYRLHETSKEPDVSLGSTW*

*LSDFPQAWAETGGMGLAVRQAPHIPLKATSTPVSIKQYPMSQEARL*

*GIKPHIQRLLDQGILVPCQSPWNTPLLPVKKPGTNDYRPVQDLREV*

*NKRVEDIHPTVPNPYNLLSGLPPSHQWYTVLDLKDAFFCLRLHPTS*

*QPLFAFEWRDPEAIGISGQLTWTRLPQGFKNSPTLF*EALHRDLADF

RIQHPDLILLQYVDDLLLAAATRTECLEGTKALLETLGNKGYRASA

KKAQICLQEVTYLGYSLKDGQRWLTKARKEAILSIPVPKNPRQVRE

FLGTAGYCRLWIPGFAELAAPLYPLTRPGTLFQWGTEQQLAFENIR

KALLSSPALGLPDITKPFELFIDENSGFAKGVLVQKLGPWKRPVAY

LSKKLDTVASGWPPCLRMVAAIAILVKDAGKLTLGQPLTILTSHPV

EALVRQPPNKWLSNARMTHYQAMLLDAERVHFGPTVSLNPATLLP

LPSGKPPRLSPDLAETMAQTDLTDQPLPDADLTWYT*GSSFIRNG*

ERKAGAAVTTESEVIWAASLPPGTSAQRAELIALTQALKMAKGKKL

TVYTDSRYAFATAHVHGEIYRRRG*LTSEGKEIKNKNEILALLEAL*

FLPKRLSIIHCPGHQKGDSPQAKGNRLA*DTAKKAATETQSSLTIL

AAA

7. NF5PNAIYC
Based on FP(M)-TCH(F), which has finger and palm
domains from MLV RT and thumb, connection and
RNase H domain from FLV RT with an extended
C-terminal sequence. Amino acids at the following
positions were mutated: L139P, D200N,
D522A, F526I, H632Y. Italics
indicate sequence from MLV; bolded text indicates
sequence from FLV.
(SEQ ID NO: 39)
MGSSHHHHHHSSGLVPRGSH*MTLNIEDEYRLHETSKEPDVSLGSTW*

*LSDFPQAWAETGGMGLAVRQAPHIPLKATSTPVSIKQYPMSQEARL*

*GIKPHIQRLLDQGILVPCQSPWNTPLLPVKKPGTNDYRPVQDLREV*

*NKRVEDIHPTVPNPYNLLSG*PPSHQWYTVLDLKDAFFCLRLHPTS

*QPLFAFEWRDPEMGISGQLTWTRLPQGFKNSPTLF*EALHRDLADF

*RIQHPDLILLQYVDDLLLAATSELDCQQGTRALLQTLGNLGYRASA*

*KKAQICQKQVKYLGYLLKEGQ*RWLTKARKEAILSIPVPKNPRQVRE

FLGTAGYCRLWIPGFAELAAPLYPLTRPGTLFQWGTEQQLAFENIR

KALLSSPALGLPDITKPFELFIDENSGFAKGVLVQKLGPWKRPVAY

LSKKLDTVASGWPPCLRMVAAIAILVKDAGKLTLGQPLTILTSHPV

EALVRQPPNKWLSNARMTHYQAMLLDAERVHFGPTVSLNPATLLP

LPSGKPPRLSPDLAETMAQTDLTDQPLPDADLTWYT*GSS*IRNG

ERKAGAAVTTESEVIWAASLPPGTSAQRAELIALTQALKMAKGKKL

TVYTDSRYAFATAHVHGEIYRRRGLLTSEGKEIKNKNEILALLEAL

FLPKRLSII*CPGHQKGDSPQAKGNRLADDTAKKAATETQSSLTIL

PTELIEGPKRPPWEYAAA

8. MF4(P)GC
Based on FP(M)$^{PstI}$-TCH(F), which has a shorter
finger and palm domains sequence from MLV
RT compared to MF4G. The thumb, connection
and RNase H domains from FLV RT with an
extended C-terminal sequence. Amino acids
at the following positions were mutated:
L139P, D200N, D522G, L601W,
E605K. Italics indicate sequence from MLV;
bolded text indicates sequence from FLV.
(SEQ ID NO: 40)
MGSSHHHHHHSSGLVPRGSH*MTLNIEDEYRLHETSKEPDVSLGSTW*

*LSDFPQAWAETGGMGLAVRQAPHIPLKATSTPVSIKQYPMSQEARL*

*GIKPHIQRLLDQGILVPCQSPWNTPLLPVKKPGTNDYRPVQDLREV*

*NKRVEDIHPTVPNPYNLLSG*PPSHQWYTVLDLKDAFFCLRLHPTS

*QPLFAFEWRDPEMGISGQLTWTRLPQGFKNSPTLF*EALHRDLADF

*RIQHPDLILLQYVDDLLLAAATRTECLEGTKALLETLGNKGYRASA*

*KKAQICLQEVTYLGYSLKDGQRWLTKARKEAILSIPVPKNPRQVRE*

FLGTAGYCRLWIPGFAELAAPLYPLTRPGTLFQWGTEQQLAFENIR

KALLSSPALGLPDITKPFELFIDENSGFAKGVLVQKLGPWKRPVAY

LSKKLDTVASGWPPCLRMVAAIAILVKDAGKLTLGQPLTILTSHPV

EALVRQPPNKWLSNARMTHYQAMLLDAERVHFGPTVSLNPATLLP

LPSGKPPRLSPDLAETMAQTDLTDQPLPDADLTWYT*GSSFIRNG*

ERKAGAAVTTESEVIWAASLPPGTSAQRAELIALTQALKMAKGKKL

TVYTDSRYAFATAHVHGEIYRRRG*LTS*GKEIKNKNEILALLEAL

FLPKRLSIIHCPGHQKGDSPQAKGNRLADDTAKKAATETQSSLTIL

PTELIEGPKRPPWEYAAA

9. FM1 (1/3 FLV-2/3 MLV RT)
A hybrid RT with 1/3 of the N-terminal sequence
from FLV RT (finger and palm domains) and
the rest of 2/3 of the C-terminal sequence
from MLV RT (Thumb, connection, RNase H
domains). Italics indicate sequence from MLV;
bolded text indicates sequence from FLV.
(SEQ ID NO: 30)
MTLQLEEEYRLFEPESTQKQEMDIWLKNFPQAWAETGGMGMAHCQA

PVLIQLKATATPISIRQYPMPHEAYQGIKPHIRRMLDQGILKPCQS

PWNTPLLPVKKPGTKDYRPVQDLREVNKRVEDIHPTVPNPYNLLST

LPPSHPWYTVLDLKDAFFCLRLHSESQLLFAFEWRDPEIGLSGQLT

WTRLPQGFKNSPTLFDEALHSDLADFRVRYPALVLLQYVDDLLLAA

*ATRTECLEGTKALLETLGNKGYRASAKKAQICLQEVTYLGYSLKDG*

*QRWLTEARKETVMGQPTPKTPRQLREFLGTAGFCRLWIPGFAEMAA*

*PLYPLTKTGTLFNWGPDQQKAYQEIKQALLTAPALGLPDLTKPFEL*

*FVDEKQGYAKGVLTQKLGPWRRPVAYLSKKLDPVAAGWPPCLRMVA*

AIAVLTKDAGKLTMGQPLVILAPHAVEALVKQPPDRWLSNARMTHY

QALLLDTDRVQFGPVVALNPATLLPLPEEGLQHDCLDILAEAHGTR

SDLTDQPLPDADHTWYTDGSSFLQEGQRKAGAAVTTETEVIWARAL

PAGTSAQRAELIALTQALKMAEGKKLNVYTDSRYAFATAHIHGEIY

RRRGLLTSEGKEIKNKDEILALLKALFLPKRLSIIHCPGHQKGNSA

EARGNRMADQAAREVATRETPGTSTLL

10. FM2 (2/3 FLV-1/3 MLV RT)
A hybrid RT with 2/3 of the N-terminal sequence
from FLV RT (finger, palm, thumb, connection
domains) and the rest of 1/3 of the C-terminal
sequence from MLV RT (RNase H domain only).
Italics indicate sequence from MLV; bolded text
indicates sequence from FLV.
(SEQ ID NO: 31)
MTLQLEEEYRLFEPESTQKQEMDIWLKNFPQAWAETGGMGMAHCQA

PVLIQLKATATPISIRQYPMPHEAYQGIKPHIRRMLDQGILKPCQS

PWNTPLLPVKKPGTKDYRPVQDLREVNKRVEDIHPTVPNPYNLLST

LPPSHPWYTVLDLKDAFFCLRLHSESQLLFAFEWRDPEIGLSGQLT

WTRLPQGFKNSPTLFDEALHSDLADFRVRYPALVLLQYVDDLLLAA

ATRTECLEGTKALLETLGNKGYRASAKKAQICLQEVTYLGYSLKDG

QRWLTKARKEAILSIPVPKNPRQVREFLGTAGYCRLWIPGFAELAA

PLYPLTRPGTLFQWGTEQQLAFENIRKALLSSPALGLPDITKPFEL

FIDENSGFAKGVLVQKLGPWKRPVAYLSKKLDTVASGWPPCLRMVA

AIAILVKDAGKLTLGQPLTILTSHPVEALVRQPPNKWLSNARMTHY

QAMLLDAERVHFGPTVSLNPATLLPLPSGKPPRLSPD*ILAEAHGTR*

*SDLTDQPLPDADHTWYTDGSSFLQEGQRKAGAAVTTETEVIWARAL*

*PAGTSAQRAELIALTQALKMAEGKKLNVYTDSRYAFATAHIHGEIY*

*RRRGLLTSEGKEIKNKDEILALLKALFLPKRLSIIHCPGHQKGNSA*

*EARGNRMADQAAREVATRETPGTSTLL*

11. Wild type MLV RT sequence
(SEQ ID NO: 32)
*TLNIEDEHRLHETSKEPDVSLGSTWLSDFPQAWAETGGMGLAVRQA*

*PLIIPLKATSTPVSIKQYPMSQEARLGIKPHIQRLLDQGILVPCQS*

*PWNTPLLPVKKPGTNDYRPVQDLREVNKRVEDIHPTVPNPYNLLSG*

*LPPSHQWYTVLDLKDAFFCLRLHPTSQPLFAFEWRDPEMGISGQLT*

*WTRLPQGFKNSPTLFDEALHRDLADFRIQHPDLILLQYYDDLLLAA*

*TSELDCQQGTRALLQTLGNLGYRASAKKAQICQKQVKYLGYLLKEG*

*QRWLTEARKETVMGQPTPKTPRQLREFLGTAGFCRLWIPGFAEMAA*

*PLYPLTKTGTLFNWGPDQQKAYQEIKQALLTAPALGLPDLTKPFEL*

*FVDEKQGYAKGVLTQKLGPWRRPVAYLSKKLDPVAAGWPPCLRMVA*

*AIAVLTKDAGKLTMGQPLVILAPHAVEALVKQPPDRWLSNARMTHY*

*QALLLDTDRVQFGPVVALNPATLLPLPEEGLQHNCLDILAEAHGTR*

*PDLTDQPLPDADHTWYTDGSSLLQEGQRKAGAAVTTETEVIWAKAL*

*PAGTSAQRAELIALTQALKMAEGKKLNVYTDSRYAFATAHIHGEIY*

*RRRGLLTSEGKEIKNKDEILALLKALFLPKRLSIIHCPGHQKGHSA*

*EARGNRMADQAARKAAITETPDTSTLL*

12. Wild type FLV RT sequence
(SEQ ID NO: 33)
TLQLEEEYRLFEPESTQKQEMDIWLKNFPQAWAETGGMGMAHCQAP

VLIQLKATATPISIRQYPMPHEAYQGIKPHIRRMLDQGILKPCQSP

WNTPLLPVKKPGTKDYRPVQDLREVNKRVEDIHPTVPNPYNLLSTL

PPSHPWYTVLDLKDAFFCLRLHSESQLLFAFEWRDPEIGLSGQLTW

TRLPQGFKNSPTLFDEALHSDLADFRVRYPALVLLQYVDDLLLAAA

TRTECLEGTKALLETLGNKGYRASAKKAQICLQEVTYLGYSLKDGQ

RWLTKARKEAILSIPVPKNPRQVREFLGTAGYCRLWIPGFAELAAP

LYPLTRPGTLFQWGTEQQLAFENIRKALLSSPALGLPDITKPFELF

IDENSGFAKGVLVQKLGPWKRPVAYLSKKLDTVASGWPPCLRMVAA

IAILVKDAGKLTLGQPLTILTSHPVEALVRQPPNKWLSNARMTHYQ

AMLLDAERVHFGPTVSLNPATLLPLPSGKPPRLSPDLAETMAQTDL

TDQPLPDADLTWYTDGSSFIRNGERKAGAAVTTESEVIWAASLPPG

TSAQRAELIALTQALKMAKGKKLTVYTDSRYAFATAHVHGEIYRRR

GLLTSEGKEIKNKNEILALLEALFLPKRLSIIHCPGHQKGDSPQAK

GNRLADDTAKKAATETQSSLTIL

Summary of Sequences:
SEQ ID NO:1: generic Short MLV
SEQ ID NO:2: generic Longer MLV
SEQ ID NO:3: specific Short MLV
SEQ ID NO:4: specific Longer MLV
SEQ ID NO:5: generic Shorter w/o c-term extension FLV
SEQ ID NO:6: with longer c-term extension FLV: generic
SEQ ID NO:7: Shorter w/o c-term extension FLV: specific mutations at 522, 526, 632
SEQ ID NO:8: with longer c-term extension FLV: specific mutations at 522, 601, 605
SEQ ID NO:9: Shorter w/o c-term extension FLV: specific mutations at 522, 601, 605
SEQ ID NO:10: long N-term w/o c-term extension FLV: generic
SEQ ID NO:11: long N-term w/o c-term extension FLV: specific mutations at 522, 601, 605
SEQ ID NO:12: long N-term w/o c-term extension FLV: specific mutations at 479, 592, 601
SEQ ID NO:13: long N-term w/o c-term extension FLV: specific mutations at 522, 601, 651
SEQ ID NO:14: NF5PNAIY without leader or end sequences
SEQ ID NO:15: MF4GC without leader or end sequences
SEQ ID NO:16: MF4G without leader or end sequences
SEQ ID NO:17: MF4(P)G without leader or end sequences
SEQ ID NO:18: MF(P)4NDKW without leader or end sequences
SEQ ID NO:19: MF(P)4NGWN without leader or end sequences
SEQ ID NO:20: NF5PNAIY with leader and end sequences
SEQ ID NO:21: MF4GC with leader and end sequences
SEQ ID NO:22: MF4G with leader and end sequences
SEQ ID NO:23: MF(P)4G with leader and end sequences
SEQ ID NO:24: MF(P)4NDKW with leader and end sequences
SEQ ID NO:25: MF(P)4NGWN with leader and end sequences
SEQ ID NO:26: 1/3 FLV N-terminus
SEQ ID NO: 27 2/3 FLV N-terminus SEQ ID NO:28 ⅔ MLV C-terminus
SEQ ID NO:29 ⅓ MLV C-terminus
SEQ ID NO:30 FM1 (⅓ FLV-⅔ MLV RT)
SEQ ID NO:31 FM2 (⅔ FLV-⅓ MLV RT)
SEQ ID NO: 32 Wild type MLV RT sequence
SEQ ID NO: 33 Wild type FLV RT sequence
SEQ ID NO:34: NF5PNAIYC without leader or end sequences
SEQ ID NO:35: MF4(P)GC without leader or end sequences
SEQ ID NO:36: NF5PNAIYC MLVRT portion
SEQ ID NO:37: NF5PNAIYC FLVRT portion
SEQ ID NO:38: MF4(P)GC MLVRT portion
SEQ ID NO:39: MF4(P)GC FLVRT portion
SEQ ID NO:40: NF5PNAIYC with leader and end sequences
SEQ ID NO:41: MF4(P)GC with leader and end sequences The examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

| SEQUENCES |
|---|
| SEQ ID NO: 1: generic Short MLV:<br>MTLNIEDEYRLHETSKEPDVSLGSTWLSDFPQAWAETGGMGLAVR<br>QAPLIIPLKATSTPVSIKQYPMSQEARLGIKPHIQRLLDQGILVP<br>CQSPWNTPLLPVKKPGTNDYRPVQDLREVNKRVEDIHPTVPNPYN<br>LLSG(L/I)PPSHQWYTVLDLKDAFFCLRLEIPTSQPLFAFEWRD<br>PEMGISGQLTWTRLPQGFKNSPTLF(Q/R)EALEIRDLADFRIQH<br>PDLILLQ |
| SEQ ID NO: 2: generic Longer MLV:<br>MTLNIEDEYRLHETSKEPDVSLGSTWLSDFPQAWAETGGMGLAVR<br>QAPLIIPLKATSTPVSIKQYPMSQEARLGIKPHIQRLLDQGILVP<br>CQSPWNTPLLPVKKPGTNDYRPVQDLREVNKRVEDIHPTVPNPYN<br>LLSG(L/I)PPSHQWYTVLDLKDAFFCLRLEIPTSQPLFAFEWRD<br>PEMGISGQLTWTRLPQGFKNSPTLF(Q/R)EALEIRDLADFRIQH<br>PDLILLQYVDDLLLAATSELDCQQGTRALLQTLGNLGYRASAKKA<br>QICQKQVKYLGYLLKEGQ |
| SEQ ID NO: 3: specific Short MLV:<br>MTLNIEDEYRLHETSKEPDVSLGSTWLSDFPQAWAETGGMGLAVR<br>QAPLIIPLKATSTPVSIKQYPMSQEARLGIKPHIQRLLDQGILVP<br>CQSPWNTPLLPVKKPGTNDYRPVQDLREVNKRVEDIHPTVPNPYN<br>LLSGIPPSHQWYTVLDLKDAFFCLRLEIPTSQPLFAFEWRDPEMG<br>ISGQLTWTRLPQGFKNSPTLFNEALHRDLADFRIQIIPDLILLQ |
| SEQ ID NO: 4: specific Longer MLV:<br>MTLNIEDEYRLHETSKEPDVSLGSTWLSDFPQAWAETGGMGLAVR<br>QAPLIIPLKATSTPVSIKQYPMSQEARLGIKPHIQRLLDQGILVP<br>CQSPWNTPLLPVKKPGTNDYRPVQDLREVNKRVEDIHPTVPNPYN<br>LLSGIPPSHQWYTVLDLKDAFFCLRLEIPTSQPLFAFEWRDPEMG |

| SEQUENCES |
|---|
| ISGQLTWTRLPQGFKNSPTLFNEALEIRDLADFRIQHPDLILLQY<br>VDDLLLAATSELDCQQGTRALLQTLGNLGYRASAKKAQICQKQVK<br>YLGYLLKEGQ |
| SEQ ID NO: 5: generic Shorter w/o c-term extension FLV:<br>RWLTKARKEAILSIPVPKNPRQVREFLGTAGYCRLWIPGFAELAA<br>PLYPLTRPGTLFQWGTEQQLAFENIRKALLSSPALGLPDITKPFE<br>LFIDENSGFAKGVLVQKLGPWKRPVAYLSKKLDTVASGWPPCLRM<br>VAAIAILVKDAGKLTLGQPLTILTSHPVEALVRQPPNKWLSNARM<br>THYQAMLLDAERVHFGPTVSLNPATLLPLPSGKPPRLSPDLAETM<br>AQTDLTDQPLPDADLTWYT(D/G/R/A)GSS(E/I)IRNGERKAG<br>AAVTTESEVIWAASLPPGTSAQRAELIALTQALKMAKGKKLTVYT<br>DSRYAFATAHV(E/K)GEIYRRRG(L/W)LTS(E/T)GKEIKNKN<br>EILALLEALFLPKRLSII(H/Y)CPGHQKGDSPQAKGNRLADDTA<br>KKAATETQSSLTIL |
| SEQ ID NO: 6: with longer c-term extension FLV: generic<br>RWLTKARKEAILSIPVPKNPRQVREFLGTAGYCRLWIPGFAELAA<br>PLYPLTRPGTLFQWGTEQQLAFENIRKALLSSPALGLPDITKPFE<br>LFIDENSGFAKGVLVQKLGPWKRPVAYLSKKLDTVASGWPPCLRM<br>VAAIAILVKDAGKLTLGQPLTILTSHPVEALVRQPPNKWLSNARM<br>THYQAMLLDAERVHFGPTVSLNPATLLPLPSGKPPRLSPDLAETM<br>AQTDLTDQPLPDADLTWYT(D/G/N/A)GSS(E/I)IRNGERKAG<br>AAVTIESEVIWAASLPPGTSAQRAELIALTQALKMAKGKKLTVYT<br>DSRYAFATAHV(E/K)GEIYRRRG(L/W)LTS(E/K)GKEIKNKN<br>EILALLEALFLPKRLSII(H/Y)CPGHQKGDSPQAKGNRLADDTA<br>KKAATETQSSLTILPTELIEGPKRPPWEY |
| SEQ ID NO: 7: Shorter w/o c-term extension FLV: specific 522, 526, 632<br>RWLTKARKEAILSIPVPKNPRQVREFLGTAGYCRLWIPGFAELAA<br>PLYPLTRPGTLFQWGTEQQLAFENIRKALLSSPALGLPDITKPFE<br>LFIDENSGFAKGVLVQKLGPWKRPVAYLSKKLDTVASGWPPCLRM<br>VAAIAILVKDAGKLTLGQPLTILTSHPVEALVRQPPNKWLSNARM<br>THYQAMLLDAERVHFGPTVSLNPATLLPLPSGKPPRLSPDLAETM<br>AQTDLTDQPLPDADLTWYTAGSSIIRNGERKAGAAVTTESEVIWA<br>ASLPPGTSAQRAELIALTQALKMAKGKKLTVYTDSRYAFATAHVH<br>GEIYRRRGLLTSEGKEIKNKNEILALLEALFLPKRLSIIYCPGHQ<br>KGDSPQAKGNRLADDTAKKAATETQSSLTIL |
| SEQ ID NO: 8: with longer c-term extension FLV: 522, 601, 605<br>RWLTKARKEAILSIPVPKNPRQVREFLGTAGYCRLWIPGFAELAA<br>PLYPLTRPGTLFQWGTEQQLAFENIRKALLSSPALGLPDITKPFE<br>LFIDENSGFAKGVLVQKLGPWKRPVAYLSKKLDTVASGWPPCLRM |

VAAIAILVKDAGKLTLGQPLTILTSHPVEALVRQPPNKWLSNARM

THYQAMLLDAERVHFGPTVSLNPATLLPLPSGKPPRLSPDLAETM

AQTDLTDQPLPDADLTWYTGSSFIRNGERKAGAAVTTESEVIWA

ASLPPGTSAQRAELIALTQALKMAKGKKLTVYTDSRYAFATAHVH

GEIYRRRGLTSGKEIKNKNEILALLEALFLPKRLSIIHCPGHQ

KGDSPQAKGNRLADDTAKKAATETQSSLTILPTELIEGPKRPPWE

Y

SEQ ID NO: 9: Shorter w/o c-term extension
FLV: specific 522, 601, 605
RWLTKARKEAILSIPVPKNPRQVREFLGTAGYCRLWIPGFAELAA

PLYPLTRPGTLFQWGTEQQLAFENIRKALLSSPALGLPDITKPFE

LFIDENSGFAKGVLVQKLGPWKRPVAYLSKKLDTVASGWPPCLRM

VAAIAILVKDAGKLTLGQPLTILTSHPVEALVRQPPNKWLSNARM

THYQAMLLDAERVHFGPTVSLNPATLLPLPSGKPPRLSPDLAETM

AQTDLTDQPLPDADLTWYTGSSFIRNGERKAGAAVTTESEVIWA

ASLPPGTSAQRAELIALTQALKMAKGKKLTVYTDSRYAFATAHVH

GEIYRRRGLTSGKEIKNKNEILALLEALFLPKRLSIIHCPGHQ

KGDSPQAKGNRLADDTAKKAATETQSSLTIL

SEQ ID NO: 10: long N-term w/o c-term
extension FLV: generic
YVDDLLLAAATRTECLEGTKALLETLGNKGYRASAKKAQICLQEV

TYLGYSLKDGQRWLTKARKEAILSIPVPKNPRQVREFLGTAGYCR

LWIPGFAELAAPLYPLTRPGTLFQWGTEQQLAFENIRKALLSSPA

LGLPDITKPFELFIDENSGFAKGVLVQKLGPWKRPVAYLSKKLDT

VASGWPPCLRMVAAIAILVKDAGKLTLGQPLTILTSHPVEALVRQ

PPNKWLSNARMTHYQAMLLDAERVHFGPTVSLNPATLLPLPSGKP

PRLSPDLAETMAQTDLTDQPLPDADLTWYT(D/G/N/A)GSS (P/T)IRNGERKAGAAVTTESEVIWAASLPPGTSAQRAELIALTQ

ALKMAKGKKLTVYTDSRYAFATAHV(R/E)GEIYRRRG(L/W)LT

S(E/K)GKEIKNKNEILALLEALFLPKRLSII(D/V)CPGHQKGD

SPQAKGNRLADDTAKKAATETQSSLTIL

SEQ ID NO: 11: long N-term w/o c-term
extension FLV: specific 522, 601, 605
YVDDLLLAAATRTECLEGTKALLETLGNKGYRASAKKAQICLQEV

TYLGYSLKDGQRWLTKARKEAILSIPVPKNPRQVREFLGTAGYCR

LWIPGFAELAAPLYPLTRPGTLFQWGTEQQLAFENIRKALLSSPA

LGLPDITKPFELFIDENSGFAKGVLVQKLGPWKRPVAYLSKKLDT

VASGWPPCLRMVAAIAILVKDAGKLTLGQPLTILTSHPVEALVRQ

PPNKWLSNARMTHYQAMLLDAERVHFGPTVSLNPATLLPLPSGKP

PRLSPDLAETMAQTDLTDQPLPDADLTWYTGSSFIRNGERKAGA

AVTTESEVIWAASLPPGTSAQRAELIALTQALKMAKGKKLTVYTD

SRYAFATAHVHGEIYRRRGLTSGKEIKNKNEILALLEALFLPK

RLSIIHCPGHQKGDSPQAKGNRLADDTAKKAATETQSSLTIL

SEQ ID NO: 12: long N-term w/o c-term
extension FLV: specific 479, 592, 601
YVDDLLLAAATRTECLEGTKALLETLGNKGYRASAKKAQICLQEV

TYLGYSLKDGQRWLTKARKEAILSIPVPKNPRQVREFLGTAGYCR

LWIPGFAELAAPLYPLTRPGTLFQWGTEQQLAFENIRKALLSSPA

LGLPDITKPFELFIDENSGFAKGVLVQKLGPWKRPVAYLSKKLDT

VASGWPPCLRMVAAIAILVKDAGKLTLGQPLTILTSHPVEALVRQ

PPNKWLSNARMTHYQAMLLDAERVHFGPTVSLPATLLPLPSGKP

PRLSPDLAETMAQTDLTDQPLPDADLTWYTDGSSFIRNGERKAGA

AVTTESEVIWAASLPPGTSAQRAELIALTQALKMAKGKKLTVYTD

SRYAFATAHVGEIYRRRGLTSEGKEIKNKNEILALLEALFLPK

RLSIIHCPGHQKGDSPQAKGNRLADDTAKKAATETQSSLTIL

SEQ ID NO: 13: long N-term w/o c-term
extension FLV: specific 522, 601, 651
YVDDLLLAAATRTECLEGTKALLETLGNKGYRASAKKAQICLQEV

TYLGYSLKDGQRWLTKARKEAILSIPVPKNPRQVREFLGTAGYCR

LWIPGFAELAAPLYPLTRPGTLFQWGTEQQLAFENIRKALLSSPA

LGLPDITKPFELFIDENSGFAKGVLVQKLGPWKRPVAYLSKKLDT

VASGWPPCLRMVAAIAILVKDAGKLTLGQPLTILTSHPVEALVRQ

PPNKWLSNARMTHYQAMLLDAERVHFGPTVSLNPATLLPLPSGKP

PRLSPDLAETMAQTDLTDQPLPDADLTWYTGSSFIRNGERKAGA

AVTTESEVIWAASLPPGTSAQRAELIALTQALKMAKGKKLTVYTD

SRYAFATAHVHGEIYRRRGLTSEGKEIKNKNEILALLEALFLPK

RLSIIHCPGHQKGDSPQAKGNRLADTAKKAATETQSSLTIL

SEQ ID NO: 14: NF5PNAIY without leader or end
sequences:
MTLNIEDEYRLHETSKEPDVSLGSTWLSDFPQAWAETGGMGLAVR

QAPLIIPLKATSTPVSIKQYPMSQEARLGIKPHIQRLLDQGILVP

CQSPWNTPLLPVKKPGTNDYRPVQDLREVNKRVEDIHPTVPNPYN

LLSGPPSHQWYTVLDLKDAFFCLRLHPTSQPLFAFEWRDPEMGI

SGQLTWTRLPQGFKNSPTLFEALHRDLADFRIQHPDLILLQYVD

DLLLAATSELDCQQGTRALLQTLGNLGYRASAKKAQICQKQVKYL

GYLLKEGQRWLTKARKEAILSIPVPKNPRQVREFLGTAGYCRLWI

PGFAELAAPLYPLTRPGTLFQWGTEQQLAFENIRKALLSSPALGL

PDITKPFELFIDENSGFAKGVLVQKLGPWKRPVAYLSKKLDTVAS

GWPPCLRMVAAIAILVKDAGKLTLGQPLTILTSHPVEALVRQPPN

KWLSNARMTHYQAMLLDAERVHFGPTVSLNPATLLPLPSGKPPRL

SPDLAETMAQTDLTDQPLPDADLTWYTGSSIRNGERKAGAAVT

TESEVIWAASLPPGTSAQRAELIALTQALKMAKGKKLTVYTDSRY

AFATAHVHGEIYRRRGLLTSEGKEIKNKNEILALLEALFLPKRLS

IIHCPGHQKGDSPQAKGNRLADDTAKKAATETQSSLTIL

SEQ ID NO: 15: MF4GC without leader or end
sequences:
MTLNIEDEYRLHETSKEPDVSLGSTWLSDFPQAWAETGGMGLAVR

QAPLIIPLKATSTPVSIKQYPMSQEARLGIKPHIQRLLDQGILVP

CQSPWNTPLLPVKKPGTNDYRPVQDLREVNKRVEDIHPTVPNPYN

LLSGPPSHQWYTVLDLKDAFFCLRLHPTSQPLFAFEWRDPEMGI

SGQLTWTRLPQGFKNSPTLFEALHRDLADFRIQHPDLILLQYVD

DLLLAATSELDCQQGTRALLQTLGNLGYRASAKKAQICQKQVKYL

GYLLKEGQRWLTKARKEAILSIPVPKNPRQVREFLGTAGYCRLWI

PGFAELAAPLYPLTRPGTLFQWGTEQQLAFENIRKALLSSPALGL

PDITKPFELFIDENSGFAKGVLVQKLGPWKRPVAYLSKKLDTVAS

GWPPCLRMVAAIAILVKDAGKLTLGQPLTILTSHPVEALVRQPPN

KWLSNARMTHYQAMLLDAERVHFGPTVSLNPATLLPLPSGKPPRL

SPDLAETMAQTDLTDQPLPDADLTWYTGSSFIRNGERKAGAAVT

TESEVIWAASLPPGTSAQRAELIALTQALKMAKGKKLTVYTDSRY

AFATAHVHGEIYRRRGLTSGKEIKNKNEILALLEALFLPKRLS

IIHCPGHQKGDSPQAKGNRLADDTAKKAATETQSSLTILPTELIE

GPKRPPWEY

SEQ ID NO: 16: MF4G without leader or end
sequences:
MTLNIEDEYRLHETSKEPDVSLGSTWLSDFPQAWAETGGMGLAVR

QAPLIIPLKATSTPVSIKQYPMSQEARLGIKPHIQRLLDQGILVP

CQSPWNTPLLPVKKPGTNDYRPVQDLREVNKRVEDIHPTVPNPYN

LLSGPPSHQWYTVLDLKDAFFCLRLHPTSQPLFAFEWRDPEMGI

SGQLTWTRLPQGFKNSPTLFEALHRDLADFRIQHPDLILLQYVD

DLLLAATSELDCQQGTRALLQTLGNLGYRASAKKAQICQKQVKYL

GYLLKEGQRWLTKARKEAILSIPVPKNPRQVREFLGTAGYCRLWI

PGFAELAAPLYPLTRPGTLFQWGTEQQLAFENIRKALLSSPALGL

PDITKPFELFIDENSGFAKGVLVQKLGPWKRPVAYLSKKLDTVAS

GWPPCLRMVAAIAILVKDAGKLTLGQPLTILTSHPVEALVRQPPN

KWLSNARMTHYQAMLLDAERVHFGPTVSLNPATLLPLPSGKPPRL

SPDLAETMAQTDLTDQPLPDADLTWYTGSSFIRNGERKAGAAVT

TESEVIWAASLPPGTSAQRAELIALTQALKMAKGKKLTVYTDSRY

AFATAHVHGEIYRRRGLTSGKEIKNKNEILALLEALFLPKRLS

IIHCPGHQKGDSPQAKGNRLADDTAKKAATETQSSLTIL

SEQ ID NO: 17: MF4(P)G without leader or end
sequences:
MTLNIEDEYRLHETSKEPDVSLGSTWLSDFPQAWAETGGMGLAVR

QAPLIIPLKATSTPVSIKQYPMSQEARLGIKPHIQRLLDQGILVP

CQSPWNTPLLPVKKPGTNDYRPVQDLREVNKRVEDIHPTVPNPYN

LLSGPPSHQWYTVLDLKDAFFCLRLHPTSQPLFAFEWRDPEMGI

SGQLTWTRLPQGFKNSPTLFEALHRDLADFRIQHPDLILLQYVD

DLLLAAATRTECLEGTKALLETLGNKGYRASAKKAQICLQEVTYL

GYSLKDGQRWLTKARKEAILSIPVPKNPRQVREFLGTAGYCRLWI

PGFAELAAPLYPLTRPGTLFQWGTEQQLAFENIRKALLSSPALGL

PDITKPFELFIDENSGFAKGVLVQKLGPWKRPVAYLSKKLDTVAS

GWPPCLRMVAAIAILVKDAGKLTLGQPLTILTSHPVEALVRQPPN

KWLSNARMTHYQAMLLDAERVHFGPTVSLNPATLLPLPSGKPPRL

SPDLAETMAQTDLTDQPLPDADLTWYTGSSFIRNGERKAGAAVT

TESEVIWAASLPPGTSAQRAELIALTQALKMAKGKKLTVYTDSRY

AFATAHVHGEIYRRRGLTSGKEIKNKNEILALLEALFLPKRLS

IIHCPGHQKGDSPQAKGNRLADDTAKKAATETQSSLTIL

SEQ ID NO: 18: MF(P)4NDKW without leader or
end sequences:
MTLNIEDEYRLHETSKEPDVSLGSTWLSDFPQAWAETGGMGLAVR

QAPLIIPLKATSTPVSIKQYPMSQEARLGIKPHIQRLLDQGILVP

CQSPWNTPLLPVKKPGTNDYRPVQDLREVNKRVEDIHPTVPNPYN

LLSGLPPSHQWYTVLDLKDAFFCLRLHPTSQPLFAFEWRDPEMGI

SGQLTWTRLPQGFKNSPTLFEALHRDLADFRIQHPDLILLQYVD

DLLLAAATRTECLEGTKALLETLGNKGYRASAKKAQICLQEVTYL

GYSLKDGQRWLTKARKEAILSIPVPKNPRQVREFLGTAGYCRLWI

PGFAELAAPLYPLTRPGTLFQWGTEQQLAFENIRKALLSSPALGL

PDITKPFELFIDENSGFAKGVLVQKLGPWKRPVAYLSKKLDTVAS

GWPPCLRMVAAIAILVKDAGKLTLGQPLTILTSHPVEALVRQPPN

KWLSNARMTHYQAMLLDAERVHFGPTVSLNPATLLPLPSGKPPRL

SPDLAETMAQTDLTDQPLPDADLTWYTDGSSFIRNGERKAGAAVT

TESEVIWAASLPPGTSAQRAELIALTQALKMAKGKKLTVYTDSRY

AFATAHVGEIYRRRGLTSEGKEIKNKNEILALLEALFLPKRLS

IIHCPGHQKGDSPQAKGNRLADDTAKKAATETQSSLTIL

SEQ ID NO: 19: MF(P)4NGWN without leader or
end sequences:
YVDDLLLAAATRTECLEGTKALLETLGNKGYRASAKKAQICLQEV

TYLGYSLKDGQRWLTKARKEAILSIPVPKNPRQVREFLGTAGYCR

LWIPGFAELAAPLYPLTRPGTLFQWGTEQQLAFENIRKALLSSPA

LGLPDITKPFELFIDENSGFAKGVLVQKLGPWKRPVAYLSKKLDT

VASGWPPCLRMVAAIAILVKDAGKLTLGQPLTILTSHPVEALVRQ

PPNKWLSNARMTHYQAMLLDAERVHFGPTVSLNPATLLPLPSGKP

PRLSPDLAETMAQTDLTDQPLPDADLTWYTGSSFIRNGERKAGA

AVTTESEVIWAASLPPGTSAQRAELIALTQALKMAKGKKLTVYTD

SRYAFATAHVHGEIYRRRGLTSEGKEIKNKNEILALLEALFLPK

RLSIIHCPGHQKGDSPQAKGNRLADDTAKKAATETQSSLTIL

| SEQUENCES |
|---|
| SEQ ID NO: 20: NF5PNAIY with leader and end sequences:<br>MGSSHHHHHHSSGLVPRGSHMTLNIEDEYRLHETSKEPDVSLGST<br>WLSDFPQAWAETGGMGLAVRQAPLIIPLKATSTPVSIKQYPMSQE<br>ARLGIKPHIQRLLDQGILVPCQSPWNTPLLPVKKPGTNDYRPVQD<br>LREVNKRVEDIHPTVPNPYNLLSGPPSHQWYTVLDLKDAFFCLR<br>LHPTSQPLFAFEWRDPEMGISGQLTWTRLPQGFKNSPTLFEALH<br>RDLADFRIQHPDLILLQYVDDLLLAATSELDCQQGTRALLQTLGN<br>LGYRASAKKAQICQKQVKYLGYLLKEGQRWLTKARKEAILSIPVP<br>KNPRQVREFLGTAGYCRLWIPGFAELAAPLYPLTRPGTLFQWGTE<br>QQLAFENIRKALLSSPALGLPDITKPFELFIDENSGFAKGVLVQK<br>LGPWKRPVAYLSKKLDTVASGWPPCLRMVAAIAILVKDAGKLTLG<br>QPLTILTSHPVEALVRQPPNKWLSNARMTHYQAMLLDAERVHFGP<br>TVSLNPATLLPLPSGKPPRLSPDLAETMAQTDLTDQPLPDADLTW<br>YTGSSIRNGERKAGAAVTTESEVIWAASLPPGTSAQRAELIAL<br>TQALKMAKGKKLTVYTDSRYAFATAHVHGEIYRRRGLLTSEGKEI<br>KNKNEILALLEALFLPKRLSIICPGHQKGDSPQAKGNRLADDTA<br>KKAATETQSSLTILAAA |
| SEQ ID NO: 21: MF4GC with leader and end sequences:<br>MGSSHHHHHHSSGLVPRGSHMTLNIEDEYRLHETSKEPDVSLGST<br>WLSDFPQAWAETGGMGLAVRQAPLIIPLKATSTPVSIKQYPMSQE<br>ARLGIKPHIQRLLDQGILVPCQSPWNTPLLPVKKPGTNDYRPVQD<br>LREVNKRVEDIHPTVPNPYNLLSGPPSHQWYTVLDLKDAFFCLR<br>LHPTSQPLFAFEWRDPEMGISGQLTWTRLPQGFKNSPTLFEALH<br>RDLADFRIQHPDLILLQYVDDLLLAATSELDCQQGTRALLQTLGN<br>LGYRASAKKAQICQKQVKYLGYLLKEGQRWLTKARKEAILSIPVP<br>KNPRQVREFLGTAGYCRLWIPGFAELAAPLYPLTRPGTLFQWGTE<br>QQLAFENIRKALLSSPALGLPDITKPFELFIDENSGFAKGVLVQK<br>LGPWKRPVAYLSKKLDTVASGWPPCLRMVAAIAILVKDAGKLTLG<br>QPLTILTSHPVEALVRQPPNKWLSNARMTHYQAMLLDAERVHFGP<br>TVSLNPATLLPLPSGKPPRLSPDLAETMAQTDLTDQPLPDADLTW<br>YTGSSFIRNGERKAGAAVTTESEVIWAASLPPGTSAQRAELIAL<br>TQALKMAKGKKLTVYTDSRYAFATAHVHGEIYRRRGLTSGKEI<br>KNKNEILALLEALFLPKRLSIIHCPGHQKGDSPQAKGNRLADDTA<br>KKAATETQSSLTILPTELIEGPKRPPWEYAAA |
| SEQ ID NO: 22: MF4G with leader and end sequences:<br>MGSSHHHHHHSSGLVPRGSHMTLNIEDEYRLHETSKEPDVSLGST<br>WLSDFPQAWAETGGMGLAVRQAPLIIPLKATSTPVSIKQYPMSQE<br>ARLGIKPHIQRLLDQGILVPCQSPWNTPLLPVKKPGTNDYRPVQD<br>LREVNKRVEDIHPTVPNPYNLLSGPPSHQWYTVLDLKDAFFCLR |

| SEQUENCES |
|---|
| LHPTSQPLFAFEWRDPEMGISGQLTWTRLPQGFKNSPTLFEALH<br>RDLADFRIQHPDLILLQYVDDLLLAATSELDCQQGTRALLQTLGN<br>LGYRASAKKAQICQKQVKYLGYLLKEGQRWLTKARKEAILSIPVP<br>KNPRQVREFLGTAGYCRLWIPGFAELAAPLYPLTRPGTLFQWGTE<br>QQLAFENIRKALLSSPALGLPDITKPFELFIDENSGFAKGVLVQK<br>LGPWKRPVAYLSKKLDTVASGWPPCLRMVAAIAILVKDAGKLTLG<br>QPLTILTSHPVEALVRQPPNKWLSNARMTHYQAMLLDAERVHFGP<br>TVSLNPATLLPLPSGKPPRLSPDLAETMAQTDLTDQPLPDADLTW<br>YTGSSFIRNGERKAGAAVTTESEVIWAASLPPGTSAQRAELIAL<br>TQALKMAKGKKLTVYTDSRYAFATAHVHGEIYRRRGLTSGKEI<br>KNKNEILALLEALFLPKRLSIIHCPGHQKGDSPQAKGNRLADDTA<br>KKAAIETQSSLTILAAA |
| SEQ ID NO: 23: MF(P)4G with leader and end sequences:<br>MGSSHHHHHHSSGLVPRGSHMTLNIEDEYRLHETSKEPDVSLGST<br>WLSDFPQAWAETGGMGLAVRQAPLIIPLKATSTPVSIKQYPMSQE<br>ARLGIKPHIQRLLDQGILVPCQSPWNTPLLPVKKPGTNDYRPVQD<br>LREVNKRVEDIHPTVPNPYNLLSGPPSHQWYTVLDLKDAFFCLR<br>LHPTSQPLFAFEWRDPEMGISGQLTWTRLPQGFKNSPTLFEALH<br>RDLADFRIQHPDLILLQYVDDLLLAAATRTECLEGTKALLETLGN<br>KGYRASAKKAQICLQEVTYLGYSLKDGQRWLTKARKEAILSIPVP<br>KNPRQVREFLGTAGYCRLWIPGFAELAAPLYPLTRPGTLFQWGTE<br>QQLAFENIRKALLSSPALGLPDITKPFELFIDENSGFAKGVLVQK<br>LGPWKRPVAYLSKKLDTVASGWPPCLRMVAAIAILVKDAGKLTLG<br>QPLTILTSHPVEALVRQPPNKWLSNARMTHYQAMLLDAERVHFGP<br>TVSLNPATLLPLPSGKPPRLSPDLAETMAQTDLTDQPLPDADLTW<br>YTGSSFIRNGERKAGAAVTTESEVIWAASLPPGTSAQRAELIAL<br>TQALKMAKGKKLTVYTDSRYAFATAHVHGEIYRRRGLTSGKEI<br>KNKNEILALLEALFLPKRLSIIHCPGHQKGDSPQAKGNRLADDTA<br>KKAAIETQSSLTILAAA |
| SEQ ID NO: 24: MF(P)4NDKW with leader and end sequences:<br>MGSSHHHHHHSSGLVPRGSHMTLNIEDEYRLHETSKEPDVSLGST<br>WLSDFPQAWAETGGMGLAVRQAPLIIPLKATSTPVSIKQYPMSQE<br>ARLGIKPHIQRLLDQGILVPCQSPWNTPLLPVKKPGTNDYRPVQD<br>LREVNKRVEDIHPTVPNPYNLLSGLPPSHQWYTVLDLKDAFFCLR<br>LHPTSQPLFAFEWRDPEMGISGQLTWTRLPQGFKNSPTLFEALH<br>RDLADFRIQHPDLILLQYVDDLLLAAATRTECLEGTKALLETLGN<br>KGYRASAKKAQICLQEVTYLGYSLKDGQRWLTKARKEAILSIPVP<br>KNPRQVREFLGTAGYCRLWIPGFAELAAPLYPLTRPGTLFQWGTE<br>QQLAFENIRKALLSSPALGLPDITKPFELFIDENSGFAKGVLVQK |

LGPWKRPVAYLSKKLDTVASGWPPCLRMVAAIAILVKDAGKLTLG
QPLTILTSHPVEALVRQPPNKWLSNARMTHYQAMLLDAERVHFGP
TVSLNPATLLPLPSGKPPRLSPDLAETMAQTDLTDQPLPDADLTW
YTDGSSFIRNGERKAGAAVTTESEVIWAASLPPGTSAQRAELIAL
TQALKMAKGKKLTVYTDSRYAFATAHVAGEIYRRGALTSEGKEI
KNKNEILALLEALFLPKRLSIIHCPGHQKGDSPQAKGNRLADDTA
KKAATETQSSLTILAAA

SEQ ID NO: 25: MF(P)4NGWN with leader and end sequences:
MGSSHHHHHHSSGLVPRGSHMTLNIEDEYRLHETSKEPDVSLGST
WLSDFPQAWAETGGMGLAVRQAPLIIPLKATSTPVSIKQYPMSQE
ARLGIKPHIQRLLDQGILVPCQSPWNTPLLPVKKPGTNDYRPVQD
LREVNKRVEDIHPTVPNPYNLLSGLPPSHQWYTVLDLKDAFFCLR
LHPTSQPLFAFEWRDPEMGISGQLTWTRLPQGFKNSPTLFAEALH
RDLADFRIQHPDLILLQYVDDLLLAAATRTECLEGTKALLETLGN
KGYRASAKKAQICLQEVTYLGYSLKDGQRWLTKARKEAILSIPVP
KNPRQVREFLGTAGYCRLWIPGFAELAAPLYPLTRPGTLFQWGTE
QQLAFENIRKALLSSPALGLPDITKPFELFIDENSGFAKGVLVQK
LGPWKRPVAYLSKKLDTVASGWPPCLRMVAAIAILVKDAGKLTLG
QPLTILTSHPVEALVRQPPNKWLSNARMTHYQAMLLDAERVHFGP
TVSLNPATLLPLPSGKPPRLSPDLAETMAQTDLTDQPLPDADLTW
YTDGSSFIRNGERKAGAAVTTESEVIWAASLPPGTSAQRAELIAL
TQALKMAKGKKLTVYTDSRYAFATAHVHGEIYRRGALTSEGKEI
KNKNEILALLEALFLPKRLSIIHCPGHQKGDSPQAKGNRLADDTA
KKAATETQSSLTILAAA SEQ ID NO: 26: 1/3 FLV N-terminus
MTLQLEEEYRLFEPESTQKQEMDIWLKNFPQAWAETGGMGMAHCQ
APVLIQLKATATPISIRQYPMPHEAYQGIKPHIRRMLDQGILKPC
QSPWNTPLLPVKKPGTKDYRPVQDLREVNKRVEDIHPTVPNPYNL
LSTLPPSHPWYTVLDLKDAFFCLRLHSESQLLFAFEWRDPEIGLS
GQLTWTRLPQGFKNSPTLFDEALHSDLADFRVRYPALVLLQYVDD
LLLAAATRTECLEGTKALLETLGNKGYRASAKKAQICLQEVTYLG
YSLKDGQRW 2/3 FLV N-terminus
SEQ ID NO: 27
MTLQLEEEYRLFEPESTQKQEMDIWLKNFPQAWAETGGMGMAHCQ
APVLIQLKATATPISIRQYPMPHEAYQGIKPHIRRMLDQGILKPC
QSPWNTPLLPVKKPGTKDYRPVQDLREVNKRVEDIHPTVPNPYNL
LSTLPPSHPWYTVLDLKDAFFCLRLHSESQLLFAFEWRDPEIGLS
GQLTWTRLPQGFKNSPTLFDEALHSDLADFRVRYPALVLLQYVDD
LLLAAATRTECLEGTKALLETLGNKGYRASAKKAQICLQEVTYLG
YSLKDGQRWLTKARKEAILSIPVPKNPRQVREFLGTAGYCRLWIP
GFAELAAPLYPLTRPGTLFQWGTEQQLAFENIRKALLSSPALGLP
DITKPFELFIDENSGFAKGVLVQKLGPWKRPVAYLSKKLDTVASG
WPPCLRMVAAIAILVKDAGKLTLGQPLTILTSHPVEALVRQPPNK
WLSNARMTHYQAMLLDAERVHFGPTVSLNPATLLPLPSGKPPRLS
PD 2/3 MLV C-terminus
SEQ ID NO: 28
LTEARKETVMGQPTPKTPRQLREFLGTAGFCRLWIPGFAEMAAPL
YPLTKTGTLFNWGPDQQKAYQEIKQALLTAPALGLPDLTKPFELF
VDEKQGYAKGVLTQKLGPWRRPVAYLSKKLDPVAAGWPPCLRMVA
AIAVLTKDAGKLTMGQPLVILAPHAVEALVKQPPDRWLSNARMTH
YQALLLDTDRVQFGPVVALNPATLLPLPEEGLQHDCLDILAEAHG
TRSDLTDQPLPDADHTWYTDGSSFLQEGQRKAGAAVTTETEVIWA
RALPAGTSAQRAELIALTQALKMAEGKKLNVYTDSRYAFATAHIH
GEIYRRRGLLTSEGKEIKNKDEILALLKALFLPKRLSIIHCPGHQ
KGNSAEARGNRMADQAAREVATRETPGTSTLL 1/3 MLV C-terminus
SEQ ID NO: 29
ILAEAHGTRSDLTDQPLPDADHTWYTDGSSFLQEGQRKAGAAVTT
ETEVIWARALPAGTSAQRAELIALTQALKMAEGKKLNVYTDSRYA
FATAHIHGEIYRRRGLLTSEGKEIKNKDEILALLKALFLPKRLSI
IHCPGHQKGNSAEARGNRMADQAAREVATRETPGTSTLL FM1 (1/3 FLV-2/3 MLV RT)
SEQ ID NO: 30
MTLQLEEEYRLFEPESTQKQEMDIWLKNFPQAWAETGGMGMAHCQ
APVLIQLKATATPISIRQYPMPHEAYQGIKPHIRRMLDQGILKPC
QSPWNTPLLPVKKPGTKDYRPVQDLREVNKRVEDIHPTVPNPYNL
LSTLPPSHPWYTVLDLKDAFFCLRLHSESQLLFAFEWRDPEIGLS
GQLTWTRLPQGFKNSPTLFDEALHSDLADFRVRYPALVLLQYVDD
LLLAAATRTECLEGTKALLETLGNKGYRASAKKAQICLQEVTYLG
YSLKDGQRWLTEARKETVMGQPTPKTPRQLREFLGTAGFCRLWIP
GFAEMAAPLYPLTKTGTLFNWGPDQQKAYQEIKQALLTAPALGLP
DLTKPFELFVDEKQGYAKGVLTQKLGPWRRPVAYLSKKLDPVAAG
WPPCLRMVAAIAVLTKDAGKLTMGQPLVILAPHAVEALVKQPPDR
WLSNARMTHYQALLLDTDRVQFGPVVALNPATLLPLPEEGLQHDC
LDILAEAHGTRSDLTDQPLPDADHTWYTDGSSFLQEGQRKAGAAV
TTETEVIWARALPAGTSAQRAELIALTQALKMAEGKKLNVYTDSR
YAFATAHIHGEIYRRRGLLTSEGKEIKNKDEILALLKALFLPKRL
SIIHCPGHQKGNSAEARGNRMADQAAREVATRETPGTSTLL

FM2 (2/3 FLV-1/3 MLV RT)

SEQ ID NO: 31
MTLQLEEEYRLFEPESTQKQEMDIWLKNFPQAWAETGGMGMAHCQ
APVLIQLKATATPISIRQYPMPHEAYQGIKPHIRRMLDQGILKPC
QSPWNTPLLPVKKPGTKDYRPVQDLREVNKRVEDIHPTVPNPYNL
LSTLPPSHPWYTVLDLKDAFFCLRLHSESQLLFAFEWRDPEIGLS
GQLTWTRLPQGFKNSPTLFDEALHSDLADFRVRYPALVLLQYVDD
LLLAAATRTECLEGTKALLETLGNKGYRASAKKAQICLQEVTYLG
YSLKDGQRWLTKARKEAILSIPVPKNPRQVREFLGTAGYCRLWIP
GFAELAAPLYPLTRPGTLFQWGTEQQLAFENIRKALLSSPALGLP
DITKPFELFIDENSGFAKGVLVQKLGPWKRPVAYLSKKLDTVASG
WPPCLRMVAAIAILVKDAGKLTLGQPLTILTSHPVEALVRQPPNK
WLSNARMTHYQAMLLDAERVHFGPTVSLNPATLLPLPSGKPPRLS
PDILAEAHGTRSDLTDQPLPDADHTWYTDGSSFLQEGQRKAGAAV
TTETEVIWARALPAGTSAQRAELIALTQALKMAEGKKLNVYTDSR
YAFATAHIHGEIYRRRGLLTSEGKEIKNKDEILALLKALFLPKRL
SIIHCPGHQKGNSAEARGNRMADQAAREVATRETPGTSTLL

Wild type MLV RT sequence
SEQ ID NO: 32
TLNIEDEHRLHETSKEPDVSLGSTWLSDFPQAWAETGGMGLAVRQ
APLIIPLKATSTPVSIKQYPMSQEARLGIKPHIQRLLDQGILVPC
QSPWNTPLLPVKKPGTNDYRPVQDLREVNKRVEDIHPTVPNPYNL
LSGLPPSHQWYTVLDLKDAFFCLRLHPTSQPLFAFEWRDPEMGIS
GQLTWTRLPQGFKNSPTLFDEALHRDLADFRIQHPDLILLQYVDD
LLLAATSELDCQQGTRALLQTLGNLGYRASAKKAQICQKQVKYLG
YLLKEGQRWLTEARKETVMGQPTPKTPRQLREFLGTAGFCRLWIP
GFAEMAAPLYPLTKTGTLFNWGPDQQKAYQEIKQALLTAPALGLP
DLTKPFELFVDEKQGYAKGVLTQKLGPWRRPVAYLSKKLDPVAAG
WPPCLRMVAAIAVLTKDAGKLTMGQPLVILAPHAVEALVKQPPDR
WLSNARMTHYQALLLDTDRVQFGPVVALNPATLLPLPEEGLQHNC
LDILAEAHGTRPDLTDQPLPDADHTWYTDGSSLLQEGQRKAGAAV
TTETEVIWAKALPAGTSAQRAELIALTQALKMAEGKKLNVYTDSR
YAFATAHIHGEIYRRRGLLTSEGKEIKNKDEILALLKALFLPKRL
SIIHCPGHQKGHSAEARGNRMADQAARKAAITETPDTSTLL Wild type FLV RT sequence
SEQ ID NO: 33
TLQLEEEYRLFEPESTQKQEMDIWLKNFPQAWAETGGMGMAHCQA
PVLIQLKATATPISIRQYPMPHEAYQGIKPIHRRMLDQGILKPCQ
SPWNTPLLPVKKPGTKDYRPVQDLREVNKRVEDIHPTVPNPYNLL
STLPPSEIPWYTVLDLKDAFFCLRLHSESQLLFAFEWRDPEIGLS
GQLTWTRLPQGFKNSPTLFDEALHSDLADFRVRYPALVLLQYVDD
LLLAAATRTECLEGTKALLETLGNKGYRASAKKAQICLQEVTYLG
YSLKDGQRWLTKARKEAILSIPVPKNPRQVREFLGTAGYCRLWIP
GFAELAAPLYPLTRPGTLFQWGTEQQLAFENIRKALLSSPALGLP
DITKPFELFIDENSGFAKGVLVQKLGPWKRPVAYLSKKLDTVASG
WPPCLRMVAAIAILVKDAGKLTLGQPLTILTSHPVEALVRQPPNK
WLSNARMTHYQAMLLDAERVHFGPTVSLNPATLLPLPSGKPPRLS
PDLAETMAQTDLTDQPLPDADLTWYTDGSSFIRNGERKAGAAVTT
ESEVIWAASLPPGTSAQRAELIALTQALKMAKGKKLTVYTDSRYA
FATAHVHGEIYRRRGLLTSEGKEIKNKNEILALLEALFLPKRLSI
IHCPGHQKGDSPQAKGNRLADDTAKKAATETQSSLTIL SEQ ID NO: 34: NF5PNAIYC without leader or end sequences:
MTLNIEDEYRLHETSKEPDVSLGSTWLSDFPQAWAETGGMGLAVR
QAPLIIPLKATSTPVSIKQYPMSQEARLGIKPHIQRLLDQGILVP
CQSPWNTPLLPVKKPGTNDYRPVQDLREVNKRVEDIHPTVPNPYN
LLSGXPPSHQWYTVLDLKDAFFCLRLHPTSQPLFAFEWRDPEMGI
SGQLTWTRLPQGFKNSPTLFXEALHRDLADFRIQHPDLILLQYVD
DLLLAATSELDCQQGTRALLQTLGNLGYRASAKKAQICQKQVKYL
GYLLKEGQRWLTKARKEAILSIPVPKNPRQVREFLGTAGYCRLWI
PGFAELAAPLYPLTRPGTLFQWGTEQQLAFENIRKALLSSPALGL
PDITKPFELFIDENSGFAKGVLVQKLGPWKRPVAYLSKKLDTVAS
GWPPCLRMVAAIAILVKDAGKLTLGQPLTILTSHPVEALVRQPPN
KWLSNARMTHYQAMLLDAERVHFGPTVSLNPATLLPLPSGKPPRL
SPDLAETMAQTDLTDQPLPDADLTWYXGSSXIRNGERKAGAAV
TIESEVIWAASLPPGTSAQRAELIALTQALKMAKGKKLTVYTDSR
YAFATAHVHGEIYRRRGLLTSEGKEIKNKNEILALLEALFLPKRL
SIIXCPGHQKGDSPQAKGNRLADDTAKKAATETQSSLTILPIELI
EGPKRPPWEY SEQ ID NO: 35: MF4(P)GC without leader or end sequences:
MTLNIEDEYRLHETSKEPDVSLGSTWLSDFPQAWAETGGMGLAVR
QAPLIIPLKATSTPVSIKQYPMSQEARLGIKPHIQRLLDQGILVP
CQSPWNTPLLPVKKPGTNDYRPVQDLREVNKRVEDIHPTVPNPYN
LLSGXPPSHQWYTVLDLKDAFFCLRLHPTSQPLFAFEWRDPEMGI
SGQLTWTRLPQGFKNSPTLFXEALHRDLADFRIQHPDLILLQYVD
DLLLAAATRTECLEGTKALLETLGNKGYRASAKKAQICLQEVTYL
GYSLKDGQRWLTKARKEAILSIPVPKNPRQVREFLGTAGYCRLWI
PGFAELAAPLYPLTRPGTLFQWGIEQQLAFENIRKALLSSPALGL
PDITKPFELFIDENSGFAKGVLVQKLGPWKRPVAYLSKKLDTVAS
GWPPCLRMVAAIAILVKDAGKLTLGQPLTILTSHPVEALVRQPPN
KWLSNARMTHYQAMLLDAERVHFGPTVSLNPATLLPLPSGKPPRL
SPDLAETMAQTDLTDQPLPDADLTWYXGSSFIRNGERKAGAAV

SEQUENCES

TTESEVIWAASLPPGTSAQRAELIALTQALKMAKGKKLTVYTDSR
YAFATAHVHGEIYRRRGXLTSXGKEIKNKNEILALLEALFLPKRL
SIIHCPGHQKGDSPQAKGNRLADDTAKKAATETQSSLTILPIELI
EGPKRPPWEY

SEQ ID NO: 36: NF5PNAIYC MLVRT portion:
MTLNIEDEYRLHETSKEPDVSLGSTWLSDFPQAWAETGGMGLAVR
QAPLIIPLKATSTPVSIKQYPMSQEARLGIKPHIQRLLDQGILVP
CQSPWNTPLLPVKKPGTNDYRPVQDLREVNKRVEDIHPTVPNPYN
LLSGXPPSHQWYTVLDLKDAFFCLRLHPTSQPLFAFEWRDPEMGI
SGQLTWTRLPQGFKNSPTLFXXEALHRDLADFRIQHPDLILLQYVD
DLLLAATSELDCQQGTRALLQTLGNLGYRASAKKAQICQKQVKYL
GYLLKEGQ SEQ ID NO: 37: NF5PNAIYC FLVRT portion:
RWLTKARKEAILSIPVPKNPRQVREFLGTAGYCRLWIPGFAELAA
PLYPLTRPGTLFQWGTEQQLAFENIRKALLSSPALGLPDITKPFE
LFIDENSGFAKGVLVQKLGPWKRPVAYLSKKLDTVASGWPPCLRM
VAAIAILVKDAGKLTLGQPLTILTSHPVEALVRQPPNKWLSNARM
THYQAMLLDAERVHFGPTVSLNPATLLPLPSGKPPRLSPDLAETM
AQTDLTDQPLPDADLTWYTXGSSXIRNGERKAGAAVTTESEVIW
AASLPPGTSAQRAELIALTQALKMAKGKKLTVYTDSRYAFATAHV
HGEIYRRRGLLTSEGKEIKNKNEILALLEALFLPKRLSIIXCPGH
QKGDSPQAKGNRLADDTAKKAATETQSSLTILPTELIEGPKRPPW
EY SEQ ID NO: 38: MF4(P)GC MLVRT portion
MTLNIEDEYRLHETSKEPDVSLGSTWLSDFPQAWAETGGMGLAVR
QAPLIIPLKATSTPVSIKQYPMSQEARLGIKPHIQRLLDQGILVP
CQSPWNTPLLPVKKPGTNDYRPVQDLREVNKRVEDIHPTVPNPYN
LLSGXPPSHQWYTVLDLKDAFFCLRLHPTSQPLFAFEWRDPEMGI
SGQLTWTRLPQGFKNSPTLFXEALHRDLADFRIQBPDLILLQ SEQ ID NO: 39: MF4(P)GC FLVRT portion
YVDDLLLAAATRTECLEGTKALLETLGNKGYRASAKKAQICLQEV
TYLGYSLKDGQRWLTKARKEAILSIPVPKNPRQVREFLGTAGYCR
LWIPGFAELAAPLYPLTRPGTLFQWGTEQQLAFENIRKALLSSPA
LGLPDITKPFELFIDENSGFAKGVLVQKLGPWKRPVAYLSKKLDT
VASGWPPCLRMVAAIAILVKDAGKLTLGQPLTILTSEIPVEALVR
QPPNKWLSNARMTHYQAMLLDAERVEIFGPTVSLNPATLLPLPSG
KPPRLSPDLAETMAQTDLTDQPLPDADLTWYTXGSSFIRNGERKA
GAAVTTESEVIWAASLPPGTSAQRAELIALTQALKMAKGKKLTVY
TDSRYAFATAHVHGEIYRRRGXLTSXGKEIKNKNEILALLEALFL
PKRLSIIHCPGHQKGDSPQAKGNRLADDTAKKAATETQSSLTILP
TELIEGPKRPPWEY SEQ ID NO: 40: NF5PNAIYC with leader and end sequences
MGSSHHHHHHSSGLVPRGSHMTLNIEDEYRLHETSKEPDVSLGST
WLSDFPQAWAETGGMGLAVRQAPLIIPLKATSTPVSIKQYPMSQE
ARLGIKPHIQRLLDQGILVPCQSPWNTPLLPVKKPGTNDYRPVQD
LREVNKRVEDIHPTVPNPYNLLSGXPPSHQWYTVLDLKDAFFCLR
LHPTSQPLFAFEWRDPEMGISGQLTWTRLPQGFKNSPTLFXEALH
RDLADFRIQHPDLILLQYVDDLLLAATSELDCQQGTRALLQTLGN
LGYRASAKKAQICQKQVKYLGYLLKEGQ**RWLTKARKEAILSIPVP
KNPRQVREFLGTAGYCRLWIPGFAELAAPLYPLTRPGTLFQWGTE
QQLAFENIRKALLSSPALGLPDITKPFELFIDENSGFAKGVLVQK
LGPWKRPVAYLSKKLDTVASGWPPCLRMVAAIAILVKDAGKLTLG
QPLTILTSHPVEALVRQPPNKWLSNARMTHYQAMLLDAERVHFGP
TVSLNPATLLPLPSGKPPRLSPDLAETMAQTDLTDQPLPDADLTW
YTXGSSXIRNGERKAGAAVTTESEVIWAASLPPGTSAQRAELIAL
TQALKMAKGKKLTVYTDSRYAFATAHVHGEIYRRRGLLTSEGKEI
KNKNEILALLEALFLPKRLSIIXCPGHQKGDSPQAKGNRLADDTA
KKAATETQSSLTILPTELIEGPKRPPWEYAAA**

SEQ ID NO: 41: MF4(P)GC with leader and end sequences
MGSSHHHHHHSSGLVPRGSHMTLNIEDEYRLHETSKEPDVSLGST
WLSDFPQAWAETGGMGLAVRQAPLIIPLKATSTPVSIKQYPMSQE
ARLGIKPHIQRLLDQGILVPCQSPWNTPLLPVKKPGTNDYRPVQD
LREVNKRVEDIHPTVPNPYNLLSGXPPSHQWYTVLDLKDAFFCLR
LHPTSQPLFAFEWRDPEMGISGQLTWTRLPQGFKNSPTLFXEALH
RDLADFRIQHPDLILLQYVDDLLLAAATRTECLEGTKALLETLGN
KGYRASAKKAQICLQEVTYLGYSLKDGQRWLTKARKEAILSIPVP
KNPRQVREFLGTAGYCRLWIPGFAELAAPLYPLTRPGTLFQWGTE
QQLAFENIRKALLSSPALGLPDITKPFELFIDENSGFAKGVLVQK
LGPWKRPVAYLSKKLDTVASGWPPCLRMVAAIAILVKDAGKLTLG
QPLTILTSHPVEALVRQPPNKWLSNARMTHYQAMLLDAERVHFGP
TVSLNPATLLPLPSGKPPRLSPDLAETMAQTDLTDQPLPDADLTW
YTXGSSFIRNGERKAGAAVTTESEVIWAASLPPGTSAQRAELIAL
TQALKMAKGKKLTVYTDSRYAFATAHVHGEIYRRRGXLTSXGKEI
KNKNEILALLEALFLPKRLSIIHCPGHQKGDSPQAKGNRLADDTA
KKAATETQSSLTILPTELIEGPKRPPWEYAAA

What is claimed is:

1. A hybrid reverse transcriptase comprising a finger domain, a palm domain, a thumb domain, a connection domain and an RNase H domain, the hybrid reverse transcriptase comprising:
   a portion of mouse leukemia virus reverse transcriptase (MLVRT) comprising the finger domain and the palm domain, wherein the portion of the MLVRT is at least 95% identical to SEQ ID NO:1, said portion of the MLVRT linked to
   a portion of feline leukemia virus reverse transcriptase (FLVRT) comprising the thumb domain, the connection domain, and the RNase H domain, wherein the portion of the FLVRT is at least 95% identical to SEQ ID NO:5.

2. The hybrid reverse transcriptase of claim 1, wherein the portion of the MLVRT comprises SEQ ID NO:1 and the portion of the FLVRT comprises SEQ ID NO:5.

3. The hybrid reverse transcriptase of claim 2, wherein the portion of the FLVRT comprises SEQ ID NO:6 or SEQ ID NO:10.

4. The hybrid reverse transcriptase of claim 3, wherein the portion of the FLVRT comprises SEQ ID NO:7, SEQ ID NO:8, SEQ ID NO:9, or SEQ ID NO:11.

5. The hybrid reverse transcriptase of claim 2, wherein the portion of the MLVRT comprises SEQ ID NO:2.

6. The hybrid reverse transcriptase of claim 2, wherein the portion of the MLVRT comprises SEQ ID NO:3 or SEQ ID NO:4.

7. The hybrid reverse transcriptase of claim 2, wherein:
the portion of the MLVRT comprises SEQ ID NO:4 and
    the portion of the FLVRT comprises SEQ ID NO:7; or
the portion of the MLVRT comprises SEQ ID NO:4 and
    the portion of the FLVRT comprises SEQ ID NO:8; or
the portion of the MLVRT comprises SEQ ID NO:4 and
    the portion of the FLVRT comprises SEQ ID NO:9; or
the portion of the MLVRT comprises SEQ ID NO:3 and
    the portion of the FLVRT comprises SEQ ID NO:11; or
the portion of the MLVRT comprises SEQ ID NO:3 and
    the portion of the FLVRT comprises SEQ ID NO:10; or
the portion of the MLVRT comprises SEQ ID NO:4 and
    the portion of the FLVRT comprises SEQ ID NO:13.

8. The hybrid reverse transcriptase of claim 2, wherein the hybrid reverse transcriptase comprises a sequence at least 95% identical to SEQ ID NO: 14, 15, 16, 17, 18, 19, 34, or 35.

9. The hybrid reverse transcriptase of claim 1, having at least one mutation that improves thermostability.

10. A reaction mixture comprising:
an RNA or DNA template; and
the hybrid reverse transcriptase of claim 1.

11. A method of performing reverse transcription, the method comprising
contacting the hybrid reverse transcriptase of claim 1 in a reaction mixture with a template RNA and a primer that hybridizes to the template RNA under conditions such that the hybrid reverse transcriptase extends the primer in a template RNA-dependent manner to form a cDNA.

\* \* \* \* \*